United States Patent [19]

Salhi et al.

[11] Patent Number: 4,656,166
[45] Date of Patent: Apr. 7, 1987

[54] ANTIBIOTIC COMPOUNDS DERIVED FROM CEPHALOSPORINS, PROCESS FOR THEIR PRODUCTION AND PHARMACEUTICAL COMPOSITIONS

[75] Inventors: Ali Salhi, Saint-Gely-du-Fesc; Dominique Olliero, Montpellier, both of France

[73] Assignee: Sanofi, Paris, France

[21] Appl. No.: 612,896

[22] Filed: May 22, 1984

[30] Foreign Application Priority Data

May 27, 1983 [FR] France ............... 83 08862

[51] Int. Cl.⁴ ............... C07D 501/34; C07D 501/36; A61K 31/545
[52] U.S. Cl. ............... 514/202; 514/204; 514/206; 514/207; 540/222; 540/226; 540/227; 540/228
[58] Field of Search ............... 544/27; 514/204, , 206, 514/207, 202; 540/226, 227, 228, 222

[56] References Cited

U.S. PATENT DOCUMENTS

| | | | |
|---|---|---|---|
| 3,935,204 | 1/1976 | Dahlén et al. | 544/24 |
| 4,034,090 | 7/1977 | Berger et al. | 544/27 |
| 4,097,595 | 6/1978 | Heymes | 544/27 |
| 4,152,432 | 5/1979 | Haymes et al. | 544/19 |
| 4,278,671 | 7/1981 | Ochiai et al. | 540/225 |
| 4,338,438 | 7/1982 | Christensen et al. | 544/28 |
| 4,366,153 | 12/1982 | Takaya et al. | 514/204 |
| 4,396,619 | 8/1983 | Lunn et al. | 514/202 |
| 4,399,131 | 8/1983 | Durekhermer et al. | 514/205 |

FOREIGN PATENT DOCUMENTS

| | | | |
|---|---|---|---|
| 768844 | 6/1971 | Belgium | 514/204 |
| 29557 | 6/1981 | European Pat. Off. | 544/27 |
| 55465 | 7/1982 | European Pat. Off. | 540/228 |
| 127543 | 12/1984 | European Pat. Off. | 540/228 |
| 2485540 | 12/1981 | France | 540/227 |
| 2501209 | 9/1982 | France | 540/228 |
| 2506307 | 11/1982 | France | 540/227 |

Primary Examiner—Donald G. Daus
Assistant Examiner—G. Hendricks
Attorney, Agent, or Firm—Stevens, Davis, Miller & Mosher

[57] ABSTRACT

The compounds according to the invention correspond to the formula:

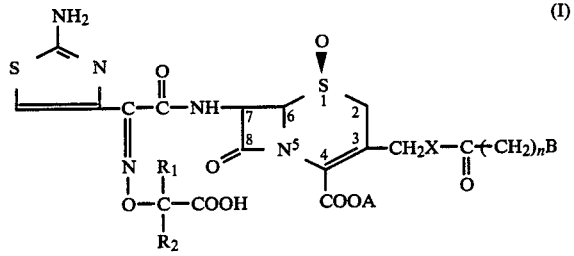

in which:

The COOA group at the 4 position is an acid radical, or an alkaline or alkaline-earth salt, or an amino acid or amine salt, for example triethylamine or ethanolamines, or an easily hydrolyzable or metabolically labile and pharmaceutically acceptable ester radical.

X denotes an oxygen atom or a sulfur atom n is zero or 1

$R_1$ and $R_2$ each denote independently hydrogen or a lower alkyl group, preferably a methyl group, or $R_1$ and $R_2$ taken together with the carbon atom to which they are linked form a cyclobutyl or cyclopentyl nucleus.

B is the residue of a primary or secondary amine.

4 Claims, No Drawings

ANTIBIOTIC COMPOUNDS DERIVED FROM CEPHALOSPORINS, PROCESS FOR THEIR PRODUCTION AND PHARMACEUTICAL COMPOSITIONS

The present invention relates to derivatives of the cephalosporin family, the process for their preparation and their therapeutic use.

The compounds according to the invention correspond to the formula:

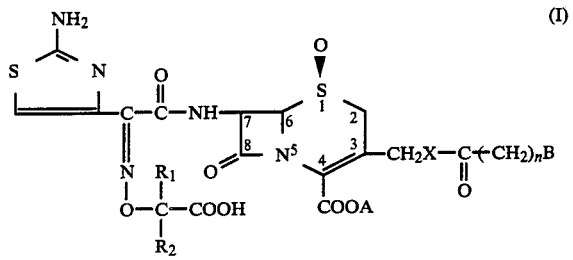

in which:

The COOA group at the 4 position is an acid radical, or an alkaline or alkaline-earth salt, or an amino acid or amine salt, for example triethylamine or ethanolamines, or an easily hydrolyzable or metabolically labile and pharmaceutically acceptable ester radical.

X denotes an oxygen atom or a sulfur atom n is zero or 1

$R_1$ and $R_2$ each denote independently hydrogen or a lower alkyl group, preferably a methyl group, or $R_1$ and $R_2$ taken together with the carbon atom to which they are linked form a cyclobutyl or cyclopentyl nucleus.

B is the residue of a primary or secondary amine selected by the following groups:

Z—NH—R where Z is an alkylene group with a straight or branched chain having from 2 to 7 carbon atoms, possibly interrupted by a sulfur atom and possible substituted by a hydroxyl, thiol, methylthio, amino, acetamido, carbamoyl, phenyl, hydroxyphenyl or imidazolyl group.

Z can also be a cyclopentylidene or cyclohexylidene group. R represents a hydrogen atom or an alkyl group having from 1 to 3 carbon atoms.

Z'—Alk—NH—R where Z' represents a 1,2-phenylene or 1,3-phenylene or 1,4-phenylene group possibly substituted by a halogen atom or by 1 or 2 methoxy groups or by 1, 2 or 3 methyl groups or Z' represents a 1,2-cyclohexylene, 1,3-cyclohexylene or 1,4-cyclohexylene group.

Alk represents a straight or branched alkyl group having from 1 to 3 carbon atoms.

R is as defined above.

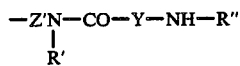

where Z' is as defined above.

Y denotes an alkyl group $(CH_2)_m$ in which $m=0, 1, 2, 3$ or 4, a branched alkyl group having 2 or 3 carbon atoms or also Y with NH—R" constitutes a ring

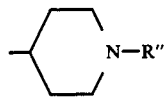

R' and R", identical or different, have the same meaning as that given for R above.

Z"—NH—R where Z" is a 1,3-cyclohexylene or 1,4-cyclohexylene and R is as previously defined.

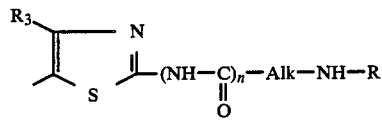

where $R_3$ represents a hydrogen atom or a methyl group. $n=0$ or 1 and Alk and R are as previously defined.

A 2-piperidyl, 3-piperidyl or 4-piperidyl group possibly substituted on the nitrogen atom by a —CO—Alk—$NH_2$ group

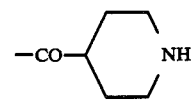

where Alk is as previously defined.

The salts that the compounds of Formula 1 can give with pharmaceutically acceptable acids form an integral part of the invention.

As a result of the presence in the formula of an oxime group, the compounds (I) exist in two isomeric forms syn and anti. The syn isomers whose therapeutic activity is higher are the preferred compounds.

It is understood that the compounds (I) indicated above can exist:
either in the form indicated in Formula (I),
or in tautomeric form (I'):

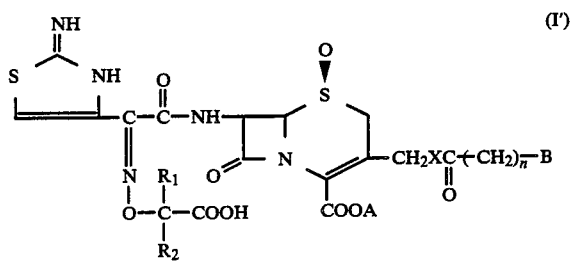

in which A, X, $R_1$, $R_2$, B and n have the previously indicated meanings.

The invention also relates to a process for the preparation of compounds of Formula (I).

According to the reaction diagram below, this process consists of first of all acylating 4-tertiobutyl-1-S-oxide 7-amino-3-bromomethyl-3-cepheme carboxylate (II) with the acid (III) to obtain the compound (IV) described in European patent application No. 60,745. To the compound IV, is then added the acid B—($CH_2$)$_n$—COOH or the thioacid B($CH_2$)$_n$COSH whose amine function must be previously protected, according to a known method, by a protective group like tertiobutoxycarbonyl or trichlorethoxycarbonyl, for example, B' then represents the group B in which the amine function is protected.

The addition of the sodium or potassium salt of the acid B'—(CH$_2$)$_n$COOH to the compound (IV) is preferably done in an aprotic polar solvent, for example dimethylformamide, whilst the addition of the sodium or potassium salt of the thioacid B'—(CH$_2$)HD nCOSH can be done in an apolar solvent like tetrahydrofuran. The compound (V) is obtained.

In the case of the thioacids, to prepare the compounds (V), it is possible to use the thioacid itself instead of an alkali salt. The operation is then in anhydrous acetone in the presence of potassium bicarbonate and sodium iodide.

Finally, to end with the compound (I), the protective groups on the amines and the tertiobutyl esters are removed by a known process, in particular by hydrolysis in an acid medium by using, for example, trifluoracetic acid or a mixture of formic acid and hydrochloric acid.

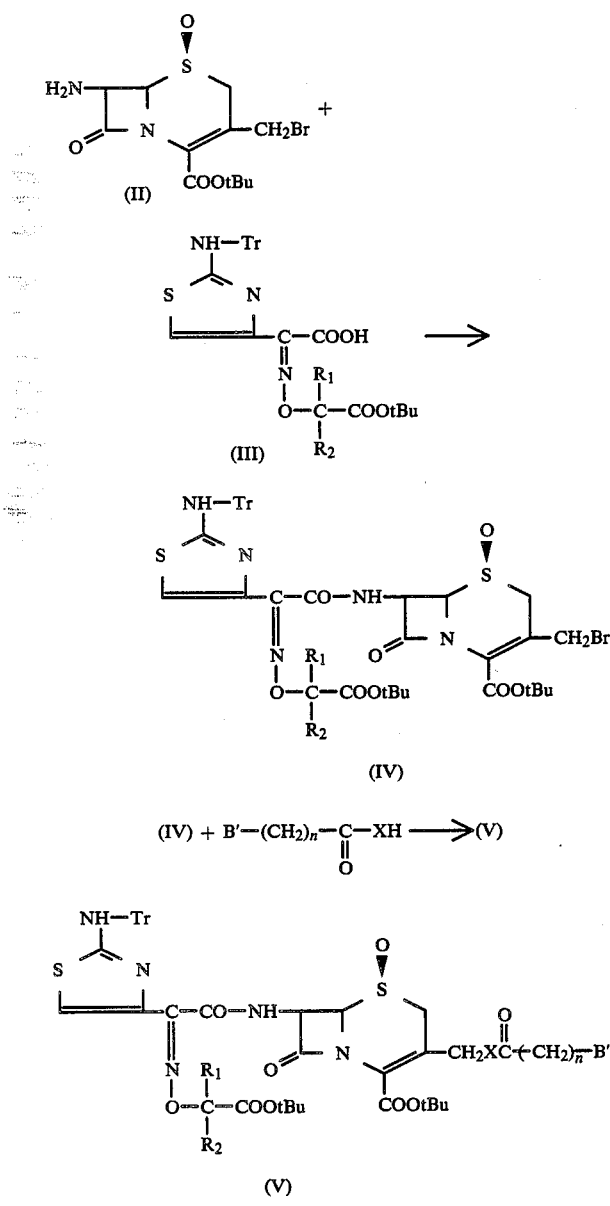

-continued

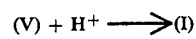

T$_r$ represents trityl, tBu tertiobutyl, X, R$_1$, R$_2$, n, B' and B have the previously indicated meanings.

The compounds (I) of the invention in which A is other than H are obtained from compounds (I) in which A is H by reactions known in themselves.

Thus the inorganic salts are obtained by the action on compounds (I), in which A is H, of an inorganic base such as soda or potash or sodium bicarbonate in an equimolecular amount; the salification reaction is carried in a solvent such as water or ethanol and the salt obtained is isolated by evaporation of the solution.

The salts of organic bases are obtained by the action on a solution of the acid I (A=H), in a solvent or a mixture of suitable solvents, of an equimolecular amount of the organic base. The salt is isolated by precipitation with ether.

The esters are obtained by known esterification processes; for example there will advantageously be used the action of a halogen derivative on a salt such as the sodium salt of the acid; preferably the reaction will be carried out in a solvent capable of dissolving the starting acid derivative, for example in dimethylformamide.

The syn and anti form isomers are obtained by a suitable choice of reagents.

the following examples enable the scope of the invention to be further understood without however limiting it.

Thus as is usual in this family of compounds, the products according to the invention do not have a distinct melting point but only points of decomposition which do not permit them to be characterized.

The products will therefore be characterized by their nuclear magnetic resonance spectrum recorded at 60 MHz or at 250 MHz, the internal standard being hexamethyldisiloxane. The spectra are recorded in deuteriated dimethylsulfoxide with the exceptions indicated in the description of the spectrum: 50 mg of product in 0.5 ml of solvent at 60 MHz and 10 mg in 0.5 ml at 250 MHz. The chemical displacements are measured at ±0.01 ppm and the coupling constants at ±0.5 Hz.

The following abbreviations will be used:
S: singlet
D: doublet
D of D: doublet of doublet
S.e.: widened singlet
M: multiplet
Q: quadruplet
AB: AB system
J: represents the coupling constant.

In addition elementary microanalyses were carried out in each case and are in agreement with the formulae indicated.

The infra-red spectra also serve to characterize the products obtained. They were recorded between 4,000 cm$^{-1}$ and 600 cm$^{-1}$ from a preparation constituted by a potassium bromide tablet containing the product at a concentration of about 2%; when the spectrum is recorded in solution at 1% in a chlorinated solvent, the nature of the latter is mentioned. The elongation vibration frequency of the carbonyl groups of the molecule is noted (νCO).

EXAMPLE 1

7-[2-(2-Amino 4-thiazolyl)2-(2-carboxy 2-propyl oxyimino)acetamido]3-(4-piperidinyl)carbonyl oxymethyl 3-cepheme 4-carboxylic1β-S-oxide acid trifluoroacetate syn isomer. SR 41 862

(a)

7-[2-(2-tritylamino-4-thiazolyl)2-(2-tertiobutoxycarbonyl 2-propyl oxyimino)acetamido]3-(1-tertiobutoxycarbonyl 4-piperidinyl carbonyl oxymethyl)3-cepheme 1-β-S-oxide carboxylate of Tertiobutyl; syn isomer

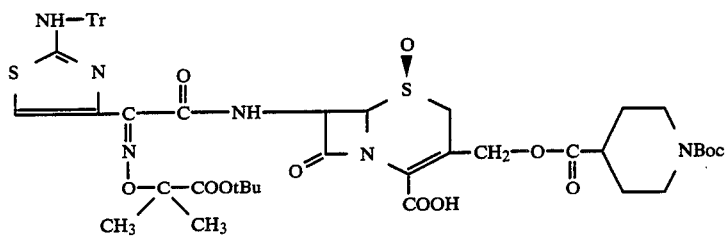

tBu and T have the previously indicated meanings, Boc denotes the tertiobutoxycarbonyl group.

To a solution of 1.38 g of 4-tertiobutyl 1-β-S-oxide 7-[2-(2-tritylamino 4-thiazolyl)2-(2-tertiobutoxycarbonyl 2-propyl oxyimino)acetamido]3-bromomethyl 3-cepheme carboxylate syn isomer, in 20 ml of anhydrous dimethylformamide, are added 1 g of 1-tertiobutyloxycarbonyl 4-piperidinyl carboxylic acid and 1.5 g of potassium bicarbonate.

After 17 hours of stirring at ambiant temperature (20°-25° C.) the reaction mixture is poured on to 200 ml of ice water. After vigorous stirring, the crystals were filtered and washed with water. They are then taken up with 70 ml of dichloromethane. The organic phase is then washed with a saturated solution of sodium chloride, dried over magnesium sulfate and evaporated. The lacquer obtained is chromatographed on a column of 50 g of silica. It is eluted with a dichloromethane-ethyl acetate mixture 90-10 (vol/vol). After evaporation of the fractions containing the compound and trituration in hexane, 1.3 g of the expected compound is obtained.

IR Spectrum: ∂ CO 1805 cm$^{-1}$: C=O at 8 of the β lactame; 1735 cm$^{-1}$: C=O of the tertiobutyl esters and of the ester at the 3 position; 1695 cm$^{-1}$: C=O of the tertiobutoxycarbonyl protecting group of the piperidine.

NMR Spectrum at 250 MHz. 1H at 8.75 ppm (S, NHTr)—1H at 8.10 ppm (D, J=9 Hz, CONH)—15H at 7.25 ppm (M, H aromatics)—1H at 6.73 ppm (S, H thiazole)—1H at 5.81 ppm (M, H$_7$)—1H at 5.25 ppm (D, J=13 Hz, CH$_2$OCO)—1H at 4.94 ppm (D, J=4 Hz, H$_6$)—1H at 4.55 ppm (D, J=13 Hz, CH$_2$OCO)—1H at 3.90 ppm (D, J=17 Hz, CH$_2$SO)—2H at 3.79 ppm (D, J=12 Hz, HCN Boc equatorials)—1H at 3.53 ppm (D, J=17 Hz, CH$_2$SO)—2H at 2.75 ppm (M, HCH Boc arials)—1H at 2.50 ppm (M, HCCO$_2$)—2H at 1.75 ppm (D, J=12 Hz, HCHCO$_2$ equatorials)—9H at 1.46 ppm (S, CO$_2$, tBU)—2H at 1.40 ppm (M, HCCHCO$_2$ axials)—6H at 1.39 ppm (S, (CH$_3$)$_2$C)—9H at 1.36 ppm (S, CO$_2$tBU)—9H at 1.29 ppm (S, Boc N).

(b) SR 41 862

0.8 g of the compound obtained above was dissolved in 10 ml of trifluoroacetic acid. After 45 minutes at 23° C. the acid was evaporated under vacuum without heating and the oily residue was crystallized by the addition of 50 ml of isopropyl ether. The crystals were filtered and washed with isopropyl ether and then with hexane. They were then dried under vacuum over phosphoric anhydride. 0.66 g of the expected products was obtained.

IR Spectrum: ∂ CO 1795 cm$^{-1}$: C=O at 8 of the β lactam; 1735 cm$^{-1}$: C=O of the ester at 3; 1680 cm$^{-1}$ wide band: C=O of the acids of the molecule, of the amide at 7, of the ions CF$_3$CO$_2^-$.

NMR Spectrum at 250 MHz. 2H at 8.60 ppm (S.e., NH$_2^+$)—1H at 8.50 ppm (D, J+9 Hz, CONH)—3H at 8.40 ppm (S.e., NH$_3^+$)—1H at 6.68 ppm (S, H thiazole)—1H at 6.0 ppm (D of D, J$_1$=9 Hz, J$_2$=4 Hz, H$_7$)—1H at 5.16 ppm (D, J=13 Hz, CH$_2$OCO)—1H at 4.97 ppm (D, J=4 Hz, H$_6$)—1H at 4.60 ppm (D, J=13 Hz, CH$_2$OCO)—1H at 3.90 ppm (D, J=17 Hz, CH$_2$SO)—1H at 3.55 ppm (D, J=17 Hz, CH$_2$SO)—2H at 3.25 ppm (M, CH$_2$NH)—2H at 2.90 ppm (M, CH$_2$NH)—1H at 2.66 ppm (M, CHCO$_2$)—2H at 1.90 ppm (M, CH$_2$CH)—2H at 1.70 ppm (M, CH$_2$CH)—6H at 1.44 ppm (2S, (CH$_3$)$_2$C).

EXAMPLE 2

7-[2-(2-amino 4-thiazolyl)2-(2-carboxy 2-propyl oxyimino)acetamido](3-amino propionyl)3-thiomethyl 3-cepheme 4-carboxylic β1-S-oxide acid trifluoracetate syn isomer SR 41884

(a) Tertiobutoxycarbonyl 3-amino thiopropionic acid 1.8 g of tertiobutoxycarbonyl 3-amino propionic acid was solubilized in 50 ml of anhydrous dichloromethane. The triple-neck flask was provided with a calcium chloride trap and cooled in a bath of water and ice. In order, there were added 1.4 ml of triethylamine and 1.3 ml of isobutyl chloroformate. After 20 minutes stirring in the cold, 1.5 ml of triethylamine was added and a light current of hydrogen sulfide was bubbled through for 15 minutes. then the mixture was stirred in the cold for 45 minutes before being evaporated to dryness. 150 ml of sulfate buffer (pH 2) were added and the thioacid was extracted twice with 70 ml of dichloromethane. The combined organic phases were dried over magnesium sulfate and evaporated.

The oily product obtained was used as such.

(b) 7-[2-(2-tritylamino 4-thiazolyl)2-(2-tertiobutoxycarbonyl 2-propyl oxyimino)acetamido](3-tertiobutoxycarboxylamino propionyl)3-thiomethyl 3-cepheme 1β-S-oxide carboxylate of 4-Tertiobutyl; syn isomer To a solution of 0.46 g of 4-Tertiobutyl 1β-S-oxide 7-[2-(2-tritylamino 4-thiazolyl)2-(2-tertiobutyoxycarbonyl 2-propyl oxyimino)acetamido]3-bromomethyl 3-cepheme carboxylate syn isomer, in 10 ml of tetrahydrofurane, were added 0.4 g of the thioacid described above as well as 0.6 g of potassium bicarbonate. After 4 hours stirring at ambiant temperature the solvent was evaporated and the residue taken up again with 100 ml of water and 50 ml of dichloromethane. After decantation the aqueous phase was extracted with 50 ml of dichloromethane. The organic phases were combined, dried over magnesium sulfate and evaporated.

The lacquer so obtained was chromatographed on a column of silica (40 g), it was eluted with a mixture of dichloromethane-ethyl acetate 90-10 (vol/vol).

IR Spectrum: ∂ CO 1805 cm: C═O at 8 of the β lactame; 1720 cm: C═O of the tertiobutylic esters; 1690 cm: C═O of the amide at 7, of the thioester at 3 and of the tertiobutoxy carbonyl protecting the amine.

NMR Spectrum at 250 MHz (CDCL₃). 1H at 7.75 ppm (D, J=9 Hz, CONH)—15H at 7.27 ppm (M, H ar Trit)—1H at 6.95 ppm (S.e., NH—Trit)—1H at 6.63 ppm (S, H thiazole)—1H at 6.21 ppm (D of D, J₁=9 Hz, J₂=4 Hz, H₇)—1H at 4.85 ppm (S.e., NH—Boc)—1H at 4.50 ppm (D, J=4 Hz, H₆)—1H at 4.29 ppm (D, J=13 Hz, CH₂SCO)—1H at 3.75 ppm (D, J=13 Hz, CH₂SCO)—1H at 3.58 ppm (A of AB, J=17 Hz, CH₂SO)—2H at 3.36 ppm (M, CH₂NH Boc)—1H at 3.22 ppm (B of AB, J=17 Hz, CH₂SO)—2H at 2.75 ppm (T, J=6 Hz, CH₂—CS)—15H at 1.52 ppm (S, Boc NH and (CH₃)₂C)—18H at 1.39 ppm (2S, CO₂tBu).

(c) SR 41 884

The whole of the compound obtained above was solubilized in 10 ml of trifluoroacetic acid. After 45 minutes at 23° C. the acid was evaporated under vacuum without heating, and the oily residue was crystallized by the addition of 50 ml of isopropyl ether. The crystals were filtered and washed with isopropyl ether and then with hexane. They were then dried under vacuum over phosphoric anhydride.

0.37 g of the expected product was obtained.

IR Spectrum: ∂ CO 1785 cm⁻¹: C═O at 8 of the β lactam 1680 cm⁻¹ wide band: C═O of the acids of the molecule, of the amide at 7, of the thioester, of the CF₃CO₂⁻ ions.

NMR Spectrum at 250 MHz. 1H at 8.40 ppm (D, J=9 Hz, CONH)—3H at 7.80 ppm (S.e., NH₃⁺)—3H at 7.30 ppm (S.e., NH₃⁺)—1H at 6.78 ppm (S, H, thiazole)—1H at 5.95 ppm (D of D, J₁=9 Hz, J₂=4 Hz, H₇)—1H at 4.92 ppm (D, J=4 Hz, H₆)—1H at 4.18 ppm (D, J=13 Hz, CH₂SCO)—1H at 3.79 ppm (D, J=13 Hz, CH₂SCO)—2H at 3.66 ppm (S, CH₂SO)—2H at 3.0 ppm (M, CH₂NH)—2H at 2.92 ppm (M, CH₂COS-)—6H at 1.44 ppm (S, (CH₃)₂C).

EXAMPLE 3

Trifluoroacetate of 7-[2-(2-amino 4-thiazoyl)2-(2-carboxy 2-propyl oxyimino)acetamido](3-amino propionyl)3-thiomethyl 3-cepheme 4-carboxylic 1β-S-oxide acid; syn isomer, SR 41884

(a) 7-[2-(2-tritylamino 4-thiazolyl)2-tertiobutoxy 2-(carbonyl 2-propyl oxyimino)acetamido](3-tertiobutoxy carbonylamino)3-thiomethyl 3-cepheme 1β-S-oxide carboxylate of 4-Tertiobutyl; syn isomer To 0.46 g of 4-Tertiobutyl 1β-S-oxide 7-[2-(2-tritylamino 4-thiazolyl)2-(2-tertiobutoxy carboxylamino 2-propyl oxyimino)acetamido]3-bromomethyl 3-cepheme carboxylate syn isomer in 10 ml of anhydrous acetone, were added 0.4 g of 3-tertiobutoxycarvonylamino thiopropionic acid, 0.6 g of potassium bicarbonate and 0.25 g of sodium iodide.

After 2 hours stirring at room temperature, the solvent was evaporated to dryness. The residue was taken up again in 100 ml of water and extracted with 50 ml of dichloromethane. The organic phase is separated and the aqueous phase reextracted with 50 ml of dichloromethane. The organic extracts were combined, dried over magnesium sulfate and evaporated to dryness.

The product obtained was chromatographed on a silica column by eluting with a dichloromethane-ethyl acetate mixture 90-10 (vol/vol).

An identical product (IR spectrum and NMR spectrum) to the product of Example 2(b) was obtained.

(b) SR 41 884

The deprotection was carried out as indicated in Example 2(c).

By operating as in Example 1, the compounds according to the invention were prepared in the form of trifluoroacetate, described in Table I below.

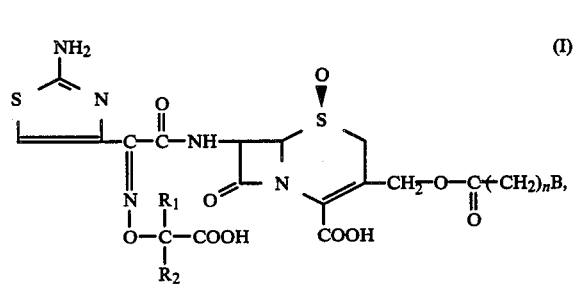

These compounds are identified by a reference number. For each among them the values of R₁, R₂, B and n and the NMR spectrum are given.

The acid B'—(CH₂)ₙ—COOH which reacts on (IV) to give (V) is an aminoacid of the L series or of the D series or racemic; the corresponding indication appears in Table I, at column B.

The chromatographic eluant is also given which serves to isolate (V): the last intermediate product before deblocking the acid and amine functions of the molecule. This intermediate V is characterized by its infra-red spectrum, the wavelengths indicated in cm⁻¹ correspond in order to the elongation vibration frequencies of the carbonyl at the 8 position of the beta lactam, the tertiobutylic esters and the ester at the 3 position, the amide at the 7 position and the carbamate protecting the amine. When 2 wavelengths only are indicated, the second corresponds to a wide band which covers the elongation vibration frequencies both of the esters, of the amide and of the protective carbamate of the amine.

The list of NMR spectra of the compounds mentioned in Table I is given following this table.

TABLEAU I

| SR no. | n | $-C\begin{subarray}{c}R_1\\R_2\end{subarray}$ | B | Chromatography eluant from intermediate V | vol/vol | IR $\delta CO\ cm^{-1}$ intermediate V | NMR no. |
|---|---|---|---|---|---|---|---|
| 41 730 | 0 | $CH_3$, $CH_3$ (isopropyl) | $(CH_2)_2NH_2$ | $CH_2Cl_2$<br>AcOEt | 85<br>15 | 1805<br>1725<br>1690 | 1 |
| 41 731 | " | " | $-CH(NH_2)-CH_2-C_6H_5$ (L) | $CH_2Cl_2$<br>AcOEt | 92.5<br>7.5 | 1805<br>1720 | 2 |
| 41 732 | " | " | $-CH(NH_2)-CH_2-C_6H_4-OH$ (L) | $CH_2Cl_2$<br>AcOEt | 90<br>10 | 1805<br>1725 | 3 |
| 41 733 | " | " | $-CH(NH_2)-CH_3$ (L) | $CH_2Cl_2$<br>AcOEt | 90<br>10 | 1805<br>1725 | 4 |
| 41 806 | " | " | $-CH(NH_2)-CH(CH_3)_2$ (L) | $CH_2Cl_2$<br>AcOEt | 95<br>5 | 1805<br>1730 | 5 |
| 41 807 | " | " | $-CH(NH_2)-CH_3-CH_2-CO-NH_2$ (L) | $CH_2Cl_2$<br>AcOEt | 50<br>50 | 1805<br>1735<br>1680 | 6 |
| 41 810 | " | " | $-CH(NH_2)-CH_2OH$ (L) | $CH_2Cl_2$<br>AcOEt | 80<br>20 | 1805<br>1725 | 7 |
| 41 854 | " | " | $-(CH_2)_3NH_2$ | $CH_2Cl_2$<br>AcOEt | 90<br>10 | 1805<br>1725 | 8 |
| 41 855 | " | " | $-(CH_2)_5NH_2$ | $CH_2Cl_2$<br>AcOEt | 90<br>10 | 1805<br>1725<br>1690 | 9 |
| 41 856 | " | " | $-(CH_2)_7NH_2$ | $CH_2Cl_2$<br>AcOEt | 90<br>10 | 1805<br>1725<br>1695 | 10 |
| 41 857 | " | " | $-CH(NH_2)-CH_2S-CH_2NHCOCH_3$ (L) | $CH_2Cl_2$<br>MeOH | 100<br>1.5 | 1805<br>1725<br>1680 | 11 |
| 41 858 | " | " | $-C(CH_3)_2-NH_2$ | $CH_2Cl_2$<br>AcOEt | 90<br>10 | 1805<br>1725 | 12 |
| 41 859 | " | " | $-CH(NH_2)-CH_2-CH(CH_3)-CH_3$ (L) | $CH_2Cl_2$<br>AcOEt | 92.5<br>7.5 | 1810<br>1725 | 13 |
| 41 860 | " | " | $-CH(NH_2)-CH(CH_3)-CH_2CH_3$ (L) | $CH_2Cl_2$<br>AcOEt | 92.5<br>7.5 | 1805<br>1725 | 14 |
| 41 885 | " | " | $-CH(NH_2)-CH(OH)-CH_3$ (L) | $CH_2Cl_2$<br>AcOEt | 85<br>15 | 1805<br>1720 | 15 |

TABLEAU I-continued

| SR no. | n | $\begin{array}{c}R_1\\-C\\R_2\end{array}$ | B | Chromatography eluant from intermediate V vol/vol | | IR $\delta CO$ cm$^{-1}$ intermediate V | NMR no. |
|---|---|---|---|---|---|---|---|
| 41 886 | " | " | —CH—NH$_2$ (L)<br>CH$_2$CONH$_2$ | CH$_2$Cl$_2$<br>MeOH | 100<br>1.5 | 1805<br>1720<br>1680 | 16 |
| 41 887 | " | " | —CH—NH$_2$ (L)<br>CH$_2$—CH$_2$SCH$_3$ | CH$_2$Cl$_2$<br>AcOEt | 95<br>5 | 1805<br>1725 | 17 |
| 41 888 | " | " | —CH—NH$_2$ (L)<br>(CH$_2$)$_4$—NH$_2$ | CH$_2$Cl$_2$<br>MeOH | 100<br>1 | 1805<br>1720 | 18 |
| 41 889 | " | " |  | CH$_2$Cl$_2$<br>AcOEt | 80<br>20 | 1805<br>1755<br>1720 | 19 |
| 41 891 | " | " | —CH—NH$_2$ (D)<br>CH$_3$ | CH$_2$Cl$_2$<br>AcOEt | 90<br>10 | 1805<br>1725 | 20 |
| 41 967 | " | " | (CH$_2$)$_4$NH$_2$ | CH$_2$Cl$_2$<br>AcOEt | 90<br>10 | 1805<br>1725<br>1690 | 21 |
| 41 975 | " | " |  | CH$_2$Cl$_2$<br>AcOEt | 92.5<br>7.5 | 1805<br>1725 | 22 |
| 41 976 | " | " | 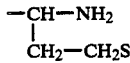 | CH$_2$Cl$_2$<br>AcOEt | 92.5<br>7.5 | 1805<br>1730 | 23 |
| 41 977 | " | " | 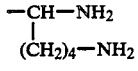 | CH$_2$Cl$_2$<br>AcOEt | 90<br>10 | 1805<br>1720 | 24 |
| 41 987 | " | " | —CH—CH$_2$CH$_2$NH$_2$<br>NH$_2$ (L) | CH$_2$Cl$_2$<br>AcOEt | 85<br>15 | 1805<br>1720 | 25 |
| 42 022 | " | " | 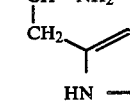 | CH$_2$Cl$_2$<br>AcOEt | 90<br>10 | 1805<br>1730<br>1690 | 26 |
| 42 023 | " | " | —CH—(CH$_2$)$_3$NH$_2$<br>NH$_2$ (L) | CH$_2$Cl$_2$<br>AcOEt | 90<br>10 | 1805<br>1720 | 27 |
| 42 024 | " | " | —CH$_2$—CH—NH$_2$<br>CH$_3$ (R) | CH$_2$Cl$_2$<br>AcOEt | 85<br>15 | 1805<br>1730<br>1690 | 28 |
| 42 025 | " | " | —CH—CH$_2$NH$_2$<br>CH$_3$ (R) | CH$_2$Cl$_2$<br>AcOEt | 90<br>10 | 1805<br>1725<br>1690 | 29 |

TABLEAU I-continued

| SR no. | n | $-C\begin{smallmatrix}R_1\\R_2\end{smallmatrix}$ | B | Chromatography eluant from intermediate V vol/vol | | IR δCO cm$^{-1}$ intermediate V | | NMR no. |
|---|---|---|---|---|---|---|---|---|
| 42 026 | ″ | ″ | —CH$_2$—CH—NH$_2$<br>　　　　　\|<br>　　　　Ph (R) | CH$_2$Cl$_2$<br>AcOEt | 90<br>10 | 1805<br>1725 | | 30 |
| 42 027 | ″ | ″ | —CH$_2$—CH$_2$—CH—NH$_2$<br>　　　　　　　\|<br>　　　　　　CH$_3$ (R) | CH$_2$Cl$_2$<br>AcOEt | 92<br>8 | 1805<br>1730<br>1690 | | 31 |
| 42 028 | ″ | ″ | —(CH$_2$)$_3$NHCH$_3$ | CH$_2$Cl$_2$<br>AcOEt | 90<br>10 | 1805<br>1730<br>1690 | | 32 |
| 42 029 | ″ | ″ | —(CH$_2$)$_4$NHCH$_3$ | CH$_2$Cl$_2$<br>AcOEt | 90<br>10 | 1805<br>1730<br>1690 | | 33 |
| 42 031 | ″ | ″ | —CH—NH$_2$<br>　\|<br>　CH—OH<br>　\|<br>　CH$_3$ (D) | CH$_2$Cl$_2$<br>AcOEt | 85<br>15 | 1805<br>1725<br>1675 | | 34 |
| 42 042 | ″ | ″ | —C$_6$H$_4$—CH$_2$NH$_2$ | CH$_2$Cl$_2$<br>AcOEt | 90<br>10 | 1810<br>1730<br>1690 | CCl$_4$ | 35 |
| 42 073 | ″ | ″ | 　　CH$_3$<br>　　\|<br>—C—CH$_2$NH$_2$<br>　　\|<br>　　CH$_3$ | CH$_2$Cl$_2$<br>AcOEt | 90<br>10 | 1805<br>1725<br>1690 | | 36 |
| 42 117 | ″ | ″ | cyclohexyl-CH$_2$NH$_2$ | CH$_2$Cl$_2$<br>MeOH | 100<br>1 | 1810<br>1725<br>1685 | CCl$_4$ | 37 |
| 42 120 | ″ | ″ | cyclohexyl-NH$_2$ (R) | CH$_2$Cl$_2$<br>AcOEt | 90<br>10 | 1805<br>1725 | | 38 |
| 42 121 | ″ | ″ | —CH—CH$_2$CH$_2$NH$_2$<br>　\|<br>　CH$_3$ (R) | CH$_2$Cl$_2$<br>AcOEt | 90<br>10 | 1805<br>1725<br>1690 | | 39 |
| 42 139 | ″ | ″ | —CH—NH$_2$<br>　\|<br>　CH—CH$_3$<br>　\|<br>　CH$_3$ (D) | CH$_2$Cl$_2$<br>AcOEt | 95<br>5 | 1805<br>1725<br>1690 | | 40 |
| 42 140 | ″ | ″ | —CH$_2$CH$_2$NHCH$_3$ | CH$_2$Cl$_2$<br>AcOEt | 90<br>10 | 1805<br>1730<br>1690 | | 41 |
| 42 181 | ″ | ″ | —(CH$_2$)$_3$NHCH$_2$CH$_3$ | CH$_2$Cl$_2$<br>MeOH | 100<br>1 | 1805<br>1730<br>1685 | CH$_2$Cl$_2$ | 42 |
| 42 182 | ″ | ″ | —CH$_2$—CH$_2$—CH—NHCH$_3$<br>　　　　　　　\|<br>　　　　　　CH$_3$ (R) | CH$_2$Cl$_2$<br>AcOEt | 90<br>10 | 1805<br>1735<br>1685 | | 43 |
| 42 183 | ″ | ″ | —(CH$_2$)$_5$NHCH$_3$ | CH$_2$Cl$_2$ | 100 | 1810<br>1735 | | 44 |

TABLEAU I-continued

| SR no. | n | -C(R1)(R2) | B | Chromatography eluant from intermediate V vol/vol | | IR δCO cm⁻¹ intermediate V | | NMR no. |
|---|---|---|---|---|---|---|---|---|
| | | | | MeOH | 1 | 1690 | CCl₄ | |
| 42 191 | " | —CH₂ |  | CH₂Cl₂<br>AcOEt | 85<br>15 | 1805<br>1730<br>1690 | | 45 |
| 42 192 | " | 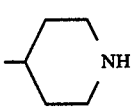 |  | CH₂Cl₂<br>AcOEt | 90<br>10 | 1805<br>1730<br>1690 | | 46 |
| 42 193 | " | —CH₂ | 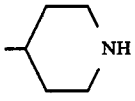—CH₂NH₂ | CH₂Cl₂<br>AcOEt | 90<br>10 | 1805<br>1720 | | 47 |
| 42 194 | " | 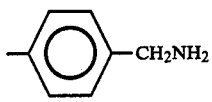 | —CH₂NH₂ | CH₂Cl₂<br>AcOEt | 90<br>10 | 1805<br>1725 | | 48 |
| 42 195 | " | —CH₂ | —(CH₂)₃NH₂ | CH₂Cl₂<br>AcOEt | 85<br>15 | 1805<br>1730<br>1690 | | 49 |
| 42 196 | " | 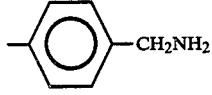 | " | CH₂Cl₂<br>AcOEt | 90<br>10 | 1805<br>1725<br>1695 | | 50 |
| 42 197 | " | —CH₂ | —(CH₂)₄NH₂ | CH₂Cl₂<br>AcOEt | 85<br>15 | 1805<br>1725<br>1690 | | 51 |
| 42 198 | " |  | " | CH₂Cl₂<br>AcOEt | 90<br>10 | 1805<br>1725<br>1695 | | 52 |
| 42 200 | " | " | —CH(CH₃)—NH₂  (D) | CH₂Cl₂<br>AcOEt | 90<br>10 | 1805<br>1725 | | 53 |
| 42 201 | " | " | —CH(CH₃)—CH₂NH₂  (R) | CH₂Cl₂<br>AcOEt | 90 | 1805<br>1725<br>1690 | | 54 |
| 42 208 | " | " | —C(CH₃)₂—CH₂NH₂ | CH₂Cl₂<br>AcOEt | 92.5<br>7.5 | 1805<br>1725 | | 55 |
| 42 209 | " | " | —CH(CH₃)—CH₂CH₂NH₂  (R) | CH₂Cl₂<br>AcOEt | 90<br>10 | 1805<br>1725<br>1690 | | 56 |
| 42 210 | " | " |  | CH₂Cl₂<br>AcOEt | 92.5<br>7.5 | 1805<br>1725 | | 57 |
| 42 211 | " | —CH₂ | 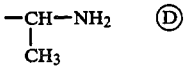····CH₂NH₂ | CH₂Cl₂<br>AcOEt | 85 | 1805<br>1725<br>1690 | | 58 |
| 42 212 | " | 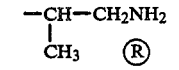 | " | CH₂Cl₂<br>AcOEt | 90<br>10 | 1805<br>1725<br>1690 | | 59 |

TABLEAU I-continued

| SR no. | n | -C(R1)(R2) | B | Chromatography eluant from intermediate V vol/vol | | IR δCO cm⁻¹ intermediate V | NMR no. |
|---|---|---|---|---|---|---|---|
| 42 213 | " | −CH(CH₃) | −(CH₂)₃NH₂ | CH₂Cl₂ AcOEt | 85 15 | 1805 1730 1690 | 60 |
| 42 214 | " | " | −(CH₂)₄NH₂ | CH₂Cl₂ AcOEt | 85 15 | 1805 1730 1690 | 61 |
| 42 215 | " | " | 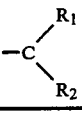 (piperidine-NH) | CH₂Cl₂ AcOEt | 90 10 | 1805 1735 1690 | 62 |
| 42 216 | " | −CH(CH₃) |  (−C₆H₄−CH₂NH₂) | CH₂Cl₂ AcOEt | 90 10 | 1805 1725 CCl₄ | 63 |
| 42 217 | " | " | 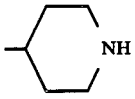 (trans-cyclohexyl-CH₂NH₂) | CH₂Cl₂ AcOEt | 90 10 | 1810 1725 1690 | 64 |
| 42 320 | " | −C(CH₃)₂ | 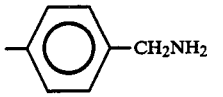 (−C₆H₄−CH₂NH₂) | CH₂Cl₂ AcOEt | 95 5 | 1805 1725 | 65 |
| 42 321 | " | " | 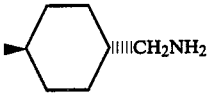 (cyclohexyl-CH₂NH₂) | CH₂Cl₂ MeOH | 100 1 | 1805 1730 1690 | 66 |
| 42 371 | 1 | " | 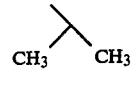 (piperidine-NH) | CH₂Cl₂ MeOH | 100 0.7 | | 67 |
| 42 372 | " | " | 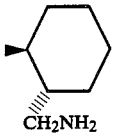 (piperidine-NH) | CH₂Cl₂ MeOH | 100 0.7 | | 68 |
| 42 374 | 0 | " | 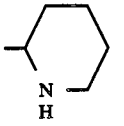 (−C₆H₄−NHCOCH₂NH₂) | CH₂Cl₂ MeOH | 100 1 | 1805 1725 1690 | 69 |
| 42 379 | " | " | 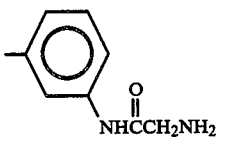 (−C₆H₄(CH₃)−CH₂NH₂) | CH₂Cl₂ AcOEt | 90 10 | 1805 1725 | 70 |

TABLEAU I-continued

| SR no. | n | $\begin{array}{c}R_1\\-C-\\R_2\end{array}$ | B | Chromatography eluant from intermediate V vol/vol | | IR $\delta CO$ cm$^{-1}$ intermediate V | NMR no. |
|---|---|---|---|---|---|---|---|
| 42 380 | " | " |  | CH$_2$Cl$_2$<br>AcOEt | 95<br>5 | 1805<br>1725 | 71 |
| 42 395 | " | " | 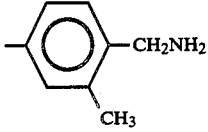 | CH$_2$Cl$_2$<br>AcOEt | 90<br>10 | 1805<br>1725<br>1685 | 72 |
| 42 396 | " | " | 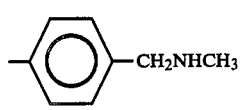 | CH$_2$Cl$_2$<br>MeOH | 100<br>0.6 | 1805<br>1725<br>1685 | 73 |
| 42 397 | " | " | 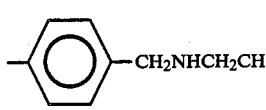 | CH$_2$Cl$_2$<br>AcOEt | 90<br>10 | 1805<br>1725<br>1685 | 74 |
| 42 456 | " | " | 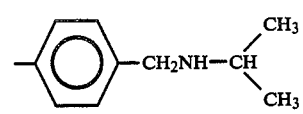 | CH$_2$Cl$_2$<br>AcOEt | 95<br>5 | | 75 |
| 42 457 | " | " | 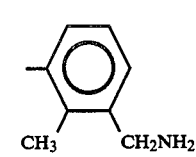 | CH$_2$Cl$_2$<br>MeOH | 100<br>1 | 1805<br>1725 | 76 |
| 42 458 | " | " | 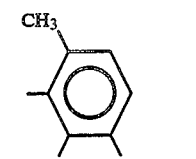 | CH$_2$Cl$_2$<br>AcOEt | 95<br>5 | 1805<br>1725 | 77 |
| 42 459 | " | " | 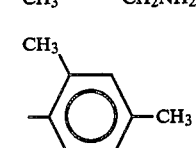 | CH$_2$Cl$_2$<br>AcOEt | 85<br>15 | | 78 |
| 42 460 | " | " | 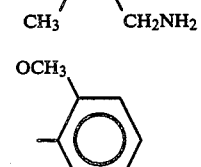 | CH$_2$Cl$_2$<br>MeOH | 100<br>1 | 1805<br>1720 | 79 |
| 42 461 | " | " | 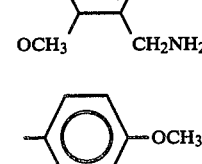 | CH$_2$Cl$_2$<br>MeOH | 100<br>1 | 1802<br>1720 | 80 |

TABLEAU I-continued

| SR no. | n | -C(R1)(R2) | B | Chromatography eluant from intermediate V vol/vol | | IR δCO cm$^{-1}$ intermediate V | NMR no. |
|---|---|---|---|---|---|---|---|
| 42 462 | " | cyclobutyl | phenyl-CH$_2$NH$_2$ | CH$_2$Cl$_2$ MeOH | 100 1 | 1805 1720 | 81 |
| 42 463 | " | " | CH$_3$-phenyl-CH$_2$NH$_2$ | CH$_2$Cl$_2$ MeOH | 100 1 | 1805 1720 | 82 |
| 42 464 | " | " | phenyl-CH$_2$NHCH$_3$ | CH$_2$Cl$_2$ MeOH | 100 1 | 1805 1720 1690 | 83 |
| 42 465 | " | CH$_3$, CH$_3$ | phenyl-NHC(O)(CH$_2$)$_2$NH$_2$ | CH$_2$Cl$_2$ MeOH | 100 1.5 | 1805 1725 1690 | 84 |
| 42 466 | " | " | thiazolyl-NHCCH$_2$NH$_2$ | CH$_2$Cl$_2$ MeOH | 100 1.5 | 1805 1720 | 85 |
| 42 467 | " | " | phenyl-NHCCH$_2$NH$_2$ | CH$_2$Cl$_2$ MeOH | 100 2 | 1805 1720 | 86 |
| 42 471 | 1 | cyclobutyl | piperidine-NH | CH$_2$Cl$_2$ MeOH | 100 0.5 | 1805 CCl$_4$ 1720 1675 | 87 |
| 42 472 | " | " | piperidine-NH | CH$_2$Cl$_2$ AcOEt | 95 5 | 1805 CCl$_4$ 1725 1675 | 88 |
| 42 473 | " | " | piperidine-NH | CH$_2$Cl$_2$ MeOH | 100 0.5 | 1805 CCl$_4$ 1725 1685 | 89 |
| 42 474 | " | CH$_3$, CH$_3$ | piperidine-NH | CH$_2$Cl$_2$ AcOEt | 95 5 | 1805 CCl$_4$ 1725 1685 | 90 |
| 42 537 | 0 | " | phenyl-CH$_2$NHCH$_3$ | CH$_2$Cl$_2$ MeOH | 100 1 | 1805 1725 1690 | 91 |

TABLEAU I-continued

| SR no. | n | -C(R₁)(R₂) | B | Chromatography eluant from intermediate V vol/vol | | IR δCO cm⁻¹ intermediate V | NMR no. |
|---|---|---|---|---|---|---|---|
| 42 538 | " | " | 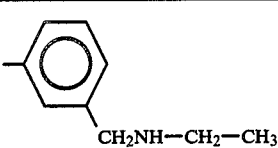 —⟨C₆H₄⟩—CH₂NH—CH₂—CH₃ | CH₂Cl₂<br>MeOH | 100<br>1 | 1805<br>1725<br>1690 | 92 |
| 42 539 | " | " | 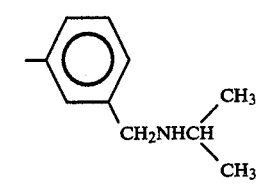 —⟨C₆H₄⟩—CH₂NHCH(CH₃)₂ | CH₂Cl₂<br>MeOH | 100<br>0.8 | 1805<br>1725<br>1685 | 93 |
| 42 540 | " |  | 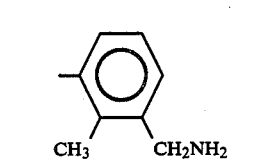 CH₃ / CH₂NH₂ substituted phenyl | CH₂Cl₂<br>MeOH | 100<br>0.7 | 1805<br>1720 | 94 |
| 42 541 | " | " | CH₃ / CH₃ / CH₂NH₂ substituted phenyl 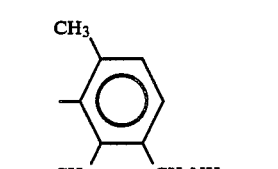 | CH₂Cl₂<br>MeOH | 100<br>0.7 | 1805<br>1720 | 95 |
| 42 542 | " | " | CH₃ / CH₃ / CH₃ / CH₂NH₂ substituted phenyl 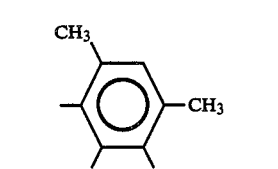 | CH₂Cl₂<br>MeOH | 100<br>0.5 | 1805<br>1720 | 96 |
| 42 544 | " | CH₃—CH—CH₃ 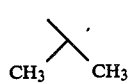 | 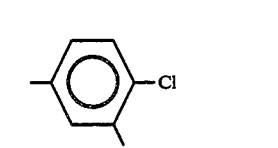 —⟨C₆H₃⟩(Cl)—NHCOCH₂NH₂ | CH₂Cl₂<br>MeOH | 100<br>1 | 1802<br>1720 | 97 |
| 42 545 | " | " | 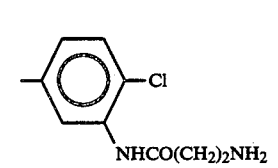 —⟨C₆H₃⟩(Cl)—NHCO(CH₂)₂NH₂ | CH₂Cl₂<br>MeOH | 100<br>1 | 1803<br>1720 | 98 |
| 42 546 | " | " | 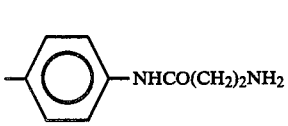 —⟨C₆H₄⟩—NHCO(CH₂)₂NH₂ | CH₂Cl₂<br>MeOH | 100<br>1 | 1805<br>1720 | 99 |
| 42 547 | |  | 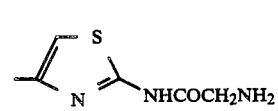 thiazole—NHCOCH₂NH₂ | CH₂Cl₂<br>MeOH | 100<br>1.5 | 1805<br>1720 | 100 |
| 42 548 | " | " | 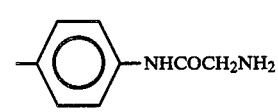 —⟨C₆H₄⟩—NHCOCH₂NH₂ | CH₂Cl₂<br>MeOH | 100<br>2 | 1802<br>1720 | 101 |

TABLEAU I-continued

| SR no. | n | $-C\begin{smallmatrix}R_1\\R_2\end{smallmatrix}$ | B | Chromatography eluant from intermediate V vol/vol | | IR $\delta CO$ cm$^{-1}$ intermediate V | NMR no. |
|---|---|---|---|---|---|---|---|
| 42 549 | " | CH₃, CH₃ (isopropyl) | piperidine-N-CO-CH₂-NH₂ | CH₂Cl₂ MeOH | 100 1 | 1805 1720 | 102 |
| 42 581 | " | " | 2-F-phenyl-CH₂NH₂ | CH₂Cl₂ MeOH | 100 0.8 | 1805 1725 | 103 |
| 42 582 | " | " | 2-F-phenyl-CH₂NHCH₃ | CH₂Cl₂ MeOH | 100 0.8 | 1805 1725 1690 | 104 |
| 42 583 | " | " | phenyl-NHCOCH₂NHCH₃ | CH₂Cl₂ MeOH | 100 0.5 | 1805 1720 1685 | 105 |
| 42 584 | " | " | phenyl-NHCOCH₂NHCH₃ | CH₂Cl₂ MeOH | 100 1 | 1802 1720 | 106 |
| 42 585 | " | " | 2-CH₃-phenyl-NHCOCH₂NH₂ | CH₂Cl₂ MeOH | 100 0.8 | 1805 1720 1690 | 107 |
| 42 586 | " | " | 2-CH₃-phenyl-NHCO(CH₂)₂NH₂ | CH₂Cl₂ MeOH | 100 1 | 1805 1725 1690 | 108 |
| 42 587 | " | " | thiazolyl-NHCO(CH₂)₂NH₂ | CH₂Cl₂ MeOH | 100 1.5 | 1805 1720 1690 | 109 |
| 42 657 | " | " | phenyl-N(CH₃)COCH₂NH₂ | CH₂Cl₂ MeOH | 100 0.7 | 1805 1725 1675 | 110 |
| 42 658 | " | cyclobutyl | phenyl-NHCO(CH₂)₂NH₂ | CH₂Cl₂ MeOH | 100 1 | 1805 1720 | 111 |
| 42 675 | " | " | piperidine-N-CO-CH₂NH₂ | CH₂Cl₂ AcOEt | 90 10 | 1805 1725 | 112 |

TABLEAU I-continued

| SR no. | n | $-C{\genfrac{}{}{0pt}{}{R_1}{R_2}}$ | B | Chromatography eluant from intermediate V vol/vol | | IR $\delta CO$ cm$^{-1}$ intermediate V | NMR no. |
|---|---|---|---|---|---|---|---|
| 42 676 | " | $-C(CH_3)_2$ (iPr: CH₃, CH₃) | 2-Br, 4-yl benzyl-CH₂NH₂ (2-bromo-4-substituted benzyl amine) | CH₂Cl₂ MeOH | 100 0.5 | 1805 1720 | 113 |
| 42 677 | " | " | 2-CH₂NH₂, 4-yl, with Br (phenyl with CH₂NH₂ ortho and Br) | CH₂Cl₂ MeOH | 100 0.5 | 1805 1720 | 114 |
| 42 687 | " | " | phenyl-NHCO(CH₂)₃NH₂ (meta) | CH₂Cl₂ MeOH | 100 0.9 | 1805 1725 1690 | 115 |
| 42 688 | " | " | phenyl-NHCO(CH₂)₃NH₂ (para) | CH₂Cl₂ MeOH | 100 0.8 | 1805 1720 | 116 |
| 42 689 | " | " | phenyl-NHCO(CH₂)₄NH₂ | CH₂Cl₂ MeOH | 100 0.8 | 1805 1720 | 117 |
| 42 690 | " | " | 4-methylthiazol-2-yl-NHCOCH₂NH₂ | CH₂Cl₂ MeOH | 100 1 | 1805 1715 | 118 |
| 42 811 | " | " | cyclohexyl-NH₂ (Cis Trans) | CH₂Cl₂ MeOH | 100 0.5 | 1805 CH₂Cl₂ 1725 | 119 |
| 42 812 | " | " | phenyl-CH(CH₃)CH₂NH₂ | CH₂Cl₂ AcOEt | 92.5 7.5 | 1805 1725 | 120 |
| 42 814 | " | " | 2,6-dimethylphenyl-NHCOCH₂NH₂ | CH₂Cl₂ MeOH | 100 1 | 1805 1725 1690 | 121 |
| 42 815 | " | " | phenyl-NHCO-piperidin-4-yl NH | CH₂Cl₂ MeOH | 100 0.7 | 1805 1725 1690 | 122 |

TABLEAU I-continued

| SR no. | n | -C(R1)(R2) | B | Chromatography eluant from intermediate V vol/vol | | IR δCO cm⁻¹ intermediate V | | NMR no. |
|---|---|---|---|---|---|---|---|---|
| 42 816 | " | " |  | CH₂Cl₂<br>MeOH | 100<br>0.7 | 1805<br>1725<br>1690 | | 123 |
| 42 817 | " | " | 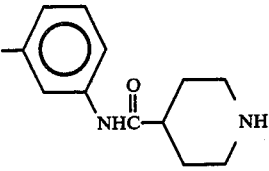 | CH₂Cl₂<br>MeOH | 100<br>0.9 | 1805<br>1720 | | 124 |
| 42 818 | " | 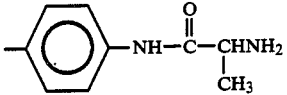 | " | CH₂Cl₂<br>MeOH | 100<br>0.9 | 1805<br>1720 | | 125 |
| 42 781 | " | CH₃ CH₃ | 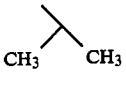 | CH₂Cl₂<br>MeOH | 100<br>1 | 1805<br>1725<br>1675 | CH₂Cl₂ | 126 |
| 42 782 | " | " | 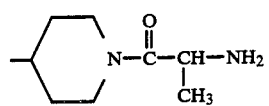 | CH₂Cl₂<br>MeOH | 100<br>1.5 | 1805<br>1725 | | 127 |
| 42 783 | " | " | 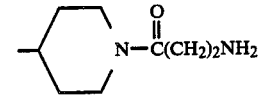 | CH₂Cl₂<br>MeOH | 100<br>1 | | | 128 |
| 42 846 | " | " | 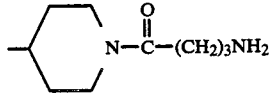 | CH₂Cl₂<br>MeOH | 100<br>1 | 1805<br>1725<br>1680 | CH₂Cl₂ | 129 |
| 42 848 | " | " | 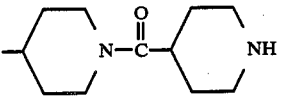 | CH₂Cl₂<br>MeOH | 100<br>0.7 | 1805<br>1720 | | 130 |
| 42 849 | " | 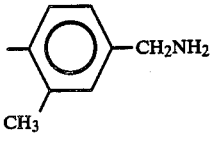 |  | CH₂Cl₂<br>MeOH | 100<br>0.7 | 1805<br>1720 | | 131 |
| 42 852 | " | 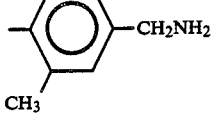CH₃ CH₃ | 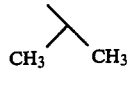 | CH₂Cl₂<br>MeOH | 100<br>0.5 | 1805<br>1725 | | 132 |
| 42 857 | " | " | 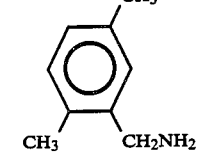 | CH₂Cl₂<br>MeOH | 100<br>1.5 | 1805<br>1725 | | 133 |

TABLEAU I-continued

| SR no. | n | $R_1$ $R_2$ (—C⟨) | B | Chromatography eluant from intermediate V vol/vol | | IR $\delta CO\ cm^{-1}$ intermediate V | NMR no. |
|---|---|---|---|---|---|---|---|
| 42 862 | " | " |  | CH$_2$Cl$_2$<br>MeOH | 100<br>1 | 1805<br>1725 | 134 |
| 42 869 | " | " | 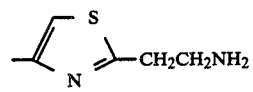 | CH$_2$Cl$_2$<br>AcOEt | 85<br>15 | 1805<br>1725 | 135 |
| 42 870 | " | 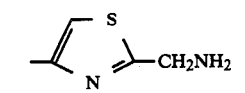 |  | CH$_2$Cl$_2$<br>AcOEt | 80<br>20 | 1805<br>1720 | 136 |
| 42 901 | " | 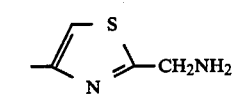 |  | CH$_2$Cl$_2$<br>MeOH | 100<br>1 | 1805<br>1720<br>1680 | 137 |

NMR SPECTRA: The spectra are recorded at 60 MHz, indicated by (a) or at 250 MHz, indicated by (b); when there exist two diastereo-isomers in a molecule, the split signals are indicated by *.

NMR no. 1-(b): 1H at 8.44 ppm (D, J=9 Hz, CONH)—3H at 7.90 ppm (S.e., N+H$_3$)—3H at 7.50 ppm N+H$_3$)—1H at 6.78 ppm (S, H thiazol)—1H at 5.97 ppm (D of D, J$_1$=9 Hz, J$_2$=4 Hz, H$_7$)—1H at 5.18 ppm (D, J=13 Hz, CH$_2$OCO)—1H at 4.94 ppm (D, J=4 Hz, H$_6$)—1H at 4.64 ppm (D, J=13 Hz, CH$_2$OCO)—1H at 3.90 ppm (D, J=17 Hz, CH$_2$SO)—1H at 3.58 ppm (D, J=17 Hz, CH$_2$SO)—2H at 3.00 ppm (M, CH$_2$NH$_2$)—2H at 2.61 ppm (M, CH$_2$CO$_2$)—6H at 1.44 ppm (S, (CH$_3$)$_2$C).

NMR no. 2-(b): 4H at 8.45 ppm (M, N+H$_3$, CONH-)—3H at 7.35 ppm (S.e., N+H$_3$)—5H at 7.25 ppm (M, H aromatics—1H at 6.82 ppm (S, H thiazol)—1H at 6.0 ppm (D of D, J$_1$=9 Hz, J$_2$=4 Hz, H$_7$)—1H at 5.20 ppm (D, J=13 Hz, CH$_2$OCO)—1H at 4.92 ppm (D, J=4 Hz, H$_6$)—1H at 4.81 ppm (D, J=13 Hz, CH$_2$OCO)—1H at 4.31 ppm (S.e., CHNH$_2$)—1H at 3.50 ppm (D, J=17 Hz, CH$_2$SO)—1H at 3.30 ppm (D, J=17 Hz, CH$_2$SO)—2H at 3.10 ppm (M, CH$_2$C$_6$H$_5$)—6H at 1.44 ppm (2S, (CH$_3$)$_2$C).

NMR no. 3-(b): 5H at 8.45 ppm (S.e., N+H$_2$, OH, CONH)—3H at 7.50 ppm (S.e., N+H$_3$)—2H at 6.95 ppm (D, J=8 Hz, H meta OH)—1H at 6.78 ppm (S, H thiazol)—2H at 6.68 ppm (D, J=8 Hz, H ortho OH-)—1H at 6.0 ppm (D of D, J$_1$=9 Hz, J$_2$=4 Hz, H$_7$)—1H at 5.16 ppm (D, J=13 Hz, CH$_2$OCO)—1H at 4.92 ppm (D, J=4 Hz, H$_6$)—1H at 4.74 ppm (D, J=13 Hz, CH$_2$OCO)—1H at 4.19 ppm (M, CHNH$_2$)—1H at 3.66 ppm (D, J=17 Hz, CH$_2$SO)—1H at 3.34 ppm (D, J=17 Hz, CH$_2$SO)—2H at 2.93 ppm (M, CH$_2$—CH—NH-$_2$)—6H at 1.44 ppm (2S, (CH$_3$)$_2$C).

NMR no. 4-(b): 1H at 8.50 ppm (D, J=9 Hz, CONH)—3H at 8.40 ppm (S.e. N+H$_3$)—3H at 7.60 ppm (S.e. N+H$_3$)—1H at 6.79 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 4.97 ppm (D, J=4 Hz, H$_6$)—1H at 4.80 ppm (D, J=13 Hz, CH$_2$OCO)—1H at 4.08 ppm (M, CHNH$_2$)—1H at 3.92 ppm (D, J=17 Hz, CH$_2$SO)—1H at 3.58 ppm (D, J=17 Hz, CH$_2$SO)—6H at 1.44 ppm (S, (CH$_3$)$_2$C)—3H at 1.34 ppm (D, J=7 Hz, CH$_3$CH).

NMR no. 5-(b): 1H at 8.45 ppm (D, J=9 Hz, CONH)—3H at 8.40 ppm (S.e., N+H$_3$)—3H at 7.60 ppm (S.e., N+H$_3$)—1H at 6.78 ppm (S, H thiazol)—1H at 6.0 ppm (D of D, J$_1$=9 Hz, J$_2$=4 Hz, H$_7$)—1H at 5.25 ppm (D, J=13 Hz, CH$_2$OCO)—1H at 4.95 ppm (D, J=4 Hz, H$_6$)—1H at 4.82 ppm (D, J=13 Hz, CH$_2$OCO)—2H at 3.92 ppm (M, CHNH$_2$ and CH$_2$SO)—1H at 3.56 ppm (D, J=17 Hz, CH$_2$SO)—1H at 2.11 ppm (M, CH(CH$_3$)$_2$)—6H at 1.44 ppm (2S, (CH$_3$)$_2$C)—6H at 0.9 ppm (D, J=7 Hz, (CH$_3$)$_2$CH).

NMR no. 6-(b): 1H at 8.45 ppm (D, J=9 Hz, CONH)—3H at 8.35 ppm (S.e., N+H$_3$)—4H at 7.40 ppm (S.e., CONH$_2$, N+H$_3$)—1H at 6.92 ppm (S.e., CONH$_2$)—1H at 6.76 ppm (S, H thiazol)—1H at 6.0 ppm (D of D, J$_1$=9 Hz, J$_2$=4 Hz, H$_7$)—1H at 5.25 ppm (D, J=13 Hz, CH$_2$OCO)—1H at 5.00 ppm (D, J=4 Hz, H$_6$)—1H at 4.82 ppm (D, J=13 Hz, CH$_2$OCO)—1H at 4.00 ppm (M, CHNH$_2$)—1H at 3.95 ppm (D, J=17 Hz, CH$_2$SO)—1H at 3.56 ppm (D, J=17 Hz, CH$_2$SO)—2H at 2.20 ppm (M, CH$_2$—CONH$_2$)—2H at 1.95 ppm (M, CH$_2$—CH)—6H at 1.44 ppm (2S, (CH$_3$)$_2$C).

NMR no. 7-(b): 1H at 8.50 ppm (D, J=9 Hz, CONH-)—3H at 8.40 ppm (S.e., N+H$_3$)—3H at 7.40 ppm (S.e., N+H$_3$)—1H at 6.76 ppm (S, H thiazol)—1H at 6.0 ppm (D of D, J$_1$=9 Hz, J$_2$=4 Hz, H$_7$)—1H at 5.25 ppm (D, J=13 Hz, CH$_2$OCO)—1H at 4.92 ppm (D, J=4 Hz, H$_6$)—1H at 4.82 ppm (D, J=13 Hz, CH$_2$OCO)—1H at 4.16 ppm (M, CHNH$_2$)—1H at 3.95 ppm (D, J=17 Hz, CH$_2$SO)—1H at 3.81 ppm (A of AB, J$_{AB}$=13 Hz, CH$_2$OH)—1H at 3.69 ppm (B of AB, J$_{AB}$=13 Hz, CH$_2$OH)—1H at 3.55 ppm (D, J=17 Hz, CH$_2$SO)—6H at 1.44 ppm (2S, (CH$_3$)$_2$C).

NMR no. 8-(a): 8H between 5.5 and 8.5 ppm (widened signal, NH$_2$, CO$_2$H, TRA)—1H at 8.40 ppm (D, J=9 Hz, CONH)—1H at 6.82 ppm (S, H thiazol)—1H at 6.0 ppm (D of D, J$_1$=9 Hz, J$_2$=4 Hz, H$_7$)—1H at 5.15 ppm (A of AB, J$_{AB}$=13 Hz, CH$_2$OCO)—1H at 5.0 ppm (D, J=4 Hz, H$_6$)—1H at 4.67 ppm (B of AB, J=13 Hz, CH$_2$OCO)—1H at 3.85 ppm (A of AB, J=17 Hz; CH$_2$SO)—1H at 3.62 ppm (B of AB, J=17 Hz, CH$_2$SO)—2H at 2.80 ppm (M, CH$_2$NH$_2$)—2H at 2.40 ppm (M, C$\underline{H_2}$CO$_2$)—2H at 1.80 (M, CH$_2$C$\underline{H_2}$CH$_2$)—6H at 1.43 ppm (S, (C$\underline{H_3}$)$_2$C).

NMR no. 9-(a): 8H between 5.5 and 8.7 ppm (wide signal, CO$_2$H, NH$_2$, TFA)—1H at 8.40 ppm (D, J=9 Hz, CON$\underline{H}$)—1H at 6.87 ppm (S, $\underline{H}$ thiazol)—1H at 6.0 ppm (D of D, J$_1$=9 Hz, J$_2$=4 Hz, $\underline{H_7}$)—1H at 5.15 ppm (A of AB, J=13 Hz, C$\underline{H_2}$OCO)—1H at 5.0 ppm (D, J=4 Hz, H$_6$)—1H at 4.60 ppm (B of AB, J=13 Hz, C$\underline{H_2}$OCO)—1H at 3.85 ppm (A of AB, J=17 Hz, C$\underline{H_2}$SO)—1H at 3.60 ppm (B of AB, J=17 Hz, C$\underline{H_2}$SO)—2H at 2.80 ppm (M, C$\underline{H_2}$NH$_2$)—2H at 2.30 ppm (M, C$\underline{H_2}$CO)—12H at 1.45 ppm (S.e., (C$\underline{H_3}$)$_2$C and CH$_2$(C$\underline{H_2}$)$_3$CH$_2$).

NMR no. 10-(a): 8H between 5.5 and 8.0 ppm (wide signal, NH$_2$, CO$_2$H, TFA)—1H at 8.45 ppm (D, J=9 Hz, CON$\underline{H}$)—1H at 6.87 ppm (S, $\underline{H}$ thiazol)—1H at 6.0 ppm (D of D, J$_1$=9 Hz, J$_2$=4 Hz, $\underline{H_7}$)—1H at 5.15 ppm (A of AB, J=13 Hz, C$\underline{H_2}$OCO)—1H at 5.0 ppm (D, J=4 Hz, H$_6$)—1H at 4.65 ppm (B of AB, J=13 Hz, C$\underline{H_2}$OCO)—1 H at 3.85 ppm (A of AB, J=17 Hz, C$\underline{H_2}$SO)—1H at 3.62 ppm (B of AB, J=17 Hz, C$\underline{H_2}$SO)—2H at 2.80 ppm (M, C$\underline{H_2}$NH$_2$)—2H at 2.30 ppm (M, C$\underline{H_2}$CO$_2$)—6H at 1.45 ppm (S, (C$\underline{H_3}$)$_2$C)—10H at 1.35 ppm (S.e., CH$_2$(C$\underline{H_2}$)$_5$CH$_2$).

NMR no. 11-(a): 2H at 8.40 ppm (M, CON$\underline{H}$, CH$_3$CON$\underline{H}$)—8H at 7.50 ppm (S.e., N$^+$H$_3$, CO$_2$$\underline{H}$)—1H at 6.90 ppm (S, H thiazol)—1H at 6.05 ppm (D of D, J$_1$=9 Hz, J$_2$=4 Hz, $\underline{H_7}$)—1H at 5.40 ppm (A of AB, J=13 Hz, C$\underline{H_2}$OCO)—1H at 4.98 ppm (D, J=4 Hz, H$_6$)—1H at 4.90 ppm (B of AB, J=13 Hz, C$\underline{H_2}$OCO-)—3H at 4.30 ppm (M, C$\underline{H_2}$NHCOCH$_3$, CHN$\underline{H_2}$)—1H at 4.00 ppm (A of AB, J$_{AB}$=17 Hz, C$\underline{H_2}$SO)—1H at 3.65 ppm (B of AB, J$_{AB}$=17 Hz, C$\underline{H_2}$SO)—2H at 3.00 ppm (M, C$\underline{H_2}$S)—3H at 1.80 ppm (S, C$\underline{H_3}$CONH)—6H at 1.45 ppm (S, (C$\underline{H_3}$)$_2$C).

NMR no. 12-(a): 8H between 6.5 and 9 ppm (wide signal, CO$_2$H, TFA, NH$_2$)—1H at 8.5 ppm (D, J=9 Hz, CON$\underline{H}$)—1H at 6.90 ppm (S, $\underline{H}$ thiazol)—1H at 6.0 ppm (D of D, J$_1$=9 Hz, J$_2$=4 Hz, $\underline{H_7}$)—1H at 5.30 ppm (A of AB, J=13 Hz, C$\underline{H_2}$OCO)—1H at 5.0 ppm (D, J=4 Hz, H$_6$)—1H at 4.80 ppm (B of AB, J=13 Hz, C$\underline{H_2}$OCO)—1H at 3.92 ppm (A of AB, J=17 Hz, C$\underline{H_2}$SO)—1H at 3.67 ppm (B of AB, J=17 Hz, C$\underline{H_2}$SO)—12H at 1.45 ppm (S, (C$\underline{H_3}$)$_2$C—CO$_2$H, (C$\underline{H_3}$)$_2$CNH$_2$).

NMR no. 13-(a): 8H between 6.5 and 9.5 ppm (wide signal, CO$_2$H, NH$_2$, TFA)—1H 8.5 ppm (D, J=9 Hz, CON$\underline{H}$)—1$\underline{H}$ at 6.90 ppm (S, $\underline{H}$ thiazol)—1H at 6.05 ppm (D of D, J$_1$=9 Hz, J$_2$=4 Hz, $\underline{H_7}$)—1H at 5.30 ppm (A of AB, J=13 Hz, C$\underline{H_2}$OCO)—1H at 5.05 ppm (D, J=4 Hz, H$_6$)—1H at 4.90 ppm (B of AB, J=13 Hz, C$\underline{H_2}$OCO)—3H at 3.80 ppm (M, CHNH$_2$ and C$\underline{H_2}$SO)—3H at 1.50 ppm (M, C$\underline{H_2}$—CH)—6H at 1.45 ppm (S, (C$\underline{H_3}$)$_2$C)—6H at 0.85 ppm (D, J=7 Hz, (C$\underline{H_3}$)$_2$CH).

NMR no. 14-(a): 8H between 7 and 9 ppm (wide signal, NH$_2$, CO$_2$H, TFA)—1H at 8.50 ppm (D, J=9 Hz, CON$\underline{H}$)—1H at 6.90 ppm (S, $\underline{H}$ thiazol)—1H 6.08 ppm (D of D, J$_1$=9 Hz, J$_2$=4 Hz, $\underline{H_7}$)—1H at 5.30 ppm (A of AB, J$_{AB}$=13 Hz, C$\underline{H_2}$OCO)—1H at 5.05 ppm (D, J=4 Hz, H$_6$) 1H at 4.49 ppm (B of AB, J$_{AB}$=13 Hz, C$\underline{H_2}$OCO)—3H at 3.90 ppm (M, C$\underline{H_2}$SO and C$\underline{H}$CH$_2$) 1H at 1.80 ppm (M, C$\underline{H}$CH$_3$)—6H at 1.45 ppm (S, (C$\underline{H_3}$)$_2$C)—2H at 1.30 ppm (M, C$\underline{H_2}$CH$_3$)—6H at 0.88 ppm (M, C$\underline{H_3}$CH$_2$ and C$\underline{H_3}$CH).

NMR no. 15-(b):
1H at 8.5 ppm (D, J=9 Hz, CON$\underline{H}$)—3H at 8.30 ppm (S.e., N$^+$$\underline{H_3}$)—3H at 7.40 ppm (S.e., N$^+$$\underline{H_3}$)—1H at 6.76 ppm (S, $\underline{H}$ thiazol)—1H at 6.0 ppm (D of D, J$_1$=9 Hz, J$_2$=4 Hz, $\underline{H_7}$)—1H at 5.24 ppm (D, J=13 Hz, C$\underline{H_2}$OCO)—1H at 4.92 ppm (D, J=4 Hz, H$_6$)—1H at 4.84 ppm (D, J=13 Hz, C$\underline{H_2}$OCO)—1H at 4.10 ppm (M, C$\underline{H}$—NH$_2$)—1H at 3.97 ppm (M, C$\underline{H}$—OH)—1H at 3.94 ppm (D, J=17 Hz, C$\underline{H_2}$SO)—1H at 3.55 ppm (D, J=17 Hz, C$\underline{H_2}$SO)—6H at 1.44 ppm (S, (C$\underline{H_3}$)$_2$C)—3H at 1.14 ppm (D, J=7 Hz, C$\underline{H_3}$CH).

NMR no. 16-(b): 1H at 8.5 ppm (D, J=9 Hz, CON$\underline{H}$)—3H at 8.40 ppm (S.e., N$^+$$\underline{H_3}$)—1H at 7.66 ppm (S, CON$\underline{H_2}$)—3H at 7.50 ppm (S.e., N$^{30}$$\underline{H_3}$)—1H at 7.22 ppm (S, CON$\underline{H_2}$)—1H at 6.78 ppm (S, $\underline{H}$ thiazol)—1H at 6.0 ppm (D of D, J$_1$=9 Hz, J$_2$=4 Hz, $\underline{H_7}$)—1H at 5.29 ppm (D, J=13 Hz, C$\underline{H_2}$OCO)—1H at 4.92 ppm (D, J=4 Hz, H$_6$)—1H at 4.79 ppm (D, J=13 Hz, C$\underline{H_2}$OCO-)—1H at 4.26 ppm (M, C$\underline{H}$NH$_2$)—1H at 3.92 ppm (D, J=17 Hz, C$\underline{H_2}$SO)—1H at 3.52 ppm (D, J=17 Hz, C$\underline{H_2}$SO)—2H at 2.71 ppm (M, C$\underline{H_2}$CONH$_2$)—6H at 1.44 ppm (S, (C$\underline{H_3}$)$_2$C).

NMR no. 17-(b): 1H at 8.50 ppm (D, J=9 Hz, CON$\underline{H}$)—3H at 8.45 ppm (S.e., N$^+$$\underline{H_3}$)—3H at 7.45 ppm (S.e., N$^+$$\underline{H_3}$)—1H at 6.78 ppm (S, $\underline{H}$ thiazol)—1H at 6.0 ppm (D of D, J$_1$=9 Hz, J$_2$=4 Hz, $\underline{H_7}$)—1H at 5.24 ppm (D, J=13 Hz, C$\underline{H_2}$OCO)—1H at 4.98 ppm (D, J=4 Hz, H$_6$)—1H at 4.82 ppm (D, J=13 Hz, C$\underline{H_2}$OCO)—1H at 4.13 ppm (M, C$\underline{H}$NH$_2$)—1H at 3.92 ppm (D, J=17 Hz, C$\underline{H_2}$SO)—1H at 3.10 ppm (D, J=17 Hz, C$\underline{H_2}$SO)—1H at 2.50 ppm (M, C$\underline{H_2}$S)—5H at 2.0 ppm (M, C$\underline{H_3}$S et C$\underline{H_2}$—C$\underline{H_2}$—S)—6H at 1.44 ppm S, (C$\underline{H_3}$)$_2$C).

NMR no. 18-(b): 4H at 8.50 ppm (M, CON$\underline{H}$, N$^+$$\underline{H_3}$)—3H at 7.80 ppm (S.e., N$^+$$\underline{H_3}$)—3H at 7.50 ppm (S.e., N$^+$$\underline{H_3}$)—1H at 6.79 ppm (S, $\underline{H}$ thiazol)—1H at 6.0 ppm (D of D, J$_1$=9 Hz, J$_2$=4 Hz, $\underline{H_7}$)—1H at 5.24 ppm (D, J=13 Hz, C$\underline{H_2}$OCO)—1H at 4.97 ppm (D, J=4 Hz, H$_6$)—1H at 4.82 ppm (D, J=13 Hz, C$\underline{H_2}$OCO)—1H at 3.97 ppm (M, C$\underline{H}$NH$_2$)—1H at 3.92 ppm (D, J=17 Hz, C$\underline{H_2}$SO)—1H at 3.60 ppm (D, J=17 Hz, C$\underline{H_2}$SO)—2H at 2.75 ppm (M, C$\underline{H_2}$NH$_2$, —1H at 1.75 ppm (MC$\underline{H_2}$CH)—11H at 1.40 ppm (S.e., (C$\underline{H_3}$)$_2$C, (C$\underline{H_2}$)$_3$CH$_2$NH$_2$).

NMR no. 19-(b): 1H at 9 ppm (S, $\underline{H_2}$ imidazol)—3H at 8.6 ppm (S.e., N$^+$H at 8.5 ppm (D, J=9 Hz, CON$\underline{H}$)—1H at 7.40 ppm (S, $\underline{H_4}$ imidazol)—3H 7.30 ppm (S.e., N$^+$$\underline{H_3}$)—1H at 6.79 ppm (S, $\underline{H}$ thiazol)—1H 6.0 ppm (D of D, J$_1$=9 Hz, J$_2$=4 Hz, $\underline{H_7}$)—1H at 5.22 ppm (D, J=13 Hz, C$\underline{H_2}$OCO)—1H at 4.97 ppm (D, J=4 Hz, H$_6$)—1H at 4.90 ppm (D, J=13 Hz, C$\underline{H_2}$OCO)—1H at 4.40 ppm (M, C$\underline{H}$NH$_2$)—1H at 3.89 ppm (D, J=17 Hz, C$\underline{H_2}$SO)—1H at 3.52 ppm (D, J=17 Hz, C$\underline{H_2}$SO)—2H at 3.20 ppm (M, C$\underline{H_2}$CH)—6H at 1.44 ppm (S, (C$\underline{H_3}$)$_2$C).

NMR no. 20-(b): 1H at 8.50 ppm (D, J=9 Hz, CON$\underline{H}$)—3H at 8.40 ppm (S.e., N$^+$$\underline{H_3}$)—3H at 7.40 ppm (S.e., N$^+$$\underline{H_3}$)—1H at 6.77 ppm (S, $\underline{H}$ thiazol)—1H at 6.0 ppm (D of D, J$_1$=9 Hz, J$_2$=4 Hz, $\underline{H_7}$)—1H at 5.76 ppm (D, J=13 Hz, C$\underline{H_2}$OCO)—1H at 4.95 ppm (D, J=4 Hz, H$_6$)—1H at 4.81 ppm (D, J=13 Hz, C$\underline{H_2}$OCO)—1H at 4.06 ppm (M, C$\underline{H}$NH$_2$)—1H at 3.95 ppm (D, J=17 Hz, C$\underline{H_2}$SO)—1H at 3.63 ppm (D, J=17 Hz, C$\underline{H_2}$SO)—6H at 1.44 ppm (S, (C$\underline{H_3}$)$_2$C)—3H at 1.36 ppm (D, J=7 Hz, C$\underline{H_3}$CH).

NMR no. 21-(a): 8H between 6.5 and 9 ppm (widened signal, NH$_2$, CO$_2$H, TFA)—1H at 8.35 ppm (D, J=9 Hz, CON$\underline{H}$)—1H at 6.80 ppm (S, $\underline{H}$ thiazol)—1H 6.0 ppm (D of D, J$_1$=9 Hz, J$_2$=4 Hz, $\underline{H_7}$)—1H at 5.15 ppm (A of AB, J$_{AB}$=13 Hz, C$\underline{H_2}$OCO)—1H at 5.0 ppm (D, J=4 Hz, H$_6$)—1H at 4.65 ppm (B of AB, J$_{AB}$=13 Hz, C$\underline{H_2}$OCO)—1H 3.95 ppm (A of AB, J$_{AB}$=17 Hz, CH₂SO)—1H at 3.65 ppm (B of AB, J$_{AB}$=17 Hz, CH₂SO)—2H at 2.80 ppm (M, CH₂NH₂) 2H at 2.35 ppm (M, CH₂CO)—10H at 1.45 ppm (S.e., (CH₃)₂C+CH₂(CH₂)₂CH₂).

NMR no. 22-(a): 8H between 6 and 9 ppm (wide signal, TFA, NH₂, CO₂H)—1H at 8.42 ppm (D, J=9 Hz, CONH)—1H at 6.85 ppm (S, H thiazol)—1H 6.05 ppm (D of D, J₁=9 Hz, J₂=4 Hz, H₇)—1H at 5.30 ppm (A of AB, J=13 Hz, CH₂OCO)—1H at 5.05 ppm (D, J=4 Hz, H₆)—1H 4.68 ppm (B of AB, J$_{AB}$=13 Hz, CH₂OCO)—1H at 4.0 ppm (A of AB, J$_{AB}$=17 Hz, CH₂SO)—1H at 3.65 ppm (B of AB, J$_{AB}$=17 Hz, CH₂SO)—8H at 1.75 ppm (M, H, cyclopentane)—6H at 1.45 ppm (S, (CH₃)₂C).

NMR no. 23-(a): 8H between 7 and 10 ppm (wide signal, TFA, NH₂, CO₂H)—1H at 8.50 ppm (D, J=9 Hz, CONH)—1H at 6.92 ppm (S, H thiazol)—1H 6.10 ppm (D of D, J₁=9 Hz, J₂=4 Hz, H₇)—1H at 5.35 ppm (A of AB, J=13 Hz, CH₂OCO)—1H at 5.0 ppm (D, J=4 Hz, H₆)—1H at 4.75 ppm (B of AB, J=13 Hz, CH₂OCO)—1H at 4.0 ppm (A of AB, J$_{AB}$=17 Hz, CH₂SO)—1H at 3.70 ppm (B of AB, J$_{AB}$=17 Hz, CH₂SO)—16H between 1 and 2.3 ppm (M, (CH₃)₂C and cyclohexane).

NMR no. 24-(a): 9H between 8 and 10 ppm (wide signal, NH₂, OH, CO₂H, TFA)—1H at 8.55 ppm (D, J=9 Hz, CONH)—2H at 7.10 ppm (D, J=8 Hz, H meta OH)—1H at 6.90 ppm (S, H thiazol)—2H at 6.80 ppm (D, J=8 Hz, H ortho, OH)—1H at 6.10 ppm (D of D, J₁=9 Hz, J₂=4 Hz, H₇)—1H at 5.80 ppm (A of AB, J=13 Hz, CH₂OCO)—1H at 5.05 ppm (D, J=4 Hz, H₆)—1H at 4.80 ppm (B of AB, J=13 Hz, CH₂OCO-)—1H at 4.30 ppm (M, CHNH₂)—2H at 3.70 ppm (M, CH₂SO)—2H at 3.0 ppm (M, CH₂—C₆H₄OH—6H at 1.46 ppm (S, (CH₃)₂C).

NMR no. 25-(a): 10H between 6.5 and 9.5 ppm (wide signal, NH₂, CO₉H, TFA)—1H at 8.40 ppm (D, J=9 Hz CONH)—1H at 6.85 ppm (S, H thiazol)—1H 6.05 ppm (D of F, J₁=9 Hz, J₂=4 Hz, H₇)—1H at 5.30 ppm (A of AB, J$_{AB}$=13 Hz, CH₂OCO)—1H at 5.0 ppm (D, J=4 Hz, H₆)—1H at 4.85 ppm (B of AB, J$_{AB}$=13 Hz, CH₂OCO)—1H at 4.20 ppm (M, CHNH₂)—2H 3.80 ppm (M, CH₂SO)—2H at 2.95 ppm (M, CH₂NH₂)—2H at 2.20 ppm (M, CH₂CH₂NH₂)—6H at 1.45 ppm (S, (CH₃)₂C).

NMR no. 26-(b): 3H at 8.60 ppm (S.e., N⁺H₃)—1H at 8.44 ppm (D, J=9 Hz, CONH)—1H at 6.78 ppm (S, H thiazol)—1H 6.0 ppm (D of D, J₁=9 Hz, J₂=4 Hz, H₇)—1H at 5.16 ppm (2D, J=13 Hz, CH₂OCO)*—1H at 4.97 ppm (D, J=4 Hz, H₆)—1H at 4.66 ppm (2D, J=13 Hz, CH₂OCO)*—1H at 3.92 ppm (D, J=17 Hz, CH₂SO)—1H at 3.56 ppm (D, J=17 Hz, CH₂SO)—5H between 2.5 and 3.5 ppm (M, CH₂N et CHCO₂)—4H between 1.5 and 2.0 ppm (M, CH₂)₂CH₂N)—6H at 1.44 ppm (S, (CH₃)₂C).

NMR no. 27-(b): 3H at 8.50 ppm (S.e., N⁺H₃)—1H at 8.44 ppm (D, J=9 Hz, CONH)—3H at 7.80 ppm (S.e., N⁺H₃)—3H at 7.30 ppm (S.e., N⁺H₃)—1H at 6.78 ppm (S, H thiazol)—1H 6.0 ppm (D of D, J₁=9 Hz, J₂=4 Hz, H₇)—1H at 5.26 ppm (D, J=13 Hz, CH₂OCO-)—1H at 4.97 ppm (D, J=4 Hz, H₆)—1H 4.84 ppm (D, J=13 Hz, CH₂OCO)—1H at 4.08 ppm (M, CHCO₂-)—1H at 3.94 ppm (D, J=17 Hz, CH₂SO)—1H at 3.56 ppm (D, J=17 Hz, CH₂SO)—2H at 2.80 ppm (M, CH₂NH₂)—4H at 1.60 ppm (M, (CH₂)₂CH₂NH₂)—6H at 1.44 ppm (S, (CH₃)₂C).

NMR no. 28-(b): 1H at 8.37 ppm (D, J=9 Hz, CONH)—3H at 7.90 (S.e., N⁺H₃)—3H at 7.20 ppm (S.e., N⁺H₃)—1H at 6.76 ppm (S, H thiazol)—1H at 6.0 ppm (D of D, J₁=9 Hz, J₂=4 Hz, H₇)—1H at 5.16 ppm (D, J=13 Hz, CH₂OCO)—1H at 4.97 ppm (D, J=4 Hz, H₆)—1H at 4.66 ppm (D, J=13 Hz, CH₂OCO)—1H at 3.92 ppm (D, J=17 Hz, CH₂SO)—1H at 3.58 ppm (D, J=17 Hz, CH₂SO)—1H at 3.50 ppm (M, CHNH₂)—2H at 2.56 ppm (M, CH₂CHNH₂) 6H at 1.44 ppm (S, (CH₃)₂C)—3H at 1.16 ppm (D, J=6 Hz, CH₃—CH).

NMR no. 29-(b): 1H at 8.44 ppm (D, J=9 Hz, CONH)—3H at 7.95 ppm (S.e., N⁺H₃)—3H at 7.50 ppm (S.e., N⁺H₃)—1H at 6.78 ppm (S, H thiazol)—1H at 6.0 ppm (D of D, J₁=9 Hz, J₂=4 Hz, H₇) 1H at 5.20 ppm (2D, J=13 Hz, CH₂OCO)*—1H at 4.95 ppm (M, H₆)—1H at 4.62 ppm (2D, J=13 Hz, CH₂OCO)*—1H at 3.94 ppm (D, J=17 Hz, CH₂SO)—1H at 3.58 ppm (D, J=17 Hz, CH₂SO)—1H at 3.0 ppm (M, CHCO₂)—2H at 2.75 ppm (M, CH₂NH₂)—6H at 1.44 ppm (M, (CH₃)₂C)—3H at 1.10 ppm (D, J=7 Hz, CH₃CH).

NMR no. 30-(b): 4H at 8.45 ppm (M, N⁺H₃, CONH)—8H at 7.35 ppm (M, N⁺H₃, H aromatic)—1H at 6.78 ppm (S, H thiazol)—1H at 6.0 ppm (M, H₇)—1H at 5.05 ppm (2D, J=13 Hz, CH₂OCO)* 1H at 4.94 ppm (2D, J=4 Hz, H₆)*—1H at 4.60 ppm (M, CHNH₂)—1H at 3.66 ppm (2D, J=17 Hz, CH₂SO)*—1H at 3.40 ppm (2D, J=17 Hz, CH₂SO)*—2H at 3.0 ppm (M, CH₂CO₂) 6H at 1.44 ppm (S, (CH₃)₂C).

NMR no. 31-(b): 1H at 8.40 ppm (D, J=9 Hz, CONH)—3H at 7.74 ppm (S.e., N⁺H₃)—3H at 7.40 ppm (S.e., N⁺H₃)—1H at 6.81 ppm (S, H thiazol)—1H at 6.0 ppm (D of D, J₁=9 Hz, J₂=4 Hz, H₇) 1H at 5.13 ppm (D, J=13 Hz, CH₂OCO)—1H at 4.97 ppm (D, J=4 Hz, H₆)—1H at 4.63 ppm (D, J=13 Hz, CH₂OCO)—1H at 3.90 ppm (D, J=17 Hz, CH₂SO)—1H at 3.55 ppm (D, J=17 Hz, CH₂SO)—1H at 3.16 ppm (M, CHNH₂)—2H at 2.40 ppm (M, CH₂CO)—1H 1.77 ppm (M, CH₂CHNH₂)—1H at 1.61 ppm (M, CH₂CHNH₂)—6H at 1.44 ppm (2S, (CH₃)₂C) 1H at 1.0 ppm (D, J=7 Hz, CH₃—CH).

NMR no. 32-(a): 7H between 7 and 9 ppm (NH, NH₂, CO₂H, TFA)—1H at 8.50 ppm (D, J=9 Hz, CONH)—1H at 6.90 ppm (S, H thiazol)—1H at 6.05 ppm (D of D, J₁=9 Hz, J₂=4 Hz, H₇)—1H at 5.15 ppm (A of AB, J=13 Hz, CH₂OCO)—1H at 5.0 ppm (D, J=4 Hz, H₆)—1H at 4.70 ppm (B of AB, J=13 Hz, CH₂OCO-)—1H at 3.95 ppm (A of AB, J$_{AB}$=17 Hz, CH₂SO)—1H at 3.65 ppm (B of AB, J$_{AB}$=17 Hz, CH₂SO)—2H at 2.90 ppm (M, CH₂NH)—3H at 2.45 ppm (D, J=6 Hz, CH₃NH)—2H at 2.4 ppm (M, CH₂CO)—2H at 1.70 ppm (M, CH₂CH₂CH₂)—6H at 1.42 ppm (S, (CH₃)₂C).

NMR no. 33-(a): 7H between 7 and 9.5 ppm (NH₂, NH, CO₂H, TFA)—1H at 8.46 ppm (D, J=9 Hz, CONH)—1H at 6.90 ppm (S, H thiazol)—1H at 6.05 ppm (D of D, J₁=9 Hz, J₂=4 Hz, H₇)—1H at 5.15 ppm (A of AB, J$_{AB}$=13 Hz, CH₂OCO)—1H at 5.0 ppm (D, J=4 Hz, H₆)—1H at 4.70 ppm (B of AB, J$_{AB}$=13 Hz, CH₂OCO)—1H at 3.90 ppm (A of AB, J$_{AB}$=17 Hz, CH₂SO) 1H at 3.65 ppm (B of AB, J$_{AB}$=17 Hz, CH₂SO)—2H at 2.75 ppm (M, CH₂NHCH₃)—5H 2.45 ppm (M, CH₃NH and CH₂CO)—10H at 1.45 ppm (S.e., (CH₃)₂C and CH₂(CH₂)₂CH₂).

NMR no. 34-(a): 8H between 6 and 9 ppm (widened signal, NH₂, TFA, OH, CO₂H)—1H at 8.47 ppm (D, J=9 Hz, CONH)—1H at 6.90 ppm (S, H thiazol)—1H at 6.15 ppm (D of D, J₁=9 Hz, J₂=4 Hz, H₇)—1H at 5.35 ppm (AB, J$_{AB}$=13 Hz, CH₂OCO)—1H at 5.0 ppm (D, J=4 Hz, H₆)—1H at 4.85 ppm (B of AB, J$_{AB}$=13 Hz, CH₂OCO)—4H at 3.95 ppm (M, CH₂SO and CHOHCHNH$_2$)—6H at 1.45 ppm (S, (CH$_3$)$_2$C)—3H at 1.20 ppm (D, J=7 HZ, CH$_3$CHOH).

NMR no. 35-(b): 1H at 8.50 ppm (D, J=9 Hz, CONH)—3H at 8.35 ppm (S.e., N+H$_3$)—2H at 7.94 ppm (D, J=8 Hz, H ortho CO)—2H at 7.55 ppm (D, J=8 Hz, H meta CO)—1H at 6.84 ppm (S, H thiazol)—1H at 6.0 ppm (D of D, J$_1$=9 Hz, J$_2$=4 Hz, H$_7$)—1H at 5.44 ppm (D, J=13 Hz, CH$_2$OCO)—1H at 4.99 ppm (D, J=4 Hz, H$_6$)—1H at 4.86 ppm (D, J=13 Hz, CH$_2$OCO)—3H at 4.1 ppm (M, CH$_2$NH$_2$, CH$_2$SO)—1H at 3.72 ppm (D, J=17 Hz, CH$_2$SO)—6H at 1.44 ppm (2S, (CH$_3$)$_2$C).

NMR no. 36-(a): 3H at 9.30 ppm (S.e., N+H$_3$)—1H at 8.55 ppm (D, J=9 Hz, CONH)—3H at 8.05 ppm (S.e., N+H$_3$)—1H at 6.92 ppm (S, H thiazol)—1H 6.05 ppm (D of D, J$_1$=9 Hz, J$_2$=4 Hz, H$_7$)—1H at 5.30 ppm (A of AB, J$_{AB}$=13 Hz, CH$_2$OCO)—1H at 5.05 ppm (D, J=4 Hz, H$_6$)—1H at 4.70 ppm (B of AB, J$_{AB}$=13 Hz, CH$_2$OCO)—1H at 3.95 ppm (A of AB, J$_{AB}$=17 Hz, CH$_2$SO)—1H at 3.65 ppm (B of AB, J$_{AB}$=17 Hz, CH$_2$SO)—2H at 3.0 ppm (S.e., CH$_2$NH$_2$)—6H at 1.45 ppm (S, (CH$_3$)$_2$C—ON)—6H at 1.17 ppm (S, (CH$_3$)$_2$CO$_2$CH$_2$).

NMR no. 37-(b): 8H between 5 and 9 ppm (wide signal, CO$_2$H, TFA, NH$_2$)—1H at 8.50 ppm (D, J=9 Hz, CONH)—1H at 6.90 ppm (S, H thiazol)—1H at 6.0 ppm (D of D, J=9 Hz, J$_2$=4 Hz, H$_7$)—1H at 5.15 ppm (D, J=13 Hz, CH$_2$OCO)—1H at 5.0 ppm (D, J=4 Hz, H$_6$)—1H at 4.58 ppm (D, J=13 Hz, CH$_2$OCO)—1H at 3.9 ppm (D, J=17 Hz, CH$_2$SO)—1H at 3.54 ppm (D, J=17 Hz, CH$_2$SO)—2H at 2.6 ppm (M, CH$_2$NH$_2$)—1H at 2.25 ppm (T, J=12 Hz, CHCO$_2$)—4H at 1.84 ppm (M, CH$_2$CHCO)—6H at 1.45 ppm (S, (CH$_3$)$_2$C)—3H at 1.25 ppm (M, CHCH$_2$NH$_2$ and CH$_2$CHCH$_2$NH$_2$)—2H at 0.95 ppm (M, CH$_2$CHCH$_2$NH$_2$).

NMR no. 38-(b): 1H at 8.37 ppm (D, J=9 Hz, CONH)—3H at 7.90 ppm (S.e., N+H$_3$)—3H at 7.40 ppm (S.e., N+H$_3$)—1H at 6.79 ppm (S, H thiazol)—1H at 6.0 ppm (D of D, J$_1$=9 Hz, J$_2$=4 Hz, H$_7$)—1H at 5.11 ppm (2D, J=13 Hz, CH$_2$OCO)*—1H at 4.98 ppm (D, J=4 Hz, H$_6$)—1H at 4.61 ppm (2D, J=13 Hz, CH$_2$OCO)*—1H at 3.90 ppm (D, J=17 Hz, CH$_2$SO)—1H at 3.59 ppm (D, J=17 Hz, CH$_2$SO)—1H at 3.0 ppm (S.e., CHNH$_2$)—1H at 2.40 ppm (M, CHCO$_2$)—1H at 2.10 ppm (M, CH$_2$CHNH$_2$)—3H at 1.80 ppm (M, CH$_2$CHNH$_2$)—6H 1.44 ppm (2S, (CH$_3$)$_2$C)—4H between 1 and 1.5 ppm (M, CH$_2$—CH$_2$—CH—CO$_2$).

NMR no. 39-(b): 1H at 8.5 ppm (D, J=9 He, CONH)—6H between 7 and 8 ppm (wide signal, NH$_2$, TFA-)—1H at 6.81 ppm (S, H thiazol)—1H at 6.0 ppm (D of D, J=9 Hz, J$_2$=4 Hz, H$_7$)—1H at 5.15 ppm (2D, J=13 Hz, CH$_2$OCO)*—1H at 5.0 ppm (D, J=4 Hz, H$_6$)—1H at 4.63 ppm (2D, J=13 Hz, CH$_2$OCO)*—1H at 3.89 ppm (D, J=17 Hz, CH$_2$SO)—1H at 3.56 ppm D, J=17 Hz, CH$_2$SO)—2H at 2.77 ppm (M, CH$_2$NH$_2$)—1H at 2.52 ppm (M, CHCO$_2$)—1H at 1.84 ppm (M, CH$_2$CH)—1H at 1.56 ppm (M, CH$_2$CH)—6H at 1.44 ppm (S, (CH$_3$)$_2$C)—3H at 1.06 ppm (D, J=7 Hz, CH$_3$CH).

NMR no. 40-(a): 1H at 8.45 ppm (D, J=9 Hz, CONH)—8H at 7.30 ppm (S.e., N+H$_3$, CO$_2$H)—1H at 6.80 ppm S, H thiazol)—1H at 6.0 ppm (M, H$_7$)—1H at 5.20 ppm (A of AB, J$_{AB}$=13 Hz, CH$_2$OCO) 1H at 4.90 ppm (B of AB, J$_{AB}$=13 Hz, CH$_2$OCO)—1H at 4.90 ppm (D, J=4 Hz, H$_6$)—3H at 3.80 ppm (M, CH$_2$SO, CHNH$_2$)—1H at 2.00 ppm (M, CH(CH$_3$)$_2$)—6H at 1.45 ppm (S, (CH$_3$)$_2$C)—6H at 0.95 ppm (2D, J=7 Hz, (CH$_3$)$_2$CH).

NMR no. 41-(a): 2H at 8.50 ppm (S.e., N+H$_2$)—1H at 8.45 ppm (D, J=9 Hz, CONH)—3H at 7.30 ppm S.e., N+H$_3$)—1H at 6.80 ppm (S, H thiazol)—1H at 6.0 ppm (M, H$_7$)—1H at 5.15 ppm (A of AB, J$_{AB}$=13 Hz, CH$_2$OCO)—1H at 4.96 ppm (D, J=4 Hz, H$_6$)—1H at 4.65 ppm (B of AB, 13 Hz, CH$_2$OCO)—1H at 3.90 ppm (A of AB, J=17 Hz, CH$_2$SO)—1H at 3.65 ppm (B of AB, J=17 Hz, CH$_2$SO)—2H at 3.00 ppm (M, CH$_2$NH)—5H at 2.50 ppm (M, CH$_3$NH, CH$_2$CO$_2$)—6H at 1.42 ppm (S, (CH$_3$)$_2$C).

NMR no. 42-(a): 7H at 9.4 ppm (S.e., N+H$_3$, N+H$_2$, CO$_2$H)—1H at 8.45 ppm (D, J=9 Hz, CONH)—1H at 6.85 ppm (S, H thiazol)—1H at 6.00 ppm (M, H$_7$)—1H at 5.00 ppm (D, J=4 Hz, H$_6$)—1H at (A of AB, J$_{AB}$=13 Hz, CH$_2$OCO)—1H at 4.65 ppm (B of AB, J$_{AB}$=13 Hz, CH$_2$OCO)—1H at 3.85 ppm (A of AB, J$_{AB}$=17 Hz, CH$_2$SO)—1H at 3.60 ppm (B of AB, J$_{AB}$=17 Hz, CH$_2$SO)—4H at 2.85 ppm (M, CH$_2$NHCH$_2$)—2H at 2.40 ppm (M,

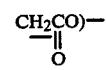

2H at 1.80 ppm (M, CH$_2$CH$_2$CH$_2$NH)—6H at 1.45 ppm (S, (CH$_3$)$_2$C)—3H at 1.10 ppm (T, J=7 Hz, CH$_3$CH$_2$NH).

NMR no. 43-(a): 2H at 8.50 ppm (S.e., N+H$_2$)—1H at 8.40 ppm (D, J=9 Hz, CONH)—3H at 7.00 ppm (S.e., N+H$_3$)—1H at 6.76 pm (S, H thiazol)—1H at 5.95 ppm (M, H$_7$)—1H at 5.10 ppm (A of AB, J$_{AB}$=13 Hz, CH$_2$OCO)—1H at 5.0 ppm (D, J=4 Hz, H$_6$)—1H at 4.65 ppm (B AB, J$_{AB}$=13 Hz, CH$_2$OCO)—1H at 3.85 ppm (A of AB, J$_{AB}$=17 Hz, CH$_2$SO)—1H at 3.50 ppm, B of AB, J$_{AB}$=17 Hz, CH$_2$SO)—1H at 3.30 ppm (M, CHNH)—5H at 2.45 ppm (M, CH$_3$NH and

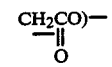

2H at 1.80 ppm (M,

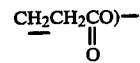

6H at 1.45 ppm (S, (CH$_3$)$_2$C)—3H at 1.10 ppm (D, J=7 Hz, CH$_3$CH).

NMR no. 44-(a): 1H at 8.40 ppm (D, J=9 Hz, CONH)—7H at 7.80 ppm (S.e., N+H$_3$, N+H$_2$, CO$_2$H)—1H at 6.80 ppm (S, H thiazol)—1H at 6.00 ppm (M, H$_7$)—1H at 5.00 ppm (M, H$_6$)—1H at 5.00 ppm (A of AB, J$_{AB}$=13 Hz, CH$_2$OCO)—1H at 4.65 ppm (B of AB, J$_{AB}$=13 Hz), CH$_2$OCO)—1H at 3.85 ppm (A of AB, J$_{AB}$=17 Hz, CH$_2$SO)—1H at 3.55 ppm (B of AB, J$_{AB}$=17 Hz, CH$_2$SO)—2H at 2.80 ppm (M, CH$_2$NH)—5H at 2.40 ppm (M, CH$_3$NH, CH$_2$CO$_2$)—12H at 1.45 ppm (S.e., (CH$_3$)$_2$C and CH$_2$(CH$_2$)$_3$CH$_2$NH).

NMR no. 45-(b): 1H at 8.75 ppm (D, J=9 Hz, CONH)—1H at 8.60 ppm (S.e., N+H$_2$)—1H at 8.40 ppm (S.e., N+H$_2$)—3H at 7.30 ppm (S.e., N+H$_3$)—1H at 6.78 ppm (S, H thiazol)—1H at 5.91 ppm (D of D, J$_1$=9 Hz, J$_2$=4 Hz, H$_7$)—1H at 5.13 ppm (D, J=13 Hz, CH$_2$OCO)—1H at 4.95 ppm (D, J=4 Hz, H$_6$)—1H at 4.61 ppm (D, J=13 Hz, CH$_2$OCO)—2H at 4.55 ppm (S, CH$_2$ON)—1H at 3.84 ppm (A of AB, J$_{AB}$=17 Hz, CH₂SO)—1H at 3.55 ppm (B of AB, J$_{AB}$=17 Hz, CH₂SO)—2H at 3.20 ppm (M, CH₂NH)—2H at 2.90 ppm (M, CH₂NH)—1H at 2.64 ppm (M, CHCO₂)—2H at 1.95 ppm (M, CH₂CH₂NH)—2H at 1.66 ppm (M, CH₂CH₂NH).

NMR no. 46-(b): 1H at 8.75 ppm (D, J=9 Hz, CONH)—1H at 8.60 ppm (S.e., N⁺H₂)—1H at 8.40 ppm (S.e., N⁺H₂)—3H at 7.30 ppm (S.e., N⁺H₃)—1H at 6.78 ppm (S, H thiazol)—1H at 5.94 ppm (D of D, J₁=9 Hz, J₂=4 Hz, H₇)—1H at 5.13 ppm (D, J=13 Hz, CH₂OCO)—1H at 4.95 ppm (D, J=4 Hz, H₆)—1H at 4.61 ppm (D, J=13 Hz, CH₂OCO)—1H at 3.90 ppm (A of AB, J=17 Hz, CH₂SO)—1H at 3.55 ppm (B of AB, J=17 Hz, CH₂SO)—2H at 3.20 ppm (M, CH₂NH)—2H at 2.90 ppm (M, CH₂NH)—1H at 2.64 ppm (M, CHCO₂)—4H at 2.40 ppm (M,

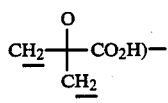

6H between 1.5 and 2 ppm

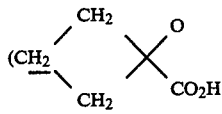

CH₂—CH₂NH).

NMR no. 47-(b): 1H at 8.79 ppm (D, J=9 Hz, CONH)—3H at 8.30 ppm (S.e., N⁺H₃)—2H at 7.97 ppm (D, J=8 Hz, H ortho CO)—2H at 7.55 ppm (D, J=8 Hz, H meta CO)—3H at 7.30 ppm (S.e., N⁺H₃)—1H at 6.84 ppm (S, H thiazol)—1H at 5.92 ppm (D of D, J₁=9 Hz, J₂=4 Hz, H₇)—1H at 5.40 ppm (D, J=13 Hz, CH₂OCO)—1H at 4.95 ppm (D, J=4 Hz, H₆)—1H at 4.84 ppm (D, J=13 Hz, CH₂OCO)—2H at 4.56 ppm (S, CH₂ON)—1H at 4.08 ppm (M, CH₂NH₂)—1H at 4.00 ppm (A of AB, J$_{AB}$=17 Hz, CH₂SO)—1H at 3.71 ppm (B of AB, J$_{AB}$=17 Hz, CH₂SO).

NMR no. 48-(b): 1H at 8.75 ppm (D, J=9 Hz, CONH)—3H at 8.30 ppm (S.e., N⁺H₃)—2H at 7.95 ppm (D, J=8 Hz, H ortho CO)—2H at 7.55 ppm (D, J=8 Hz, H meta CO)—3H at 7.30 ppm (S.e., N⁺H₃)—1H at 6.78 ppm (S, H thiazol)—1H at 5.95 ppm (D of D, J₁=9 Hz, J₂=4 Hz, H₇)—1H at 4.44 ppm (D, J=13 Hz, CH₂OCO)—1H at 4.98 ppm (D, J=4 Hz, H₆)—1H at 4.81 ppm (D, J=13 Hz)—CH₂OCO)—1H at 4.10 ppm (S.e., CH₂NH₂)—1H at 4.05 ppm (A of AB, J$_{AB}$=17 Hz, CH₂SO)—1H at 3.71 ppm (B of AB, J$_{AB}$=17 Hz, CH₂SO)—4H 2.40 ppm (M,

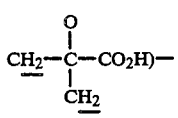

2H at 1.85 ppm (M,

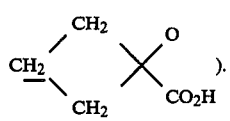

NMR no. 49-(b): 1H at 8.75 ppm (D, J=9 Hz, CONH)—3H at 7.70 ppm (S.e., N⁺H₃)—3H at 7.30 ppm (S.e., N⁺H₃)—1H at 6.82 ppm (S, H thiazol)—1H at 5.90 ppm (D of D, J₁=9 Hz, J₂=4 Hz, H₇)—1H at 5.10 ppm (D, J=13 Hz, CH₂OCO)—1H at 4.95 ppm (D, J=4 Hz, H₆)—1H at 4.56 ppm (D, J=13 Hz, CH₂OCO)—2H at 4.53 ppm (S, CH₂ON)—1H 3.84 ppm (A of AB, J$_{AB}$=17 Hz, CH₂SO)—1H at 3.55 ppm (B of AB, J$_{AB}$=17 Hz, CH₂SO)—2H at 2.76 ppm (M, CH₂NH₂)—2H at 2.40 ppm (M, CH₂CO₂)—2H at 1.72 ppm (M, CH₂CH₂CH₂NH₂).

NMR no. 50-(b): 1H at 8.75 ppm (D, J=9 Hz, CONH)—3H at 7.75 ppm (S.e., N⁺H₃)—3H at 7.25 ppm (S.e., N⁺H₃)—1H at 6.77 ppm (S, H thiazol)—1H at 5.94 ppm (D of D, J₁=9 Hz, J₂=4 Hz, H₇)—1H at 5.11 ppm (D, J=13 Hz, CH₂OCO)—1H at 4.95 ppm (D, J=4 Hz, H₆)—1H at 4.63 ppm (D, J=13 Hz, CH₂OCO)—1H at 3.89 ppm (A of AB, J=17 Hz, CH₂SO)—1H at 3.55 ppm (B of AB, J=17 Hz, CH₂SO)—2H at 2.78 ppm (M, CH₂NH₂)—6H at 2.40 ppm (M,

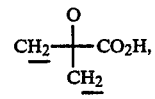

CH₂CO₂)—4H at 1.85 ppm (M, CH₂CH₂NH₂,

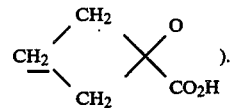

NMR no. 51-(b): 1H at 8.75 ppm (D, J=9 Hz, CONH)—3H at 7.60 ppm (S.e., N⁺H₃)—3H at 7.30 ppm (S.e., N⁺H₃)—1H at 6.82 ppm (S, H thiazol)—1H at 5.87 ppm (D of D, J₁=9 Hz, J₂=4 Hz, H₇)—1H at 5.61 ppm (D, J=13 Hz, CH₂OCO)—1H at 4.92 ppm (D, J=4 Hz, H₆)—1H at 4.58 ppm (D, J=13 Hz, CH₂OCO)—2H at 4.57 ppm (S, CH₂ON)—1H at 3.81 ppm (A of AB, J=13 Hz, CH₂SO)—1H at 3.55 ppm (B of AB, J=13 Hz, CH₂SO)—2H at 2.75 ppm (M, CH₂NH₂)—2H at 2.31 ppm (M, CH₂CO₂)—4H at 1.50 ppm (M, CH₂(CH₂)₂CH₂N).

NMR no. 52-(b): 1H at 8.75 ppm (D, J=9 Hz, CONH)—3H at 7.70 ppm (S.e., N⁺H₃)—3H at 7.30 ppm (S.e. N⁺H₃)—1H at 6.78 ppm (S, H thiazol)—1H 5.92 ppm (D of D, J₁=9 Hz, J₂=4 Hz, H₇)—1H at 5.13 ppm (D, J=13 Hz, CH₂OCO)—1H at 4.95 ppm (D, J=4 Hz, H₆)—1H at 4.58 ppm (D, J=13 Hz, CH₂OCO)—1H at 3.86 ppm (A of AB, J=17 Hz, CH₂SO)—1H at 3.55 ppm (B of AB, J=17 Hz, CH₂SO)—2H at 2.74 ppm (M, CH₂NH₂)—6H at 2.40 ppm (M,

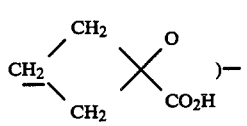

2H at 1.85 ppm (M,

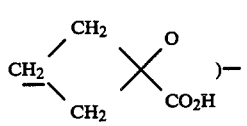

4H at 1.50 ppm (M, CH₂CH₂CH₂CO₂).

NMR no. 53-(b): 1H at 8.80 ppm (D, J=9 Hz, CONH)—3H at 8.40 ppm (S.e., N+H$_3$)—3H at 7.40 ppm (S.e., N+H$_3$)—1H at 6.78 ppm (S, H thiazol)—1H at 5.95 ppm (D of D, J$_1$=9 Hz, J$_2$=4 Hz, H$_7$)—1H at 5.25 ppm (D, J=13 Hz, CH$_2$OCO)—1H at 4.95 ppm (D, J=4 Hz, H$_6$)—1H at 4.78 ppm (D, J=13 Hz, CH$_2$OCO)—1H at 4.08 ppm (M, CHNH$_2$)—1H at 3.95 ppm (A of AB, J=17 Hz, CH$_2$SO)—1H at 3.60 ppm (B of AB, J=17 Hz, CH$_2$SO)—4H at 2.40 ppm (M,

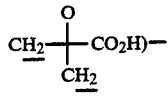

2H at 1.80 ppm (M,

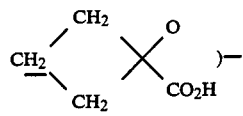

3H at 1.36 ppm (D, J=7 Hz, CH$_3$CH).

NMR no. 54-(b): 1H at 8.75 ppm (D, J=9 Hz, CONH)—3H at 7.87 ppm (S.e., N+H$_3$)—3H at 7.30 ppm (S.e., N+H$_3$)—1H at 6.78 ppm (S, H thiazol)—1H at 5.95 ppm (D of D, J$_1$=9 Hz, J$_2$=4 Hz, H$_7$)—1H at 5.19 ppm (2D, J=13 Hz, CH$_2$OCO)*—1H at 4.95 ppm (D, J=4 Hz, H$_6$)—1H at 4.64 ppm (2D, J=13 Hz, CH$_2$OCO)-*—1H at 3.92 ppm (A of AB, J=17 Hz, CH$_2$SO)—1H at 3.55 ppm (B of AB, J=17 Hz, CH$_2$SO)—1H at 3.0 ppm (M, CHCO$_2$)—2H at 2.80 ppm (M, CH$_2$NH$_2$)—4H at 2.40 ppm (M,

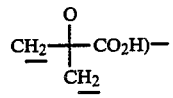

2H at 1.80 ppm (M,

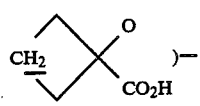

3H at 1.08 ppm (D, J=7 Hz, CH$_3$CH).

NMR no. 55-(b): 1H at 8.75 ppm (D, J=9 Hz, CONH)—3H at 7.80 ppm (S.e., N+H$_3$)—3H at 7.30 ppm (S.e., N+H$_3$)—1H at 6.80 ppm (S, H thiazol)—1H at 5.95 ppm (M, H$_7$)—1H at 5.20 ppm (D, J=13 Hz, CH$_2$OCO-)—1H at 4.95 ppm (S.e., H$_6$)—1H at 4.63 ppm (D, J=13 Hz, CH$_2$OCO)—1H at 3.90 ppm (A of AB, J=17 Hz, CH$_2$SO)—1H at 3.58 ppm (B of AB, J=17 Hz, CH$_2$SO)—2H at 2.93 ppm (M, CH$_2$NH$_2$)—4H at 2.40 ppm (M,

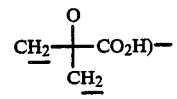

2H at 1.90 ppm (M,

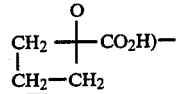

6H at 1.14 ppm (S, (CH$_3$)$_2$C).

NMR no. 56-(b): 1H at 8.75 ppm (D, J=9 Hz, CONH)—3H at 7.75 ppm (S.e., N+H$_3$)—3H at 7.35 ppm (S.e., N+H$_3$)—1H at 6.80 ppm (S, H thiazol)—1H at 5.95 ppm (D of D, J$_1$=9 Hz, J$_2$=4 Hz, H$_7$)—1H at 5.15 ppm (2D, J=13 Hz, CH$_2$OCO)*—1H at 4.95 ppm (D, J=4 Hz, H$_6$)—1H at 4.60 ppm (2D, J=13 Hz, CH$_2$OCO)-*—1H at 3.90 ppm (A of AB, J=17 Hz, CH$_2$SO)—1H at 3.56 ppm (B of AB, J=17 Hz, CH$_2$SO)—2H at 2.74 ppm (M, CH$_2$NH$_2$)—1H at 2.50 (M, CHCO$_2$)—4H at 2.40 ppm (M,

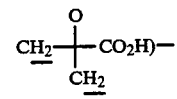

3H at 1.90 ppm (M,

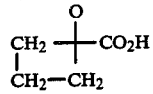

and CH$_2$CH$_2$NH$_2$)—1H at 1.55 ppm (M, CH$_2$CH$_2$NH$_2$)—3H at 1.08 ppm (D, J=7 Hz, CH$_3$CH).

NMR no. 57-(b): 1H at 8.80 ppm (D, H=9 Hz, CONH)—3H at 8.40 ppm (S.e., N+H$_3$)—3H at 7.40 ppm (S.e., N+H$_3$)—1H at 6.79 ppm (S H thiazol)—1H at 5.95 ppm (D of D, J$_1$=9 Hz, J$_2$=4 Hz, H$_7$)—1H at 5.28 ppm (D, J=13 Hz, CH$_2$OCO)—1H at 4.95 ppm (D, J=4 Hz, H$_6$)—1H at 4.75 ppm (D, J=13 Hz, CH$_2$OCO)—1H at 3.95 ppm (A of AB, J=17 Hz, CH$_2$SO)—1H at 3.61 ppm (B of AB, J=17 Hz, CH$_2$SO)—4H at 2.40 ppm (M,

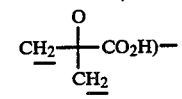

2H at 2.10 ppm (M, CH$_2$ cyclopentane)—2H at 1.90 (M,

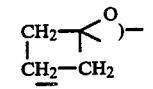

6H at 1.80 ppm (M, CH$_2$ cyclopentane).

NMR no. 58-(b): 1H at 8.75 ppm (D, J=9 Hz, CONH)—3H at 2.70 ppm (S.e., N+H$_3$)—3H at 7.30 ppm (S.e., N+H$_3$)—1H at 6.84 ppm (S, H thiazol)—1H at 5.89 ppm (D of D, J$_1$=9 Hz, J$_2$=4 Hz, H$_7$)—1H at 5.13 ppm (D, J=13 Hz, CH$_2$OCO)—1H at 4.95 ppm (D, J=4 Hz, H$_6$)—3H at 4.55 ppm (M, CH$_2$ON and CH$_2$OCO)—1H at 3.82 ppm (A of AB, J=17 Hz, CH$_2$SO)—1H at 3.55 ppm (B of AB, J=17 Hz, CH$_2$SO)—2H at 2.60 ppm (M, CH$_2$NH$_2$)—1H at 2.21 ppm (M, CHCO$_2$)—4H at 1.80 ppm, (M, CH$_2$ cyclohexane)—1H at 1.45 ppm (M, CHCH$_2$NH$_2$)—2H at 1.25 ppm (M, CH$_2$ cyclohexane)—2H at 0.90 ppm (M, CH$_2$ cyclohexane).

NMR no. 59-(b): 1H at 8.67 ppm (D, J=9 Hz, CONH)—3H at 7.70 ppm (S.e., N+H₃)—3H at 7.30 ppm (S.e., N+H₃)—1H at 6.82 ppm (S, H thiazol)—1H at 5.94 ppm (D of D, J₁=9 Hz, J₂=4 Hz, H₇)—1H at 5.13 ppm (D, J=13 Hz, CH₂OCO)—1H at 4.95 ppm (D, J=4 Hz, H₆)—1H at 4.56 ppm (D, J=13 Hz, CH₂OCO)—1H at 3,87 ppm (A of AB, J=17 Hz, CH₂SO)—2H at 3.55 ppm (B of AB, J=17 Hz, CH₂SO)—2H at 2.60 ppm (M, CH₂NH₂)—5H between 2.0 and 2.5 ppm, 6H between 1.6 and 2.0 ppm, 3H between 1.1 and 1 6 ppm, 2H at 0.90 ppm (M,

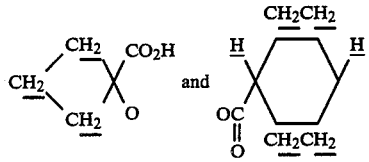

NMR no. 60-(b): 1H at 8.60 ppm (2D, J=9 Hz, CONH)*—3H at 7.70 ppm (S.e., N+H₃)—3H at 7.30 ppm S.e., N+H₃)—1H at 6.82 ppm (2S, H thiazol)-*—1H at 5.95 ppm (D of D, J₁=9 Hz, J₂=4 Hz, H₇)—1H at 5.13 ppm (D, J=13 Hz, CH₂OCO)—1H at 4.95 ppm (2D, H₆)*—2H at 4.60 ppm (M, CH₂OCO+CHON)—1H at 3.86 ppm (2D, J=17 Hz, CH₂SO)-*—1H at 3.56 ppm (2D, J=17 Hz, CH₂SO)*—2H at 2.75 ppm (M, CH₂NH₂)—2H at 2.40 ppm (T, J=7 Hz, CH₂CO₂)—2H at 1.75 ppm (M, CH₂CH₂CH₂NH₂)—3H at 1.39 ppm (D, J=7 Hz, CH₃CH).

NMR no. 61-(b): 1H at 8.70 ppm (2D, J=9 Hz, CONH)*—3H at 7.70 ppm (S.e., N+H₃)—3H at 7.30 ppm S.e., N+H₃)—1H at 6.82 ppm (2S, H thiazol)-*—1H at 5.95 ppm (D of D, J₁=9 Hz, J₂=4 Hz, H₇)—1H at 5.12 ppm (D, J=13 Hz, CH₂OCO)—1H at 4.94 ppm (2D, H₆)*—2H at 4.60 pm (M, HCON, and CH₂OCO)—1H at 3,86 ppm (A of AB, J=17 Hz, CH₂SO)—1H at 3.55 ppm (B of AB, J=17 Hz, CH₂SO)—2H at 2.75 ppm (M, CH₂NH₂)—2H at 2.31 ppm (M, CH₂CO₂)—4H at 1.50 ppm (M, CH₂CH₂CH₂CH₂NH₂)—3H at 1.45 ppm (D, J=7 Hz, CH₃CH).

NMR no. 62-(b): 2H at 8.60 ppm (M, CONH, N+H₃)—1H at 8.40 ppm (S.e., N+H₂)—3H at 7.30 ppm (S.e., N+H₃)—1H at 6.82 ppm (2S, H thiazol)*—1H at 5.95 ppm (D of D, J₁=9 Hz, J₂=4 Hz, H₇)—1H at 5.14 ppm (D, J=13 Hz, CH₂OCO)—1H at 4.95 ppm (2D, H₆)*—2H at 4.60 ppm (M, CH—ON, and CH₂OCO)—1H at 3.88 ppm (2D, J=17 Hz, CH₂SO)—1H at 3.55 ppm (D, J=17 Hz, CH₂SO)—2H at 3.20 and 2H at 2.95 ppm (M,

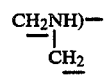

1H at 2.66 ppm (M, CHCO₂)—2H at 1.95 ppm and 2H at 1.70 ppm (M,

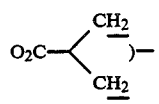

3H at 1.45 ppm (D, J=7 Hz, CH₃CH).

NMR no. 63-(b): 1H at 8.70 ppm (2D, J=9 Hz, CONH)*—3H at 8.20 ppm (S.e., N+H₃)—2H at 7.95 ppm (D, J=Hz, H ortho CO₂)—2H at 7.55 ppm (D, J=8 Hz, H meta CO₂)—3H at 7.30 ppm (S.e., N+H₃) 1H at 6.82 ppm (2S, H thiazol)*—1H at 5 95 ppm (D of D, J₁=9 Hz, J₂=4 Hz, H₇)—1H at 5.44 ppm (D, J=13 Hz, CH₂OCO)—1H at 4.96 ppm (2D, H₆)*—1H at 4.84 ppm (D, J=13 Hz, CH₂OCO)—1H at 4.60 ppm (Q, J=7 Hz, CHON)—2H at 4.10 ppm (M, CH₂NH₂)—1H at 3.90 ppm (D, J=17 Hz, CH₂SO)—1H at 3.70 ppm (D, J=17 Hz, CH₂SO)—3H at 1.45 ppm (D, J=7 Hz, CH₃CH).

NMR no. 64-(b): 1H at 8.60 ppm (2D, J=9 Hz, CONH)*—3H at 7.70 ppm (S.e., N+H₃)—1H at 6.80 ppm (2S, H thiazol)*—1H at 5.95 ppm (D of D, J₁=9 Hz, J₂=4 Hz, H₇)—5H between 4 and 6 ppm (S.e., N+H₃ CO₂H)—1H 5.13 ppm (D, J=13 Hz, CH₂OCO-)—1H 4.95 ppm (2D, H₆)*—2H at 4.60 ppm (M, CH₂OCO and CHON)—1H at 3.86 ppm (A of AB, J=17 Hz, CH₂SO)—1H at 3.55 ppm (B of AB, J=17 Hz, CH₂SO)—2H at 2.61 ppm (M, CH₂NH₂)—1H at 2.21 ppm (M, CHCO₂)—4H at 1.80 ppm (M,

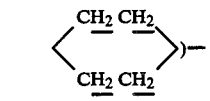

3H at 1.45 ppm (D, J=7 Hz, CH₃CH)—2H at 1.25 ppm and 2H at 0.90 ppm (M,

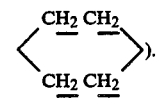

NMR no. 65-(b): 1H at 8.66 ppm (D, J=9 Hz, CONH)—3H at 8.15 ppm (Se., CH₂N⊕H₃)—1H at 8.05 ppm (S, HAr 2')—1H at 7.94 ppm (D, J=7 Hz, HAr 6')—1H at 7.71 ppm (D, J=7 Hz, HAr 4')—1H at 7.55 ppm (T, J=7 Hz, H5')—1H at 6.95 ppm (S, H thiazol)—1H at 6.00 ppm (D of D, J₁=9 Hz, J₂=4 Hz, H₇) 1H at 5.45 ppm (D, J=13 Hz, CH₂OCO)—1H at 5.00 ppm (D, J=4 Hz, H₆)—1H at 4.87 ppm (D, J=13 Hz, CH₂OCO-)—3H at 4.05 ppm (M, CH₂N⊕H₃ et CH₂SO)—1H at 3.75 ppm (D, J=17 Hz, CH₂SO)—3H at 1.48 ppm (S, CH₃)—3H at 1.47 ppm (S, CH₃).

NMR no. 66-(b): 1H at 8.80 ppm (D, J=9 Hz, CONH)—3H at 8.05 ppm (Se., CH₂N⊕H₃)—1H at 6.95 ppm (S, H thiazol)—1H at 6.00 ppm (D of D, J₁=9 Hz, J₂=4 Hz, H₇)—1H at 5.20 ppm (2D superposed, J=13 Hz, CH₂OCO)—1H at 5.10 ppm (2D, J=4 Hz, H₆)—1H at 4.56 ppm (2D superposed, J=13 Hz, CH₂OCO)—4H at 3.90 ppm (M, CH₂SO and CH₂N⊕H₃)—3H at 2.80 ppm (M, CHCO₂, CHCH₂N⊕H₃, and H Eq in α du CO₂)—1H at 2.00 ppm (M, H Ax in α of CO₂)—6H at 1.50 ppm (2S (CH₃)₂C)—6H between 1.20 and 1.80 ppm (M, 3CH₂ reminder of cyclohexane.

NMR no. 67-(b): 3H at 8.50 ppm (M, N⊕H₂ and CONH)—2H at 7.50 ppm (Se., NH₂ thiazol)—1H at 6.79 ppm (S, H thiazol)—1H at 5.99 ppm (D of D, J₁=9 Hz, J₂=4 Hz, H₇)—1H at 5.16 ppm (2D, J=13 Hz, CH₂OCO)—1H at 4.95 ppm (D, J=4 Hz H₆)—1H at 4.66 ppm (D, J=13 Hz, OCO)—1H at 3.92 ppm (D, J=17 Hz, CH₂SO)—1H at 3.58 ppm (D, J=17 Hz, CH₂SO)—1H at 3.36 ppm (M, CHN⊕H₂)—1H at 3.25 ppm (M, CH₂αN⊕H₂)—1H at 2.95 ppm (M, CH₂αN⊕H₂)—2H at 2.60 ppm (2D superposed CH₂CO₂)—3H at 1.70 ppm (M, H piperidine)—6H at 1.48 ppm (2S(CH₃)₂C)—3H at 1.45 ppm (M, H piperidine).

NMR no. 68-(b): 1H at 8.60 ppm (Se., N⊕H₂ piperidine)—1H at 8.45 ppm (Se., NH⊕₂ piperidine)—1H at 8.45 ppm (D, J=9 Hz, CONH)—1H at 7.50 ppm (Se., NH₂ thiazol)—1H at 6.70 ppm (S, H thiazol)—1H at 5.97 ppm (D of D, J₁=9 Hz, J₂=4 Hz, H₇)—1H at 5.10 ppm (D, J=13 Hz, CH₂OCO)—1H at 4.97 ppm (D, J=4 Hz, H₆) 1H at 4.63 ppm (D, J=13 Hz, CH₂OCO)—1H at 3.90 ppm (D, J=17 Hz, CH₂SO)—1H at 3.57 ppm (D, J=17 Hz, CH₂SO)—2H at 3.20 ppm (M, CH₂αN⊕H₂)—2H at 2.70 ppm (M, CH₂αN⊕H₂)—2H at 2.30 ppm (D, J=7 Hz, CH₂CO₂)—1H at 2.05 ppm (M, CHCH₂CO₂)—3H at 1.55 ppm (M, CH₂ piperidine)—6H at 1.48 ppm (2S, (CH₃)₂C)—1H at 1.20 ppm (M, CH₂ piperidine).

NMR no. 69-(b): 1H at 10.9 ppm (Se., ArNHCO)—1H at 8.45 ppm (D, J=9 Hz, CONH)—4H at 8.15 ppm (2S, CH₂N⊕H₃ and HAr 2′)—1H at 7.81 ppm (D, J=7 Hz, HAr 6′)—1H at 7.67 ppm (D, J=7 Hz, HAr 4′)—1H at 7.50 ppm (T, J=7 Hz, HAr 5′)—2H at 7.20 ppm (Se., NH₂ thiazol)—1H at 6.78 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.84 ppm (D, J=13 Hz, CH₂OCO)—1H at 4.00 ppm (D, J=17 Hz, CH₂SO)—1H at 3.75 ppm (M,

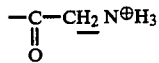

and CH₂SO)—6H 1.47 ppm (2S, (CH₃)₂C).

NMR no. 70-(b): 1H at 8.70 ppm (D, J=9 Hz, CONH)—3H at 8.50 ppm (Se., CH₂—N⊕H₃)—1H at 8.05 ppm (S, HAr 2′)—1H at 7.80 ppm (D, J=7 Hz, HAr 6′)—1H at 7.34 ppm (D, J=7 Hz HAr 5′)—1H at 6.95 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.05 ppm (D, J=4 Hz, H₆)—1H at 4.82 ppm (D, J=13 Hz, CH₂OCO)—3H at 4.05 ppm (M, ArCH₂N⊕H₃ and CH₂SO)—1H at 3.80 ppm (D, J=17 Hz, CH₂SO)—3H at 2.37 ppm (S, CH₃Ar)—6H at 1.48 ppm (2S, (CH₃)₂C).

NMR no. 71-(b): 1H at 8.70 ppm (D, J=9 Hz, CONH)—9H at 8.50 ppm (Se., CH₂N⊕H₃)—2H at 7.78 ppm (M, HAr 2′, 6′)—1H at 7.50 ppm (D, J=7 Hz, HAr 5′)—1H at 6.92 ppm (S, H thiazol)—1H at 6.00 ppm (D of D, J₁=9 Hz, J₂=4 Hz, H₇)—1H of 5.45 ppm (D, J=13 Hz, CH₂OCO)—1H of 5.00 ppm (D, J=4 Hz, H₆)—1H at 4.81 ppm (D, J=13 Hz, CH₂OCO)—3H at 4.05 ppm (M, ArCH₂N⊕H₃CH₂SO)—1H at 3.75 ppm (D, J=17 Hz, CH₂S0)—3H at 2.36 ppm (S, CH₃Ar)—6H at 1.47 ppm (2S, (CH₃)₂C).

NMR no. 72-(b): 1H at 8.70 ppm (D, J=9 Hz, CONH)—2H at 7.95 ppm (D, J=8 Hz, HAr 2′, 6′)—2H at 7.67 ppm (D, J=8 Hz, HAr 3′, 5′)—1H at 6.95 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.82 ppm (D, J=13 Hz, CH₂OCO)—2H at 4.16 ppm (M, ArCH₂NHCH₃)—1H at 4.08 ppm (D, J=17 Hz, CH₂SO)—1H at 3.78 ppm (D, J=17 Hz, CH₂SO)—3H at 2.43 ppm (S, CH₃N)—6H at 1.48 ppm (2S, (CH₃)₂C).

NMR no. 73-(b): 1H at 8.70 ppm (D, J=9 Hz, CONH)—2H at 7.95 ppm (D, J=8 Hz, HAr 2′, 6′)—2H at 7.67 ppm (D, J=8 Hz, HAr 3′, 5′)—1H at 6.92 ppm (S, H thiazol)—1H at 6.00 ppm (D of D, J₁=9 Hz, J₂=4 Hz, H₇)—1H at 5.43 ppm (D, J=13 Hz, CH₂OCO)—1H at 5.00 ppm (D, J=4 Hz, H₆)—1H at 4.82 ppm (D, J=13 Hz, CH₂OCO)—2H at 4.18 ppm (M, CH₂Ar)—1H at 4.10 ppm (D, J=17 Hz, CH₂SO)—1H at 3.76 ppm (D, J=17 Hz, CH₂SO)—2H at 2.90 ppm (M, CH₃CH₂NH)—6H at 1.47 ppm (2S, (CH₃)₂C)—3H at 1.16 ppm (T, J=7 Hz, CH₃CH₂).

NMR no. 74-(b): 1H at 8.70 ppm (D, J=9 Hz, CONH)—2H at 7.95 ppm (D, J=8 Hz, HAr 2′, 6′)—2H at 7.67 ppm (D, J=8 Hz, HAr 3′, 5′)—1H at 6.95 ppm (S, H thiazol)—1H 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.82 ppm (D, J=13 Hz, CH₂OCO)—2H at 4.16 ppm (M, ArCH₂NPr)—1H at 4.08 ppm (D, J=17 Hz, CH₂SO)—1H at 3.78 ppm (D, J=17 Hz, CH₂SO)—1H at 3.20 ppm (M, NH—CH(CH₃)₂)—6H at 1.48 ppm (2S, (CH₃)₂C)—6H at 1.26 ppm (D, J=7 Hz, (CH₃)₂CH).

NMR no. 75-(b): 1H at 8,62 ppm (D, J=9 Hz, CONH)—3H at 8,10 ppm (Se., CH₂N⊕H₃)—1H at 7,68 ppm (D, J=7 Hz, HAr 6′)—1H at 7,55 ppm (D, J=7 Hz, HAr 4′)—1H at 7,34 ppm (T, J=7 Hz, HAr 5′)—1H at 6,92 ppm (S, H thiazol)—1H at 6,00 ppm (D of D, J₁=9 Hz, J₂=4 Hz, H₇)—1H at 5,37 ppm (D, J=13 Hz, CH₂OCO)—1H at 5,00 ppm (D, J=4 Hz, H₆)—1H at 4,84 ppm (D, J=13 Hz, CH₂OCO)—3H at 4,10 ppm (M, CH₂N⊕H₃ et CH₂SO)—1H at 3,75 ppm (D, J=17 Hz, CH₂SO)—3H at 2,40 ppm (S, CH₃Ar)—6H at 1,47 ppm (2S, (CH₃)₂C).

NMR no. 76-(b): 1H at 8.62 ppm (D, J=9 Hz, CONH)—3H at 8.00 ppm (Se., CH₂N⊕H₃)—1H at 7.31 ppm (D, J=7 Hz, HAr 4′)—1H at 7.14 ppm (D, J=7 Hz, HAr 5′)—1H at 6.90 ppm (S, H thiazol)—1H at 6.00 ppm (D of D, J₁=9 Hz, J₂=4 Hz, H₇)—1H at 5.27 ppm (D, J=13 Hz, CH₂OCO)—1H at 5.00 ppm (D, J=4 Hz, H₆)—1H at 4.92 ppm (D, J=13 Hz, CH₂OCO)—3H at 4.00 ppm (M, CH₂N⊕H₃ et CH₂SO)—1H at 3.64 ppm (D, J=17 Hz, CH₂SO)—6H at 2.18 ppm (S, CH₃—Ar)—6H at 1.48 ppm (2S, (CH₃)₂C).

NMR no. 77 (b): 1H at 8.65 ppm (D, J=9 Hz, CONH)—3H at 7.90 ppm (Se., CH₂N⊕H₃)—1H at 7.00 ppm (S, HAr)—1H at 6.90 ppm (S, H thiazol)—1H at 6.00 ppm (D of D, J₁=9 Hz, J₂=4 Hz, H₇)—1H at 5.25 ppm (D, J=13 Hz, CH₂OCO)—1H at 5.00 ppm (D, J=4 Hz, H₆)—1H at 4.92 ppm (D, J=13 Hz, CH₂OCO)—3H at 4.00 ppm (M, ArCH₂N⊕H₃ and CH₂SO)—1H at 3.65 ppm (D, J=17 Hz, CH₂SO)—3H at 2.31 ppm (S, CH₃Ar)—3H at 2.25 ppm (S, CH₃Ar)—3H at 2.14 ppm (S, CH₃Ar)—6H at 1.45 ppm (2S, (CH₃)₂C).

NMR no. 78-(b): 1H at 8.70 ppm (D, J=9 Hz, CONH)—3H at 8.00 ppm (Se., CH₂N⊕H₃)—1H at 7.45 ppm (D, J=7 Hz, HAr 4′)—2H at 6.92 ppm (M, H thiazol and HAr 5′)—1H at 6.00 ppm (D of D, J₁=9 Hz, J₂=4 Hz, H₇)—1H at 5.42 ppm (D, J=13 Hz, CH₂OCO)—1H at 5.00 ppm (D, J=4 Hz, H₆)—1H at 4.84 ppm (D, J=13 Hz, CH₂OCO)—3H at 3.95 ppm (M, CH₂N⊕H₃ and CH₂SO)—3H at 3.78 ppm (S, OCH₃)—3H at 3.73 ppm (S, OCH₃)—1H at 3.58 ppm (D, J=17 Hz, CH₂SO)—6H at 1.47 ppm (2S, (CH₃)₂C).

NMR no. 79-(b): 1H at 8.62 ppm (D, J=9 Hz, CONH)—5H at 8.00 ppm (M, CH₂N⊕H₃ and HAr 2′, 6′)—1H at 7.20 ppm (D, J=7 Hz, HAr 5′)—1H at 6.95 ppm (S, H thiazol)—1H at 6.00 ppm (D of D, J₁=9 Hz, J₂=4 Hz, H₇)—1H at 5.45 ppm (D, J=13 Hz CH₂OCO)—1H at 5.00 ppm (D, J=4 Hz, H₆)—1H at 4.82 ppm (D, J=13 Hz, CH₂OCO)—3H at 4.00 ppm (M, CH₂N⊕H₃ and CH₂SO)—3H at 3.88 ppm (S, OCH₃)—1H at 3.72 ppm (D, J=17 Hz, CH$_2$SO)—3H at 1.48 ppm (S, (CH$_3$)$_2$C)—3H at 1.47 ppm (S, (CH$_3$)$_2$C).

NMR no. 80-(B): 1H at 8.66 ppm (D, J=9 Hz, CONH)—3H at 8.05 ppm (Se., CH$_2$N$^\oplus$H$_3$)—3H at 7.50 ppm (M, HAr)—1H at 6.95 ppm (S, H thiazol)—1H at 6.00 ppm (D of D J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.84 ppm (D, J=13 Hz, CH$_2$OCO)—3H at 4.00 ppm (M, CH$_2$N$^\oplus$H$_3$ et CH$_2$SO)—3H at 3.86 ppm (S, CH$_3$O—Ar)—1H at 3.75 ppm (D, J=17 Hz, CH$_2$SO)—3H at 1.48 ppm (S, (CH$_3$)$_2$C)—3H at 1.47 ppm (S, (CH$_3$)$_2$C).

NMR no. 81-(b): 1H at 8.82 ppm (D, J=9 Hz, CONH)—3H at 8.20 ppm (Se., CH$_2$N$^\oplus$H$_3$)—1H at 8.13 ppm (Se., HAr 2')—1H at 7.95 ppm (D, J=7 Hz, HAr 6')—1H at 7.69 ppm (D, J=7 Hz, HAr 4')—1H at 7.55 ppm (T, J=7 Hz, HAr 5')—1H at 6.95 ppm (S, H thiazol)—1H at 6.00 ppm (D of D, J$_1$=9 Hz, J$_2$=4 Hz, H$_7$)—1H at 5.48 ppm (D, J=13 Hz, CH$_2$OCO)—1H at 5.00 ppm (D, J=4 Hz, H$_6$) 1H at 4.86 ppm (D, J=13 Hz, CH$_2$OCO)—3H at 4.05 ppm (M, CH$_2$N$^\oplus$H$_3$ and CH$_2$SO)—1H at 3.75 ppm (D, J=17 Hz, CH$_2$SO)—4H at 2.40 ppm (M,

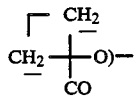

2H at 1.90 ppm (M,

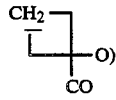

NMR no. 82-(b): 1H at 8.82 ppm (D, J=9 Hz, CONH)—3H at 8.20 ppm (Se., CH$_2$N$^\oplus$H$_3$)—2H at 7.80 ppm (M, HAr 2', 6')—1H at 7.45 ppm (D, J=7 Hz, HAr 5')—1H at 6.92 ppm (S, H thiazol)—1H at 5.97 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.82 ppm (D, J=13 Hz, CH$_2$OCO)—3H at 4.05 ppm (M, CH$_2$N$^\oplus$H$_3$ and CH$_2$SO)—1H at 3.75 ppm (D, J=17 Hz, CH$_2$SO)—4H at 2.40 ppm (M,

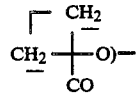

3H at 2.34 ppm (S, CH$_3$Ar)—2H at 1.90 ppm (M,

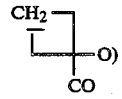

NMR no. 83-(b): 1H at 8.97 ppm (D, J=9 Hz, CONH)—2H at 8.79 ppm (Se., CH$_2$N$^\oplus$H$_2$)—2H at 8.00 ppm (D, J=8 Hz, HAr 2', 6')—2H at 7.58 ppm (D, J=8 Hz, HAr 3', 5')—1H at 6.95 ppm (S, H thiazol)—1H at 5.97 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.84 ppm (D, J=13 Hz, CH$_2$OCO)—2H at 4.19 ppm (M, CH$_2$N$^\oplus$H$_2$—CH$_3$)—1H at 4.08 ppm (D, J=17 Hz, CH$_2$SO)—1H at 3.75 ppm (D, J=17 Hz, CH$_2$SO)—3H at 2.50 ppm (M, CH$_2$N$^\oplus$H$_2$—CH$_3$)—4H at 2.40 ppm (M,

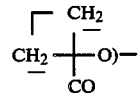

2H at 1.90 ppm (M,

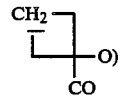

NMR no. 84(b): 1H at 10.7 ppm (S, CONHAr)—1H at 8.60 ppm (D, J=9 Hz, CONH)—1H at 8.20 ppm (S, HAr 2')—1H at 7.80 ppm (D, J=8 Hz, HAr 6')—3H at 7.65 ppm (Se., CH$_2$N+H$^3$)—1H at 7.60 ppm (D, J=8 Hz, HAr 4')—1H at 7.45 ppm (T, J=8 Hz, HAr 5')—1H at 6.92 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.84 ppm (D, J=13 Hz, CH$_2$OCO)—1H at 4.00 ppm (D, J=17 Hz, CH$_2$SO)—1H at 3.75 ppm (D, J=17 Hz, CH$_2$SO)—2H at 3.05 ppm (Q, J=7 Hz, CH$_2$CH$_2$N$^\oplus$H$_3$)—2H at 2.70 ppm (T, J=7 Hz, CH$_2$CH$_2$N$^\oplus$H$_3$)—6H at 1.47 ppm (2S, (CH$_3$)$_2$C).

NMR no. 85-(b): 1H at 8.80 ppm (D, J=9 Hz, CONH)—4H at 8.20 ppm (M, CH$_2$N$^\oplus$H$_3$ and H thiazol in 3)—1H 6.95 ppm (S, H thiazol)—1H at 6.00 ppm (D of D, J$_1$=9 Hz, J$_2$=4 Hz, H$_7$)—1H at 5.38 ppm (D, J=13 Hz, CH$_2$OCO)—1H at 4.98 ppm (D, J=4 Hz, H$_6$)—1H at 4.78 ppm (D, J=13 Hz, CH$_2$OCO)—1H at 3.98 ppm (D, J=17 Hz, CH$_2$SO)—2H at 3.82 ppm (Q, J=7 Hz, CH$_2$N$^\oplus$H$_3$)—1H at 3.66 ppm (D, J=17 Hz, CH$_2$SO)—6H at 1.49 ppm (2S, (CH$_3$)$_2$C).

NMR no. 86 (b): 1H at 10.75 ppm (S, ArNHCO)—1H at 8.70 ppm (D, J=9 Hz, CONH)—3H at 8.07 ppm (Se., CH$_2$N$^\oplus$H$_3$)—2H at 7.94 ppm (D, J=8 Hz, HAr 2' 6')—2H at 7.70 ppm (D, J=8 Hz, HAr 3' 5')—1H at 6.95 ppm (S, H thiazol)—1H at 6.00 ppm (D of D, J$_1$=9 Hz, J$_2$=4 Hz, H$_7$)—1H at 5.40 ppm (D, J=13 Hz, CH$_2$OCO)—1H at 4.98 ppm (D, J=4 Hz, H$_6$)—1H at 4.80 ppm (D, J=13 Hz, CH$_2$OCO)—1H at 4.05 ppm (D, J=17 Hz, CH$_2$SO)—3H at 3.80 ppm (M, CH$_2$SO and CH$_2$N$^\oplus$H$_3$)—6H at 1.48 ppm (2S, (CH$_3$)$_2$C).

NMR no. 87-(b): 1H at 8.75 ppm (D, J=9 Hz, CONH)—1H at 8.50 ppm (Se., NH$_2^\oplus$ piperidine)—1H at 8.40 ppm (Se., NH$_2^\oplus$ piperidine)—2H at 7.40 ppm (Se., NH$_2$ thiazol)—1H at 6.78 ppm (S, H thiazol)—1H at 5 95 ppm (D of D, J$_1$=9 Hz, J$_2$=4 Hz, H$_7$)—1H at 5.16 ppm (2D, J=13 Hz, CH$_2$OCO)—1H at 4.95 ppm (D, J=4 Hz, H$_6$)—1H at 4.68 ppm (D, J=13 Hz, CH$_2$OCO-)—1H at 3.92 ppm (D, J=17 Hz, CH$_2$SO)—1H at 3 60 ppm (D, J=17 Hz, CH$_2$SO)—1H at 3.40 ppm (M, CHN$^\oplus$H$_2$)—1H at 3.25 ppm (M, CH$_2$N$^\oplus$H$_2$)—1H at 2.89 ppm (M, CH$_2$N$^\oplus$H$_2$)—2H at 2.60 ppm (2D superposed, J=7 Hz, CH$_2$COO)—4H at 2.40 ppm (M,

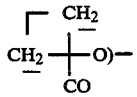

5H at 1.85 ppm (M, 3H of the piperidine and

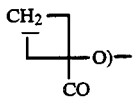

3H at 1.45 ppm (M, 3H piperidine).

NMR no. 88-(b): 1H at 8.80 ppm (D, J=9 Hz, CONH)—1H at 8.60 ppm (Se., N⊕H₂ piperidine)—1H at 8.45 ppm (Se., N⊕H₂ piperidine)—2H at 7.25 ppm (Se., NH₂ thiazol)—1H at 6.79 ppm (S, H thiazol)—1H at 6.00 ppm (D of D, J₁=9 Hz, J₂=4 Hz, H₇)—1H at 5.16 ppm (D, J=13 Hz, CH₂OCO)—1H at 5.00 ppm (D, J=4 Hz, H₆)—1H at 4.69 ppm (D, J=13 Hz, CH₂OCO)—1H at 3.90 ppm (D, J=17 Hz, CH₂SO)—1H at 3.60 ppm (D, J=17 Hz, CH₂SO)—2H at 3.24 ppm (M, CH₂ in α of N⊕H₂ piperidine)—2H at 2.70 ppm (M, CH₂ in α of N⊕H₂ piperidine)—6H at 2.40 ppm (M,

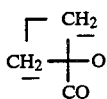

and CH₂COO)—6H between 1.5 and 2.2 ppm (M,

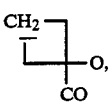

CHCH₂CO₂, 3H piperidine)—1H at 1.20 ppm (M, H piperidine).

NMR no. 89-(b): 1H at 8.80 ppm (D, J=9 Hz, CONH)—2H at 8.30 ppm (2 Se., NH₂⊕ piperidine)—2H at 7.40 ppm (Se., NH₂ thiazol)—1H at 6.78 ppm (S, H thiazol)—1H at 5.92 ppm (D of D, J₁=9 Hz, J₂=4 Hz, H₇)—1H at 5.14 ppm (D, J=13 Hz, CH₂OCO)—1H at 4.96 ppm (D, J=4 Hz, H₆)—1H at 4.60 ppm (D, J=13 Hz, CH₂OCO)—1H at 3.89 ppm (D, J=17 Hz, CH₂SO)—1H at 3.58 ppm (D, J=17 Hz, CH₂SO)—2H at 3.18 ppm (M, HαN⊕H₂ piperidine)—2H at 2.81 ppm (M, HαN⊕H₂ piperidine)—4H at 2.40 ppm (M,

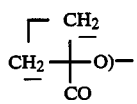

2H at 2.28 ppm (D, J=7 Hz, CH₂CO—O)—5H at 1.90 ppm (M,

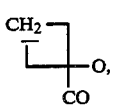

CHCH₂COO, 2HβN⊕H₂ piperidine) 2H at 1.30 ppm (M, 2HβN⊕H₂ piperidine).

NMR no. 90-(b): 1H at 8.45 ppm (D, J=9 Hz, CONH)—1H at 8.50 ppm (Se., NH₂⊕ piperidine)—1H at 8.20 ppm (Se., NH₂⊕ piperidine)—2H at 7.30 ppm (Se., NH₂ thiazol)—1H at 6.77 ppm (S, H thiazol)—1H 5.95 ppm (D of D, J₁=9 Hz, J₂=4 Hz, H₇)—1H at 5.11 ppm (D, J=13 Hz, CH₂OCO)—1H at 4.95 ppm (D, J=4 Hz, H₆)—1H at 4.61 ppm (D, J=13 Hz, CH₂OCO)—1H at 3.89 ppm (D, J=17 Hz, CH₂SO)—1H at 3.58 ppm (D, J=17 Hz, CH₂SO)—2H at 3.21 ppm (M, CH₂ and αN⊕H₂ piperidine)—2H at 2.81 ppm (M, CH₂ in αN⊕H₂ piperidine)—2H at 2.27 ppm (D, J=7 Hz, CH₂COO)—1H at 1.95 ppm (M, CHCH₂COO)—2H at 1.75 ppm (M, CH₂βN⊕H₂ piperidine)—6H at 1.47 ppm (2S, (CH₃)₂C)—2H at 1.40 ppm (M, CH₂βN+H₂ piperidine).

NMR no. 91-(b): 2H at 8.70 ppm (Se., CH₂N⊕H₂CH₃)—1H at 8.60 ppm (D, J=9 Hz, CONH)—1H at 8.10 ppm (Se., HAr 2')—1H at 7.96 ppm (D, J=8 Hz, Har 6')—1H at 7.75 ppm (D, J=8 Hz, HAr 4')—1H at 7.56 ppm (T, J=8 Hz, Har 5')—1H at 6.92 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.87 ppm (D, J=13 Hz, CH₂OCO)—2H at 4.16 ppm (M, ArCH₂N⊕H₂CH₃)—1H at 4.05 ppm (D, J=17 Hz, CH₂SO)—1H at 3.75 ppm (D, J=17 Hz, CH₂SO)—3H at 2.50 ppm (M, CH₃N⊕H₂CH₂)—6H at 1.45 ppm (2S, (CH₃)₂C).

NMR no. 92-(b): 2H at 8.70 ppm (Se., CH₂N⊕H₂CH₂CH₃)—1H at 8.60 ppm (D, J=9 Hz, CONH)—1H at 8.10 ppm (Se., HAr 2')—1H at 7.96 ppm (D, J=8 Hz, HAr 6')—1H at 7.75 ppm (D, J=8 Hz, HAr 4')—1H at 7.56 ppm (T, J=8 Hz, HAr 5')—1H at 6.92 ppm (S, H thiazol)—1H at 6.02 ppm (D of D, J₁=9 Hz, J₂=4 Hz, H₇) 1H at 5.45 ppm (D, J=13 Hz, CH₂OCO)—1H at 5.00 ppm (D, J=4 Hz, H₆)—1H at 4.87 ppm (D, J=13 Hz, CH₂OCO)—2H at 4.17 ppm (Se., Ar, CH₂N⊕H₂Et)—1H at 4.05 ppm (D, J=17 Hz, CH₂SO)—1H at 3.75 ppm (D, J=17 Hz, CH₂SO)—2H at 2.95 ppm (M, CH₃CH₂N⊕H₂)—6H at 1.45 ppm (2S, (CH₃)₂C)—3H at 1.15 ppm (T, J=7 Hz, CH₃CH₂N⊕H₂).

NMR no. 93(b): 1H at 8.75 ppm (D, J=9 Hz, CONH)—2H at 8.70 ppm (Se., CH₂N⊕H₂-i Pr)—1H at 8.10 ppm (Se., HAr 2')—1H at 7.95 ppm (D, J=8 Hz, HAr 6')—1H at 7.75 ppm (D, J=8 Hz, HAr 4')—1H at 7.58 ppm (T, J=8 Hz, HAr 5')—1H at 7.00 ppm (S, H thiazol)—1H at 6.00 ppm (D of D, J₁=9 Hz, J₂=4 Hz, H₇)—1H at 5.46 ppm (D, J=13 Hz, CH₂OCO)—1H at 5.00 ppm (D, J=4 Hz, H₆)—1H at 4.87 ppm (D, J=13 Hz, CH₂OCO)—2H at 4.19 ppm (M, ArCH₂N⊕H₂ i Pr)—1H at 4.05 ppm (D, J=17 Hz, CH₂SO)—1H at 3.79 ppm (D, J=17 Hz, CH₂SO)—1H at 3.31 ppm (M, (CH₃)₂—CH)—6H at 1.45 ppm (2S, (CH₃)₂C)—6H at 1.22 ppm (D, J=7 Hz, (CH₃)₂CHN⊕H₂).

NMR no. 94-(b): 1H at 8.90 ppm (D, J=9 Hz, CONH)—3H at 8.10 ppm (Se., CH₂N⊕H₃)—1H at 7.66 ppm (D, J=8 Hz, HAr 6')—1H at 7.55 ppm (D, J=8 Hz, HAr 4')—1H at 7.45 ppm (T, J=8 Hz, HAr 5')—1H at 6.95 ppm (S, H thiazol)—1H at 6.00 ppm (D of D, J₁=9 Hz, J₂=4 Hz, H₇)—1H at 5.40 ppm (D, J=13 Hz, CH₂OCO)—1H at 5.00 ppm (D, J=4 Hz, H₆)—1H at 4.86 ppm (D, J=13 Hz, CH₂OCO)—3H at 4.07 ppm (M, ArCH₂N⊕H₃ and CH₂SO)—1H at 3.67 ppm (D, J=17 Hz, CH₂SO)—3H at 2.40 ppm (S, CH₃Ar)—4H at 2.50 ppm (M,

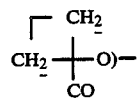

2H at 1.90 ppm (M,

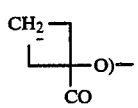

NMR no. 95-(b): 1H at 8.90 ppm (D, J=9 Hz, CONH)—3H at 8.05 ppm (Se., CH$_2$N$^\oplus$H$_3$)—1H at 7.40 ppm (D, J=8 Hz, HAr 4')—1H at 7.20 ppm (D, J=8 Hz, HAr 5')—1H at 6.95 ppm (S, H thiazol)—1H at 6.00 ppm (D of D, J$_1$=9 Hz, J$_2$=4 Hz, H$_7$)—1H at 5.30 ppm (D, J=13 Hz, CH$_2$OCO)—1H at 5.00 ppm (D, J=4 Hz, H$_6$)—1H at 4.95 ppm (D, J=13 Hz, CH$_2$OCO)—3H at 4.00 ppm (ArCH$_2$N$^\oplus$H$_3$ et CH$_2$SO)—1H at 3.63 ppm (D, J=17 Hz, CH$_2$SO)—4H at 2.40 ppm (M,

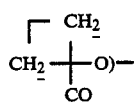

6H at 2.20 ppm (S, CH$_3$Ar)—2H at 1.90 ppm (M,

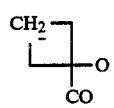

NMR no. 96-(b): 1H at 8.90 ppm (D, J=9 Hz, CONH)—3H at 7.90 ppm (Se., CH$_2$N$^\oplus$H$_3$)—1H at 7.00 ppm (S, HAr)—1H at 6.9 ppm (S, H thiazol)—1H at 6.00 ppm (D of D, J$_1$=9 Hz, J$_2$=4 Hz, H$_7$)—1H at 5.30 ppm (D, J=13 Hz, CH$_2$OCO)—1H at 5.00 ppm (D, J=4 Hz, H$_6$)—1H at 4.94 ppm (D, J=13 Hz, CH$_2$OCO)—3H at 4.00 ppm (M, ArCH$_2$N$^\oplus$H$_3$ et CH$_2$SO)—1H at 3.62 ppm (D, J=17 Hz, CH$_2$SO)—4H at 2.50 ppm (M,

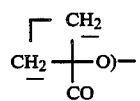

3H at 2.32 ppm (S, CH$_3$Ar)—3H at 2.2 ppm (S, CH$_3$Ar)—3H at 2.16 ppm (S, CH$_3$Ar)—2H at 1.90 ppm (M,

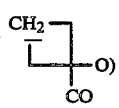

NMR no. 97-(b): 1H at 10.30 ppm (S, ArNHCO)—1H at 8.70 ppm (D, J=9 Hz, CONH)—1H at 8.30 ppm (Se., HAr 2')—3H at 8.05 ppm (M, CH$_2$N$^\oplus$H$_3$)—2H at 7.70 ppm (M, HAr 5', 6')—1H at 6.95 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 4.97 ppm (D, J=4 Hz, H$_6$)—1H at 4.80 ppm (D, J=13 Hz, CH$_2$OCO)—1H at 4.03 ppm (D, J=17 Hz, CH$_2$SO)—2H at 3.85 ppm (M, CH$_2$N$^\oplus$H$_3$)—1H at 3.75 ppm (D, J=17 Hz, CH$_2$SO)—6H at 1.47 ppm (2S, (CH$_3$)$_2$C).

NMR no. 98-(b): 1H at 9.90 ppm (S, ArNHCO)—1H at 8.66 ppm (D, J=9 Hz, CONH)—1H at 8.28 ppm (S, HAr 2')—5H at 7.70 ppm (M, HAr 5', 6' at CH$_2$N$^\oplus$H$_3$)—1H at 6.95 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.84 ppm (D, J=13 Hz, CH$_2$OCO)—1H at 4.03 ppm (D, J=17 Hz, CH$_2$SO)—1H at 3.68 ppm (D, J=17 Hz, CH$_2$SO)—2H at 3.05 ppm (M,

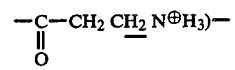

2H at 2.75 ppm (T, J=7 Hz,

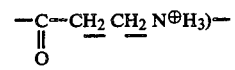

6H at 1.46 ppm (2S, (CH$_3$)$_2$C).

NMR no. 99-(b): 1H at 10.5 ppm (S, ArNHCO)—1H at 8.56 ppm (D, J=9 Hz, CONH)—2H at 7.89 ppm (D, J=8 Hz, HAr 2', 6')—2H at 7.70 ppm (D, J=8 Hz, HAr 3', 5')—3H at 7.70 ppm (Se., (CH$_2$)$_2$N$^\oplus$H$_3$)—1H at 6.95 ppm (S, H thiazol)—1H at 5.98 ppm (D of D, J$_1$=9 Hz, J$_2$=4 Hz, H$_7$)—1H at 5.40 ppm (D, J=13 Hz, CH$_2$OCO)—1H at 4.98 ppm (D, J=4 Hz, H$_6$)—1H at 4.79 ppm (D, J=13 Hz, CH$_2$OCO)—1H at 4.05 ppm (D, J=17 Hz, CH$_2$SO)—1H at 3.75 ppm (D, J=17 Hz, CH$_2$SO)—2H at 3.06 ppm (M,

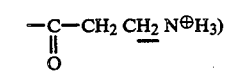

2H at 2.70 ppm (M,

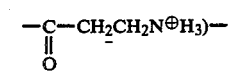

6H at 1.45 ppm (2S, (CH$_3$)$_2$C).

NMR no. 100-(b): 1H at 12.75 ppm (Se., thiazol NHCO)—1H at 8.90 ppm (D, J=9 Hz, CONH)—4H at 8.15 ppm (M, CH$_2$NH$_3$ and H thiazol in 3)—1H at 6.96 ppm (S, H thiazol)—1H at 6.00 ppm (D of D, J$_1$=9 Hz, J$_2$=4 Hz, H$_7$)—1H at 5.40 ppm (D, J=13 Hz, CH$_2$OCO)—1H at 4.98 ppm (D, J=4 Hz, H$_6$)—1H at 4.81 ppm (D, J=13 Hz, CH$_2$OCO)—1H at 4.0 ppm (D, J=17 Hz, CH$_2$SO)—2H at 3.86 ppm (M, CH$_2$N$^\oplus$H$_3$)—1H at 3.66 ppm (D, J=17 Hz, CH$_2$SO)—4H at 2.5 ppm (M,

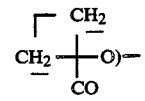

2H at 1.90 ppm (M,

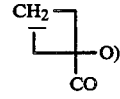

NMR no. 101-(b): 1H at 10.8 ppm (S, ArNHCO)—1H at 8.95 ppm (D, J=9 Hz, CONH)—3H at 8.15 ppm (Se., CH$_2$N$^\oplus$H$_3$)—2H at 7.90 ppm (D, J=8 Hz, HAr 2', 6')—2H at 7.70 ppm (D, J=8 Hz, HAr 3', 5')—1H at 6.97 ppm (S, H thiazol)—1H at 6.00 ppm (D of D, J$_1$=9 Hz, J$_2$=4 Hz, H$_7$)—1H at 5.36 ppm (D, J=13 Hz, CH$_2$OCO)—1H at 5.00 ppm (D, J=4 Hz, H$_6$)—1H at 4.82 ppm (D, J=13 Hz, CH$_2$OCO)—1H at 4.05 ppm (D, J=17 Hz, CH₂SO)—3H at 3.80 ppm (M, CH₂N⊕H₃ and CH₂SO)—4H at 2.40 ppm (M,

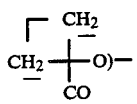

2H at 1.90 ppm (M,

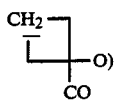

NMR no. 102-(b): 1H at 8.45 ppm (D, J=9 Hz, CONH)—3H at 8.0 ppm (Se., CH₂N⊕H₃)—1H at 6.79 ppm (S, H thiazol)—1H at 5.98 ppm (D of D, J₁=9 Hz, J₂=4 Hz, H₇)—1H at 5.15 ppm (2D, J=13 Hz, CH₂OCO) 1H at 4.97 ppm (D, J=4 Hz, H₆)—1H at 4.62 ppm (D, J=13 Hz, CH₂OCO)—1H at 4.15 ppm (De., J=12 Hz, H₂ Eq piperidine)—3H at 3.84 ppm (M, CH₂N⊕H₃ and CH₂SO)—2H at 3.58 ppm (M, CH₂SO and H₆ Eq piperidine)—1H at 3.05 ppm (Te., J=12 Hz, H₂ Ax piperidine)—1H at 2.81 ppm (Te., J=12 Hz, H₆ Ax piperidine)—1H at 2.60 ppm (M, CHCO₂)—2H at 1.84 ppm (M, H₃ and H₅ piperidine) 2H at 1.50 ppm (M, H₃ and H₅ piperidine)—6H at 1.45 ppm (2D, (CH₃)₂C).

NMR no. 103-(b): 1H at 8.72 ppm (D J=9 Hz, CONH)—3H at 8.25 ppm (Se., CH₂N⊕H₃)—3H at 7.75 ppm (M, HAr)—1H at 6.97 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.84 ppm (D, J=13 Hz, CH₂OCO)—3H at 4.05 ppm (M, CH₂N⊕H₃ and CH₂SO)—1H at 3.75 ppm (D, J=17 Hz, CH₂SO)—6H at 1.45 ppm (2S, (CH₃)₂C).

NMR no. 104-(b): 2H at 8.80 ppm (Se., CH₂N⊕H₂CH₃)—1H at 8.77 ppm (D, J=9 Hz, CONH)—3H at 7.75 ppm (M, HAr)—1H at 6.95 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.86 ppm (D, J=13 Hz, CH₂OCO)—2H at 4.25 ppm (M, CH₂N⊕H₂CH₃)—1H at 4.10 ppm (D, J=17 Hz, CH₂SO)—1H at 3.74 ppm (D, J=17 Hz, CH₂SO)—3H at 2.58 ppm (M, CH₂N⊕H₂—CH₃)—6H at 1.45 ppm (2S, (CH₃)₂C).

NMR no. 105-(b): 1H at 10.70 ppm (S, ArNHCO)—2H at 8.70 ppm (Se., CH₂N⊕H₂CH₃)—1H at 8.68 ppm (D, J=9 Hz, CONH)—1H at 8.16 ppm (S, HAr 2')—1H at 7.92 ppm (D, J=8 Hz, HAr 6')—1H at 7.66 ppm (D, J=8 Hz, HAr 4')—1H at 7.50 ppm (T, J=8 Hz, HAr 5')—1H at 6.95 ppm (S, H thiazol)—1H at 6.00 ppm (D of D, J₁=9 Hz, J₂=4 Hz, H₇)—1H at 5.45 ppm (D, J=13 Hz, CH₂OCO)—1H at 5.00 ppm (D, J=4 Hz, H₆)—1H at 4.82 ppm (D, J=13 Hz, CH₂OCO)—1H at 4.02 ppm (D, J=17 Hz, CH₂SO)—2H at 3.90 ppm (M, CH₂N⊕HCH₃)—1H at 3.74 ppm (D, J=17 Hz, CH₂SO)—3H at 2.60 ppm (M, CH₂N⊕H₂CH₃)—6H at 1.45 ppm (2S, (CH₃)₂C).

NMR no. 106-(b): 1H at 10.80 ppm (S, ArNHCO)—3H at 8.70 ppm (M, CH₂N⊕H₂CH₃ et CONH)—2H at 7.92 ppm (D, J=8 Hz, HAr 2', 6')—2H at 7.69 ppm (D, J=8 Hz, HAr 3', 5')—1H at 6.95 ppm (S, H thiazol)—1H at 6.00 ppm (D of D, J₁=9 Hz, J₂=4 Hz, H₇)—1H at 5.42 ppm (D, J=13 Hz, CH₂OCO)—1H at 5.00 ppm (D, J=4 Hz, H₆)—1H at 4.81 ppm (D, J=13 Hz, CH₂OCO)—1H at 4.05 ppm (D, J=17 Hz, CH₂SO)—2H at 3.95 ppm (M, CH₂N⊕H₂CH₃)—1H at 3.75 ppm (D, J=17 Hz, CH₂SO)—3H at 2.62 ppm (M, CH₂N⊕H₂CH₃)—6H at 1.45 ppm (2S, (CH₃)₂C).

NMR no. 107-(b): 1H at 9.95 ppm (S, ArNHCO)—1H at 8.75 ppm (D, J=9 Hz, CONH)—3H at 8.05 ppm (Se., CH₂N⊕H₃)—1H at 7.61 ppm (D, J=8 Hz, HAr 6')—1H at 7.52 ppm (D, J=8 Hz, HAr 4')—1H at 7.31 ppm (T, J=8 Hz, HAr 6')—1H at 6.96 ppm (S, H thiazol)—1H at 6.00 ppm (D of D, J₁=9 Hz, J₂=4 Hz, H₇)—1H at 5.40 ppm (D, J=13 Hz, CH₂OCO)—1H at 5.00 ppm (D, J=4 Hz, H₆)—1H at 4.81 ppm (D, J=13 Hz, CH₂OCO)—1H at 4.05 ppm (D, J=17 Hz, CH₂SO)—2H at 3.81 ppm (M, CH₂N⊕H₃)—1H at 3.72 ppm (D, J=17 Hz, CH₂SO)—3H at 2.28 ppm (S, ArCH₃)—6H at 1.45 ppm (2S, (CH₃)₂C).

NMR no. 108-(b): 1H at 9.75 ppm (S, ArNHCO)—1H at 8.70 ppm (D, J=9 Hz, CONH)—3H at 7.70 ppm (Se., CH₂CH₂N⊕H₃)—1H at 7.60 ppm (D, J=8 Hz, HAr 6')—1H at 7.50 ppm (D, J=8 Hz, HAr 4')—1H at 7.25 ppm (T, J=8 Hz, HAr 5')—1H at 6.95 ppm (S, H thiazol)—1H at 6.00 ppm (D of D, J₁=9 Hz, J₂=4 Hz, H₇)—1H at 5.39 ppm (D, J=13 Hz, CH₂OCO)—1H at 5.00 ppm (D, J=4 Hz, H₆)—1H at 4.82 ppm (D, J=13 Hz, CH₂OCO)—1H at 4.05 ppm (D, J=17 Hz, CH₂SO)—1H at 3.72 ppm (D, J=17 Hz, CH₂SO)—2H at 3.02 ppm (M, CH₂CH₂N⊕H₃)—2H at 2.69 ppm (T, J=7, CH₂CH₂N⊕H₃)—3H at 2.29 ppm (S, ArCH₃)—6H at 1.45 ppm (2S, (CH₃)₂C).

NMR no. 109-(b): 1H at 12.7 ppm (Se., NHCO thiazol)—1H at 8.79 ppm (D, J=9 Hz, CONH)—1H at 8.08 ppm (S, H thiazol in 3)—3H at 7.75 ppm (Se., CH₂N⊕H₃)—1H at 6.98 ppm (S, H thiazol)—1H at 6.00 ppm (D of D, J₁=9 Hz, J₂=4 Hz, H₇)—1H at 5.37 ppm (D, J=13 Hz CH₂OCO)—1H at 5.00 ppm (D, J=4 Hz, H₆)—1H at 4.81 ppm (D, J=13 Hz, CH₂OCO)—1H at 4.03 ppm (D, J=17 Hz, CH₂SO)—1H at 3.68 ppm (D, J=17 Hz, CH₂SO)—2H at 3.06 ppm (M, CH₂CH₂N⊕H₃)—2H at 2.77 ppm (T, J=7 Hz, CH₂CH₂N⊕H₃)—6H at 1.45 ppm (2S, (CH₃)₂C).

NMR no. 110-(b): 1H at 8.70 ppm (D, J=9 Hz, CONH)—5H at 7.96 ppm (M, HAr 2', 6' and CH₂N⊕H₃)—2H at 7.55 ppm (D, J=8 Hz, HAr 3', 5')—1H at 6.95 ppm (S, H thiazol)—1H at 6.00 ppm (D of D, J₁=9 Hz, J₂=4 Hz, H₇)—1H at 5.46 ppm (D, J=13 Hz, CH₂OCO)—1H at 4.99 ppm (D, J=4 Hz, H₆)—1H at 4.84 ppm (D, J=13 Hz, CH₂OCO)—1H at 4.06 ppm (D, J=17 Hz, CH₂SO)—1H at 3.74 ppm (D, J=17 Hz, CH₂SO)—2H at 3.55 ppm (Se., CH₂N⊕H₃)—3H at 3.25 ppm (Se., NCH₃)—6H at 1.45 ppm (2S, (CH₃)₂C).

NMR no. 111-(b): 1H at 10.5 ppm (Se., ArNHCO)—1H at 8.95 ppm (D, J=9 Hz, CONH)—2H at 7.89 ppm (D, J=8 Hz, HAr 2', 6')—2H at 7.71 ppm (D, J=8 Hz, HAr 3', 5')—1H at 6.96 ppm (S, H thiazo)—1H at 5.98 ppm (D of D, J₁=9 Hz, J₂=4 Hz, H₇)—1H at 5.42 ppm (D, J=13 Hz, CH₂OCO)—1H at 5.00 ppm (D, J=4 Hz, H₆)—1H at 4.80 ppm (D, J=13 Hz, CH₂OCO)—1H at 4.05 ppm (D, J=17 Hz, CH₂SO)—1H at 3.75 ppm (D, J=17 Hz, CH₂SO)—2H at 3.05 ppm (M, CH₂CH₂N⊕H₃)—2H at 2.70 ppm (T, J=7 Hz, CH₂CH₂N⊕H₃)—4H at 2.40 ppm (M,

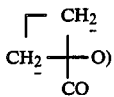

2H at 1.90 ppm (M,

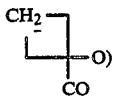

NMR no. 112-(b): 1H at 8.80 ppm (D, J=9 Hz, CONH)—3H at 7.90 ppm (Se., CH$_2$N$^\oplus$H$_3$)—1H at 6.80 ppm (S, H thiazol)—1H at 5.95 ppm (D of D, J$_1$=9 Hz, J$_2$=4 Hz, H$_7$)—1H at 5.17 ppm (2D, J=13 Hz, CH$_2$OCO)—1H at 4.96 ppm (D, J=4 Hz, H$_6$)—1H at 4.60 ppm (D, J=13 Hz, CH$_2$OCO)—1H at 4.18 ppm (M, H$_{2e}$ piperidine) 3H at 3.90 ppm (M, CH$_2$N$^\oplus$H$_3$ and CH$_2$SO)—2H at 3.58 ppm (M, CH$_2$SO et H$_{6e}$ piperidine)—1H at 3.06 ppm (M, H$_{2a}$ piperidine)—1H at 2.75 ppm (M, H$_{6a}$ piperidine)—1H at 2.60 ppm (M, H$_4$ piperidine)—4H at 2.40 ppm (M,

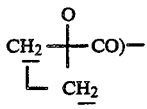

4H at 1.80 ppm et 2H 1.50 ppm

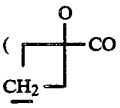

et H$_3$ et H$_5$ piperidine).

NMR no. 113-(b): 1H at 8.75 ppm (D, J=9 Hz, CONH)—3H at 8.40 ppm (Se., CHN$^\oplus$H$_3$)—1H at 8.13 ppm (S, HAr 6')—1H at 8.00 ppm (D, J=8 Hz, HAr 2')—1H at 7.64 ppm (D, J=8 Hz, HAr 3')—1H at 6.97 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.86 ppm (D, J=13 Hz, CH$_2$OCO)—2H at 4.19 ppm (M, CH$_2$N$^\oplus$H$_3$)—1H at 4.10 ppm (D, J=17 Hz, CH$_2$SO)—1H at 3.76 ppm (D, J=17 Hz, CH$_2$SO)—6H at 1.45 ppm (2S, (CH$_3$)$_2$C).

NMR no. 114-(b): 1H at 8.72 ppm (D, J=9 Hz, CONH)—3H at 8.40 ppm (Se., CH$_2$N$^\oplus$H$_3$)—2H at 8.11 ppm (M, HAr 2', 6')—1H at 7.86 ppm (M, HAr 3')—1H at 6.99 ppm (S, H thiazol)—1H at 6.01 ppm (D of D, J$_1$=9 Hz, J$_2$=4 Hz, H$_7$)—1H at 5.46 ppm (D, J=13 Hz, CH$_2$OCO)—1H at 5.00 ppm (D, J=4 Hz, H$_6$)—1H at 4.89 ppm (D, J=13 Hz, CH$_2$OCO)—2H at 4.18 ppm (M, CH$_2$N$^\oplus$H$_3$)—1H at 4.06 ppm (D, J=17 Hz, CH$_2$SO)—1H at 3.78 ppm (D, J=17 Hz, CH$_2$SO)—6H at 1.45 ppm (2S, (CH$_3$)$_2$C).

NMR no. 115-(b): 1H at 10.20 ppm (Se., ArNH CO)—1H at 8.70 ppm (D, J=9 Hz, CONH)—1H at 8.16 ppm (Se., HAr 2')—1H at 7.84 ppm (D, J=8 Hz, HAr 6')—3H at 7.66 ppm (Se., CH$_2$N$^\oplus$H$_3$)—1H at 7.60 ppm (D, J=8 Hz, HAr 4')—1H at 7.45 ppm (T, J=8 Hz, HAr 5')—1H at 6.97 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.84 ppm (D, J=13 Hz, CH$_2$OCO)—1H at 4.05 ppm (D, J=17 Hz, CH$_2$SO)—1H at 3.75 ppm (D, J=17 Hz, CH$_2$SO)—2H at 2.81 ppm (M, CH$_2$—N$^\oplus$H$_3$)—2H at 2.40 ppm (T, J=7 Hz, CH$_2$CO$_2$)—2H at 1.82 ppm (M, CH$_2$CH$_2$CO$_2$)—6H at 1.45 ppm (2S, (CH$_3$)$_2$C).

NMR no. 116-(b): 1H at 10.3 ppm (Se., ArNH CO)—1H at 8.70 ppm (D, J=9 Hz, CONH)—2H at 7.90 ppm (D, J=8 Hz, HAr 2', 6')—1H at 7.67 ppm (D, J=8 Hz, HAr 3', 5')—3H at 7.60 ppm (Se., CH$_2$N$^\oplus$H$_3$)—1H at 6.95 ppm (S, H thiazol)—1H at 6.00 ppm (D of D, J$_1$=9 Hz, J$_2$=4 Hz, H$_7$)—1H at 5.42 ppm (D, J=13 Hz CH$_2$OCO)—1H at 4.98 ppm (D, J=4 Hz, H$_6$)—1H at 4.79 ppm (D, J=13 Hz, CH$_2$OCO)—1H at 4.06 ppm (D, J=17 Hz, CH$_2$SO)—1H at 3.75 ppm (D, J=17 Hz, CH$_2$SO)—2H at 2.79 ppm (M, CH$_2$N$^\oplus$H$_3$)—2H at 2.42 ppm (M, CH$_2$—CONHAr)—2H at 1.84 ppm (M, CH$_2$CH$_2$N$^\oplus$H$_3$)—6H at 1.48 ppm (2S, (CH$_3$)$_2$C).

NMR no. 117-(b): 1H at 10.30 ppm (Se., ArNH CO)—1H at 8.75 ppm (D, J=9 Hz, NHCO)—2H at 7.84 ppm (D, J=8 Hz, HAr 2', 6')—2H at 7.72 ppm (D, J=8 Hz, HAr 3', 5')—3H at 7.60 ppm (Se., CH$_2$N$^\oplus$H$_3$)—1H at 6.97 ppm (S, H thiazol)—1H at 6.00 ppm (D of D, J$_1$=9 Hz, J$_2$=4 Hz, H$_7$)—1H at 5.40 ppm (D, J=13 Hz, CH$_2$OCO)—1H at 4.90 ppm (D, J=4 Hz, H$_6$)—1H at 4.78 ppm (D, J=13 Hz, CH$_2$OCO)—1H at 4.05 ppm (D, J=17 Hz, CH$_2$SO)—1H at 3.75 ppm (D, J=17 Hz, CH$_2$SO)—2H at 2.75 ppm (M, CH$_2$N$^\oplus$H$_3$)—2H at 2.36 ppm (M, CH$_2$CONHAr)—4H at 1.58 ppm (M, —COCH$_2$(CH$_2$)$_2$CH$_2$N$^\oplus$H$_3$)—6H at 1.45 ppm (2S, (CH$_3$)$_2$C).

NMR no. 118-(b): 1H at 12.7 ppm (Se, NHCO thiazol)—1H at 8.65 ppm (D, J=9 Hz, CONH)—3H at 8.20 ppm (Se, CH$_2$N$^\oplus$H$_3$)—1H at 6.93 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.02 ppm (D, J=4 Hz, H$_6$)—1H at 4.75 ppm (D, J=13 Hz, CH$_2$OCO)—1H at 4.02 ppm (D, J=17 Hz, CH$_2$SO)—2H at 3.90 ppm (M, CH$_2$Gly)—1H at 3.70 ppm (D, J=17 Hz, CH$_2$SO)—3H at 2.50 ppm (S, CH$_3$ thiazol—6H at 1.45 ppm (2S, (CH$_3$)$_2$C).

NMR no. 119-(b): 1H at 8.45 ppm (D, J=9 Hz, CONH)—3H at 7.80 ppm (Se., CH—N$^\oplus$H$_3$)—1H at 6.80 ppm (S, H thiazol)—1H at 6.00 ppm (D of D, J$_1$=9 Hz, J$_2$=4 Hz, H$_7$)—1H at 5.10 ppm (D, J=13 Hz, CH$_2$OCO)—1H at 4.95 ppm (D, J=4 Hz, H$_6$)—1H at 4.58 ppm (D, J=13 Hz, CH$_2$OCO)—1H at 3.90 ppm (D, J=17 Hz, CH$_2$SO)—1H at 3.56 ppm (D, J=17 Hz, CH$_2$SO)—1H at 3.00 ppm (2M, CHN$^\oplus$H$_3$)—1H at 2.25 ppm (M, CHCO$_2$)—4H at 1.80 ppm and 4H at 1.40 ppm (M, CH$_2$ cyclohexane)—6H at 1.44 ppm (2S, (CH$_3$)$_2$C).

NMR no. 120-(b): 1H at 8.75 ppm (D, J=9 Hz, CONH)—2H at 7.80 ppm (Se., HAr 2', 6')—3H at 7.65 ppm (Se., CH$_2$N$^\oplus$H$_3$)—1H at 7.57 ppm (D, J=8 Hz HAr 4')—1H at 7.47 ppm (T, J=8 Hz, HAr 5')—1H at 7.00 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 4.98 ppm (D, J=4 Hz, H$_6$)—1H at 4.82 ppm (D, J=13 Hz, CH$_2$OCO)—1H at 4.05 ppm (D, J=17 Hz, CH$_2$SO)—1H at 3.75 ppm (D, J=17 Hz, CH$_2$SO)—3H at 3.00 ppm (M,

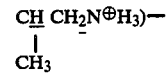

6H at 1.50 ppm (2S, (CH$_3$)$_2$C)—3H at 1.20 ppm (D, J=7 Hz,

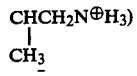

NMR no. 121-(b): 1H at 10.0 ppm (Se., ArNH CO)—1H at 8.85 ppm (D, J=9 Hz, CONH)—3H at 8.05 ppm (Se., CH$_2$N$^⊕$H$_3$)—1H at 7.45 ppm (S, HAr 6')—1H at 7.30 ppm (S, HAr 4')—1H at 7.00 ppm (S, H thiazol)—1H at 6.00 ppm (D of D, J$_1$=9 Hz, J$_2$=4 Hz, H$_7$)—1H at 5.43 ppm (D, J=13 Hz, CH$_2$OCO)—1H at 5.00 ppm (D, J=4 Hz, H$_6$)—1H at 4.78 ppm (D, J=13 Hz, CH$_2$OCO)—1H at 4.05 ppm (D, J=17 Hz, CH$_2$SO)—2H at 3.80 ppm (M, CH$_2$Gly)—1H at 3.75 ppm (D, J=17 Hz, CH$_2$SO)—6H at 2.25 ppm (2S, CH$_3$Ar)—6H at 1.50 ppm (2S, (CH$_3$)$_2$C).

NMR no. 122-(b): 1H at 10.45 ppm (Se., ArNH CO)—1H at 8.70 ppm (D, J=9 Hz, CONH)—1H at 8.50 ppm (Se., N$^⊕$H$_2$, piperidine)—1H at 8.20 ppm (Se., N$^⊕$H$_2$, piperidine)—2H at 7.84 ppm (D, J=8 Hz, HAr 2', 6')—2H at 7.70 ppm (D, J=8 Hz, HAr 3', 5')—1H at 6.98 ppm (S, H thiazol)—1H at 6.00 ppm (D of D, J$_1$=9 Hz, J$_2$=4 Hz, H$_7$)—1H at 5.42 ppm (D, J=13 Hz, CH$_2$OCO)—1H at 4.98 ppm (D, J=4 Hz, H$_6$)—1H at 4.78 ppm (D, J=13 Hz, CH$_2$OCO)—1H at 4.05 ppm (D, J=17 Hz, CH$_2$SO)—1H at 3.75 ppm (D, J=17 Hz, CH$_2$SO)—2H at 3.30 ppm (M, CH$_2$ in αN$^⊕$H$_2$ piperidine)—2H at 2.90 ppm (M, CH$_2$ in αN$^⊕$H$_2$ piperidine)—1H at 2.66 ppm (M, CHCONH)—4H at 1.80 ppm (M, CH$_2$ in βN$^⊕$H$_2$ piperisine)—6H at 1.45 ppm (2S, (CH$_3$)$_2$C).

NMR no. 123-(b): 1H at 10.25 ppm (Se., ArNH CO)—1H at 8.70 ppm (D, J=9 Hz, CONH)—1H at 8.50 ppm (Se., N$^⊕$H$_2$, piperidine)—1H at 8.25 ppm (Se, N$^⊕$H$_2$, piperidine)—1H at 8.19 ppm (Se, HAr 2')—1H at 7.86 ppm (D, J=8 Hz, HAr 6')—1H at 7.60 ppm (D, J=8 Hz, HAr 4')—1H at 7.42 ppm (T, J=8 Hz, HAr 5')—1H at 6.95 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.81 ppm (D, J=13 Hz, CH$_2$OCO)—1H at 4.05 ppm (D, J=17 Hz, CH$_2$SO)—1H at 3.71 ppm (D, J=17 Hz, CH$_2$SO)—2H at 3.30 ppm (M, CH$_2$ in αN$^⊕$H$_2$ Piperidine)—2H at 2.90 ppm (M, CH$_2$ in αN$^⊕$H$_2$ piperidine)—1H at 2.66 ppm (M, CHCONH)—4H at 1.80 ppm (M, CH$_2$ in βN$^⊕$H$_2$ piperidine)—6H at 1.45 ppm (2S, (CH$_3$)$_2$C).

NMR no. 124-(b): 1H at 10.75 ppm (Se., ArNH CO)—1H at 8.80 ppm (D, J=9 Hz, CONH)—3H at 8.20 ppm (Se., CHN$^⊕$H$_3$)—2H at 7.92 ppm (D, J=8 Hz, HAr 2', 6')—2H at 7.70 ppm (D, J=8 Hz, HAr 3', 5')—1H at 7.00 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.80 ppm (D, J=13 Hz, CH$_2$OCO)—2H at 4.00 ppm (M, HαAla and CH$_2$SO)—1H at 3.75 ppm (D, J=17 Hz, CH$_2$SO)—6H at 1.50 ppm (2S, (CH$_3$)$_2$C)—3H at 1.42 ppm (D, J=7 Hz, CH$_3$Ala).

NMR no. 125-(b): 1H at 10.80 ppm (Se., ArNH CO)—1H at 9.00 ppm (D, J=9 Hz, CONH)—3H at 8.20 ppm (Se., CH—N$^⊕$H$_3$)—2H at 7.85 ppm (D, J=8 Hz, HAr 2', 6')—2H at 7.75 ppm (D, J=8 Hz, HAr 3', 5')—1H at 7.00 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.80 ppm (D, J=13 Hz, CH$_2$OCO)—2H at 4.00 ppm (M, HαAla and CH$_2$SO)—1H at 3.75 ppm (D, J=17 Hz, CH$_2$SO)—4H at 2.40 ppm (M,

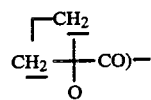

2H at 1.80 ppm (M,

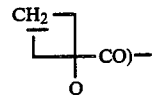

3H at 1.43 ppm (D, J=7 Hz, CH$_3$Ala).

NMR no. 126-(b): 1H at 8.45 ppm (D, J=9 Hz, CONH)—3H at 8.00 ppm (Se., N$^⊕$H$_3$Ala)—3H at 7.90 ppm (Se., N$^⊕$H$_3$ thiazol)—1H at 6.80 ppm (S, H thiazol)—1H at 6.00 ppm (D of D, J$_1$=9 Hz, J$_2$=4 Hz, H$_7$)—1H at 5.20 ppm (M, CH$_2$OCO)—1H at 4.95 ppm (D, J=4 Hz, H$_6$)—1H at 4.50 ppm (D, CH$_2$OCO)—1H at 3.15 ppm (M, H$_2$a piperidine)—1H at 2.80 ppm (M, H$_6$a piperidine)—1H at 2.60 ppm (M, —CHCO$_2$ piperidine)—2H at 1.80 ppm et 2H at 1.50 ppm (2M, H$_3$ and H$_5$ piperidine)—6H at 1.45 ppm (2S, (CH$_3$)$_2$C)—3H at 1.20 ppm (2D, CH$_3$CH).

NMR no. 127-(b): 1H at 8.43 ppm (D, J=9 Hz, CONH)—6H at 7.50 ppm (Se., N$^⊕$H$_3$)—1H at 6.80 ppm (S, H thiazol)—1H at 6.00 ppm (D of D, J$_1$=9 Hz, J$_2$=4 Hz, H$_7$)—1H at 5.16 ppm (2D, J=13 Hz, CH$_2$OCO-)—1H at 4.95 ppm (D, J=4 Hz, H$_6$)—1H at 4.58 ppm (D, J=13 Hz, CH$_2$OCO)—1H at 4.20 ppm (M, H$_2$e piperidine)—1H at 3.90 ppm (D, J=17 Hz, CH$_2$SO)—1H at 3.64 ppm (M, H$_6$e piperidine)—1H at 3.57 ppm (D, J=17 Hz, CH$_2$SO)—1H at 3.07 ppm (M, H$_2$a piperidine)—2H at 2.96 ppm (M, CH$_2$N$^⊕$H$_3$)—1H at 2.75 ppm (M, H$_6$a piperidine)—3H at 2.65 ppm (M, CHCO$_2$ and CH$_2$CON)—2H at 1.80 ppm et 2H at 1.50 ppm (H$_3$ and H$_5$ piperidine)—6H at 1.45 ppm (2S, (CH$_3$)$_2$C).

NMR no. 128-(b): 1H at 8.45 ppm (D, J=9 Hz, CONH)—6H at 7.70 ppm (Se., N$^⊕$H$_3$)—1H at 6.80 ppm (S, H thiazol)—1H at 5.98 ppm (D de D, J$_1$=9 Hz, J$_2$=4 Hz, H$_7$)—1H at 5.20 ppm (2D, J=13 Hz, CH$_2$OCO)—1H at 4.96 ppm (D, J=4 Hz, H$_6$)—1H at 4.58 ppm (D, J=13 Hz, CH$_2$OCO)—1H at 4.18 ppm (H$_2$e piperidine)—1H at 3.90 ppm (D, J=17 Hz, CH$_2$SO)—1H at 3.75 ppm (M, H$_6$e piperidine)—1H at 3.55 ppm (D, J=17 Hz, CH$_2$SO)—1H at 3.00 ppm (M, H$_2$a piperidine)—4H at 2.65 ppm (M, CH$_2$N$^⊕$H$_3$, H$_6$a et H$_4$ piperidine)—2H at 2.40 ppm (T, CH$_2$CON)—4H at 1.70 ppm (M, CHCH$_2$CH$_2$N$^⊕$H$_3$, H$_3$ and H$_5$ piperidine)—2H at 1.50 ppm (M, H$_3$ and H$_5$ piperidine)—6H at 1.44 ppm (2S, (CH$_3$)$_2$C).

NMR no. 129-(b): 1H at 8.50 ppm (Se., N$^⊕$H$_2$ piperidinium)—1H at 8.45 ppm (D, J=9 Hz, CONH)—1H at 8.25 ppm (Se., N$^⊕$H$_2$ piperidinium)—3H at 7.40 ppm (Se., N$^⊕$H$_3$ thiazol)—1H at 6.80 ppm (S, H thiazol)—1H at 6.00 ppm (D of D, J$_1$=9 Hz, J$_2$=4 Hz, H$_7$)—1H at 5.16 ppm (D, J=13 Hz, CH$_2$OCO)—1H at 4.15 ppm (M, H$_2$e piperidine)—2H at 3.90 ppm (M, H$_6$e piperidine and CH$_2$SO)—1H at 3.55 ppm (D, J=17 Hz, CH$_2$SO)—2H at 3.25 ppm (M, H$_2$e and H$_6$e piperidinium)—1H at 3.15 ppm (M, H$_2$a piperidine)—3H at 2.85 ppm (M, H$_6$a piperidine and H$_2$a and H$_6$a piperidinium)—2H at 2.70 ppm (M, H$_4$ piperidine and H$_4$ piperidinium)—6H at 1.75 ppm and 2H at 1.50 ppm (2M, H$_3$ and H$_5$ piperidinium H$_3$ and H$_5$ piperidine)—6H at 1.44 ppm (2S, (CH$_3$)$_2$C).

NMR no. 130-(b): 1H at 8.75 ppm (D, J=9 Hz, CONH)—3H at 8.20 ppm (Se., CH$_2$N$^{\oplus}$H$_3$)—1H at 7.80 ppm (D, J=8 Hz, HAr 6')—2H at 7.45 ppm (M, HAr 3', 5') 1H at 7.00 ppm (S, H thiazol)—1H at 6.00 ppm (D of D, J$_1$=9 Hz, J$_2$=4 Hz, H$_7$)—1H at 5.42 ppm (D, J=13 Hz, CH$_2$OCO)—1H at 5.00 ppm (D, J=4 Hz, H$_6$)—1H at 4.80 ppm (D, J=13 Hz, CH$_2$OCO)—3H at 4.00 ppm (M, CH$_2$N$^{\oplus}$H$_3$ and CH$_2$SO)—1H at 3.75 ppm (D, J=17 Hz, CH$_2$SO)—3H at 2.45 ppm (S, CH$_3$Ar)—6H at 1.45 ppm (2S, (CH$_3$)$_2$C).

NMR no. 131-(b): 1H at 8.85 ppm (D, J=9 Hz, CONH)—3H at 8.20 ppm (Se., CH$_2$N$^{\oplus}$H$_3$)—1H at 7.80 ppm (D, J=8 Hz, HAr 6')—2H at 7.45 ppm (M, HAr 3', 5')—1H at 6.95 ppm (S, H thiazol)—1H at 6.00 ppm (D of D, J$_1$=9 Hz, J$_2$=4 Hz, H$_7$)—1H at 5.45 ppm (D, J=13 Hz, CH$_2$OCO)—1H at 5.00 ppm (D, J=4 Hz, H$_6$)—1H at 4.80 ppm (D, J=13 Hz, CH$_2$OCO)—3H at 4.00 ppm (M, CH$_2$N$^{\oplus}$H$_3$ et CH$_2$SO)—1H at 3.73 ppm (D, J=17 Hz, CH$_2$SO)—3H at 2.50 ppm (S, CH$_3$Ar)—4H at 2.40 ppm (M,

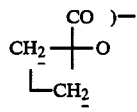

2H at 1.80 ppm (M,

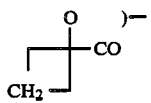

NMR no. 132-(b): 1H at 8.80 ppm (D, J=9 Hz, CONH)—3H at 8.10 ppm (Se., CH$_2$N$^{\oplus}$H$_3$)—1H at 7.55 ppm (S, HAr)—1H at 7.45 ppm (S, HAr)—1H at 7.00 ppm (S, H thiazol)—1H at 6.00 ppm (D of D, J$_1$=9 Hz, J$_2$=4 Hz, H$_7$)—1H at 5.40 ppm (D, J=13 Hz, CH$_2$OCO)—1H at 5.00 ppm (D, J=4 Hz, H$_6$)—1H at 4.83 ppm (D, J=13 Hz, CH$_2$OCO)—3H at 3.70 ppm (M, CH$_2$N$^{\oplus}$H$_3$ et CH$_2$SO)—1H at 3.70 ppm (D, J=17 Hz, CH$_2$SO)—3H at 2.40 ppm (S, CH$_3$Ar)—3H at 2.34 ppm (S, CH$_3$Ar)—6H at 1.45 ppm (2S, (CH$_3$)$_2$C).

NMR no. 133-(b): 1H at 12.5 ppm (Se., ArNH CO)—1H at 8.78 ppm (D, J=9 Hz, CONH)—3H at 8.30 ppm (Se.,

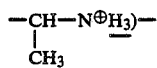

1H at 8.20 ppm (S, H thiazol in 3)—1H at 7.00 ppm (S, H thiazol)—1H at 6.00 ppm (D of D, J$_1$=9 Hz, J$_2$=4 Hz, H$_7$)—1H at 5.42 ppm (2D, J=13 Hz, CH$_2$OCO)—1H at 5.00 ppm (D, J=4 Hz, H$_6$)—1H at 4.90 ppm (D, J=13 Hz, CH$_2$OCO)—1H at 4.15 ppm (M,

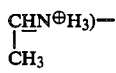

1H at 4.00 ppm (D, J=17 Hz, CH$_2$SO)—1H at 3.76 ppm (D, J=17 Hz, CH$_2$SO)—6H at 1.44 ppm (2S, (CH$_3$)$_2$C)—3H at 1.40 ppm (D, J=7 Hz, CH$_3$CH).

NMR no. 134-(b): 1H at 8.85 ppm (D, J=9 Hz, CONH)—1H at 8.50 ppm (S, H thiazol in 3)—3H at 7.90 ppm (Se., CH$_2$N$^{\oplus}$H$_3$)—1H at 7.00 ppm (S, H thiazol)—1H at 6.00 ppm (D of D, J$_1$=9 Hz, J$_2$=4 Hz, H$_7$)—1H at 5.42 ppm (D, J=13 Hz, CH$_2$OCO)—1H at 4.99 ppm (D, J=4 Hz, H$_6$)—1H at 4.84 ppm (D, J=13 Hz, CH$_2$OCO)—1H at 4.00 ppm (D, J=17 Hz, CH$_2$SO)—1H at 3.75 ppm (D, J=17 Hz, CH$_2$SO)—4H at 3.20 ppm (M, CH$_2$CH$_2$N$^{\oplus}$H$_3$)—6H at 1.45 ppm (2S, (CH$_3$)$_2$C).

NMR no. 135-(b): 1H at 8.80 ppm (D, J=9 Hz, CONH)—1H at 8.57 ppm (S, H thiazol in 3)—3H at 8.50 ppm (Se., CH$_2$N$^{\oplus}$H$_3$)—1H at 7.00 ppm (S, H thiazol)—1H at 6.00 ppm (D of D, J$_1$=9 Hz, J$_2$=4 Hz, H$_7$)—1H at 5.40 ppm (D, J=13 Hz, CH$_2$OCO)—1H at 5.00 ppm (D, J=4 Hz, H$_6$)—1H at 4.90 ppm (D, J=13 Hz, CH$_2$OCO)—2H at 4.45 ppm (M, CH$_2$N$^{\oplus}$H$_3$)—1H at 4.00 ppm (D, J=17 Hz, CH$_2$SO)—1H at 3.72 ppm (D, J=17 Hz, CH$_2$SO)—6H at 1.45 ppm (2S, (CH$_3$)$_2$C).

NMR no. 136-(b): 1H at 8.90 ppm (D, J=9 Hz, CONH)—1H at 8.60 ppm (S, H thiazol in 3)—3H at 8.50 ppm (Se., CH$_2$N$^{\oplus}$H$_3$)—1H at 6.98 ppm (S, H thiazol)—1H at 6.00 ppm (D of D, J$_1$=9 Hz, J$_2$=4 Hz, H$_7$)—1H at 5.42 ppm (D, J=13 Hz, CH$_2$OCO)—1H at 5.00 ppm (D, J=4 Hz, H$_6$)—1H at 4.84 ppm (D, J=13 Hz, CH$_2$OCO)—2H at 4.45 ppm (M, CH$_2$N$^{\oplus}$H$_3$)—1H at 4.00 ppm (D, J=17 Hz, CH$_2$SO)—1H at 3.72 ppm (D, J=17 Hz, CH$_2$SO)—4H at 2.40 ppm (M,

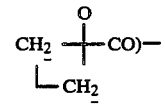

2H at 1.86 ppm (M,

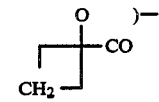

NMR no. 137-(b): 1H at 8.90 ppm (T, J=8 Hz,

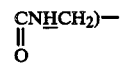

1H at 8.75 ppm (D, J=9 Hz, CONH)—3H at 8.00 ppm (Se., CH$_2$N$^{\oplus}$H$_3$)—2H at 7.88 ppm (D, J=8 Hz, HAr 2', 6')—2H at 7.40 ppm (D, J=8 Hz, HAr 3', 5')—1H at 6.96 ppm (S, H thiazol)—1H at 6.00 ppm (D of D, J$_1$=9 Hz, J$_2$=4 Hz, H$_7$)—1H at 5.44 ppm (D, J=13 Hz, CH$_2$OCO)—1H at 4.98 ppm (D, J=4 Hz, H$_6$)—1H at 4.80 ppm (D, J=13 Hz, CH$_2$OCO)—2H at 4.40 ppm (D, J=8 Hz, ArCH$_2$NH)—1H at 4.06 ppm 1H at 3.70 ppm (D, J=17 Hz, CH$_2$S→O)—2H at 3.57 ppm (M, OCCH$_2$N$^{\oplus}$H$_3$)—2H at 1.47 ppm (2S, (CH$_3$)$_2$C).

By operating as in Example 2 of Example 3, the compounds according to the invention are obtained, in the form of trifluoroacetates described in Table II below.

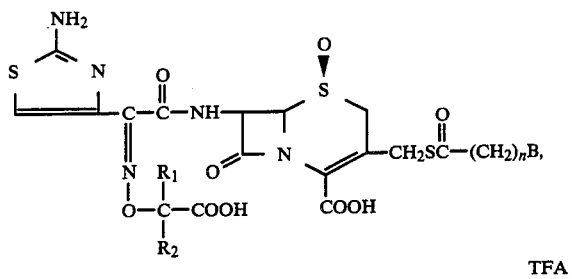

TFA

These compounds are identified by a reference number and for each of them are given the values of $R_1$, $R_2$, n and B and the NMR spectrum.

The chromatography eluant is also given which serves to isolate (V): the last intermediate product before deblocking of the acid and amine functions of the molecule. This intermediate V is characterized by its infra-red spectrum, the wavelengths indicated in cm$^{-1}$ correspond in order to the elongation vibration frequencies of the carbonyl at the 8 position of the beta lactam, the tertiobutylic esters and the thioester at the 3 position, the amide at the 7 position and the protective carbonate of the amine. When 2 wavelengths only are indicated the second corresponds to a wide band which covers the elongation vibration frequencies both of the esters, the amide and the protective carbonate of the amine and the thioester.

It happens for certain products that the vibration frequency of the thioester is at the same wavelength as that of the tertiobutylic esters. This is indicated in the table by +COS opposite the corresponding vibration frequency.

TABLE II

| SR no. | n | $-C\begin{smallmatrix}R_1\\R_2\end{smallmatrix}$ | B | Chromatography eluant from intermediate V vol/vol | | IR $\delta CO$ cm$^{-1}$ intermediate V | NMR no. |
|---|---|---|---|---|---|---|---|
| 41970 | 0 | $\begin{smallmatrix}CH_3\\CH_3\end{smallmatrix}$ (gem-dimethyl) | —(CH$_2$)$_3$NH$_2$ | CH$_2$Cl$_2$<br>AcOEt | 90<br>10 | 1800<br>1720<br>1690 | 1 |
| 41971 | " | " | —(CH$_2$)$_4$NH$_2$ | CH$_2$Cl$_2$<br>AcOEt | 90<br>10 | 1800<br>1715<br>1690 | 2 |
| 41972 | " | " | —(CH$_2$)$_5$NH$_2$ | CH$_2$Cl$_2$<br>AcOEt | 92<br>8 | 1800<br>1720<br>1690 | 3 |
| 41973 | " | " | piperidine-NH | CH$_2$Cl$_2$<br>AcOEt | 90<br>10 | 1800<br>1725<br>1690 | 4 |
| 42074 | " | " | piperidine-NH (R) | CH$_2$Cl$_2$<br>AcOEt | 90<br>10 | 1800<br>1725<br>1690 | 5 |
| 42076 | " | " | —(CH$_2$)$_3$NHCH$_3$ | CH$_2$Cl$_2$<br>AcOEt | 90<br>10 | 1800<br>1725<br>1690 | 6 |
| 42077 | " | " | —(CH$_2$)$_7$NH$_2$ | CH$_2$Cl$_2$<br>AcOEt | 95<br>5 | 1800<br>1720<br>1690 | 7 |
| 42118 | " | " | cyclohexyl-CH$_2$NH$_2$ | CH$_2$Cl$_2$<br>AcOEt | 95<br>5 | 1803<br>1720<br>1690 | 8 |
| 42119 | " | " | phenyl-CH$_2$NH$_2$ | CH$_2$Cl$_2$<br>AcOEt | 92.5<br>7.5 | 1805<br>1720 | 9 |
| 42187 | " | " | H$_2$N-cyclohexyl | CH$_2$Cl$_2$<br>AcOEt | 95<br>5 | 1805<br>1725 | 10 |
| 42199 | " | —CH$_2$— | piperidine-NH | CH$_2$Cl$_2$<br>AcOEt | 90<br>10 | 1800<br>1725<br>1690 | 11 |

TABLE II-continued

| SR no. | n | $-C\begin{smallmatrix}R_1\\R_2\end{smallmatrix}$ | B | Chromatography eluant from intermediate V vol/vol | | IR $\delta CO$ cm$^{-1}$ intermediate V | NMR no. |
|---|---|---|---|---|---|---|---|
| 42218 | " | —CH(CH₃)— | " | CH₂Cl₂ AcOEt | 92.5 7.5 | 1805 1725 1690 | 12 |
| 42219 | " | cyclobutylidene | piperidin-4-yl (NH) | CH₂Cl₂ AcOEt | 92.5 7.5 | 1805 1725 1690 | 13 |
| 42220 | " | —CH₂— | C₆H₄—CH₂NH₂ | CH₂Cl₂ AcOEt | 95 5 | 1800 1720 | 14 |
| 42221 | " | —CH(CH₃)— | " | CH₂Cl₂ AcOEt | 95 5 | 1800 1720 | 15 |
| 42222 | " | cyclobutylidene | " | CH₂Cl₂ AcOEt | 95 5 | 1805 1720 | 16 |
| 42531 | " | —C(CH₃)₂— | C₆H₄—CH₂NH₂ | CH₂Cl₂ MeOH | 100 0.5 | 1800 1720 | 17 |
| 42532 | " | cyclopropylidene | C₆H₄—CH₂NH₂ | CH₂Cl₂ MeOH | 100 0.5 | 1800 1720 | 18 |
| 42533 | " | —C(CH₃)₂— | C₆H₄—CH₂NHCH₃ | CH₂Cl₂ MeOH | 100 0.5 | 1800 1720 1690 | 19 |
| 42534 | " | cyclopropylidene | C₆H₄—CH₂NHCH₃ | CH₂Cl₂ MeOH | 100 0.5 | 1800 1720 1690 | 20 |
| 42535 | " | —C(CH₃)₂— | CH₃-C₆H₃-CH₂NH₂ | CH₂Cl₂ AcOEt | 95 5 | 1800 1720 | 21 |
| 42536 | " | cyclopropylidene | CH₃-C₆H₃-CH₂NH₂ | CH₂Cl₂ AcOEt | 95 5 | 1800 1720 | 22 |
| 42659 | " | —C(CH₃)₂— | CH₃-C₆H₃-CH₃NH₂ | CH₂Cl₂ MeOH | 100 0.4 | 1802 1720 | 23 |

TABLE II-continued

| SR no. | n | -C(R₁)(R₂) B | Chromatography eluant from intermediate V vol/vol | | IR δCO cm⁻¹ intermediate V | NMR no. |
|---|---|---|---|---|---|---|
| 42660 | " | H, CH₃ / C ; phenyl with -CH₃ and -CH₂NH₂ | CH₂Cl₂ MeOH | 100 0.5 | 1802 1720 | 24 |
| 42661 | " | CH₃-C-CH₃ ; phenyl with -CH₂NH₂ and -CH₃ | CH₂Cl₂ AcOEt | 95 5 | 1802 1720 | 25 |
| 42662 | " | H, CH₃-C- ; phenyl with -CH₂NH₂ and -CH₃ | CH₂Cl₂ AcOEt | 95 5 | 1802 1720 | 26 |
| 42663 | " | CH₃-C-CH₃ ; -C(CH₃)(CH₃)-CH₂NH₂ | CH₂Cl₂ MeOH | 100 0.4 | 1802 1720 1680 | 27 |
| 42664 | " | " ; phenyl—NHCOCH₂NH₂ | CH₂Cl₂ AcOEt | 95 5 | 1802 1720 | 28 |
| 42665 | " | cyclobutyl ; phenyl—NHCOCH₂NH₂ | CH₂Cl₂ AcOEt | 95 5 | 1802 1720 | 29 |
| 42672 | 1 | CH₃-C-CH₃ -CH₂- piperidine-NH | CH₂Cl₂ AcOEt | 90 10 | 1802 CH₂Cl₂ 1720 1680 | 30 |
| 42673 | 0 | " ; piperidine-N—C(=O)—CH₂NH₂ | CH₂Cl₂ MeOH | 101 1 | 1802 CH₂Cl₂ 1715 1690 | 31 |
| 42674 | " | cyclobutyl ; piperidine-N—C(=O)—CH₂NH₂ | CH₂Cl₂ MeOH | 100 1 | 1802 CH₂Cl₂ 1715 1690 | 32 |
| 42685 | " | CH₃-C-CH₃ ; phenyl—NHCOCH₂NH₂ | CH₂Cl₂ AcOEt | 95 5 | 1805 1725 1695 | 33 |
| 42686 | " | cyclobutyl ; phenyl—NHCOCH₂NH₂ | CH₂Cl₂ AcOEt | 95 5 | 1805 1725 1695 | 34 |

TABLE II-continued

| SR no. | n | -C(R₁)(R₂) | B | Chromatography eluant from intermediate V vol/vol | | IR δCO cm⁻¹ intermediate V | NMR no. |
|---|---|---|---|---|---|---|---|
| 42847 | " | -C(CH₃)₂- (isopropyl) | piperidine-N—C(O)(CH₂)₂NH₂ | CH₂Cl₂ MeOH | 100 1 | 1800 CH₂Cl₂ 1710 | 35 |
| 42850 | " | " | 3-CH₃-C₆H₃-CH₂NH₂ | CH₂Cl₂ MeOH | 100 0.7 | 1805 1720 | 36 |
| 42851 | " | cyclobutyl | 3-CH₃-C₆H₃-CH₂NH₂ | CH₂Cl₂ MeOH | 100 0.7 | 1805 1720 | 37 |
| 42853 | " | -C(CH₃)₂- | C₆H₄-CH(CH₃)-CH₂NH₂ | CH₂Cl₂ AcOEt | 95 5 | 1802 1720 | 38 |
| 42854 | " | cyclobutyl | C₆H₄-CH(CH₃)-CH₂NH₂ | CH₂Cl₂ MeOH | 100 0.4 | 1802 1720 | 39 |
| 42856 | " | -C(CH₃)₂- | thiazol-2-yl-NHCOCH₂CH₂NH₂ | CH₂Cl₂ AcOEt | 85 15 | 1803 1720 1685 | 40 |
| 42858 | " | " | thiazol-2-yl-NHCOCH₂NH₂ | CH₂Cl₂ MeOH | 100 1 | 1802 1725 1690 | 41 |
| 42859 | " | " | C₆H₄-NHCOCH₂CH₂NH₂ | CH₂Cl₂ AcOEt | 70 30 | 1802 1720 1690 | 42 |
| 42860 | " | cyclobutyl | C₆H₄-NHCOCH₂CH₂NH₂ | CH₂Cl₂ AcOEt | 70 30 | 1802 1720 | 43 |
| 42863 | " | -C(CH₃)₂- | C₆H₄-NHCOCH₂NHCH₃ | CH₂Cl₂ AcOEt | 90 10 | 1800 1720 1690 | 44 |
| 42868 | " | " | thiazol-2-yl-CH₂NH₂ | CH₂Cl₂ MeOH | 100 0.7 | 1802 1720 | 45 |

TABLE II-continued

| SR no. | n | $R_1$ $R_2$ B | Chromatography eluant from intermediate V vol/vol | IR $\delta CO$ cm$^{-1}$ intermediate V | NMR no. |
|---|---|---|---|---|---|
| 42902 | " | " 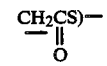—CH$_2$NHCOCH$_2$NH$_2$ | CH$_2$Cl$_2$ 100 MeOH 1 | 1802 1720 1670 | 46 |

NMR Spectra: The spectra are recorded at 60 MHz, indicated by (a) or at 250 MHz, indicated by (b); when two stereoisomers exist in the molecule, the split signals are indicated by *.

NMR no. 1-(a): 8H between 6 and 9 ppm (wide signal, CH$_2$, TFA, CO$_2$H)—1H at 8.40 ppm (D, J=9 Hz, CONH)—1H at 6.86 ppm (S, H thiazol)—1H at 6.00 ppm (D of D, J$_1$=9 Hz, J$_2$=4 Hz, H$_7$)—1H at 4.97 ppm (D, J=4 Hz, H$_6$)—1H at 4.20 ppm (AB, J$_{AB}$=13 Hz, CH$_2$SCO)—3H at 3.70 ppm (M, CH$_2$SCO and CH$_2$SO)—4H at 2.75 ppm (M, CH$_2$NH$_2$ and CH$_2$COS-)—2H at 1.77 ppm (M, CH$_2$CH$_2$CH$_2$)—6H at 1.45 ppm (S, (CH$_3$)$_2$C).

NMR no. 2-(a): 8H between 6.5 and 9 ppm (wide signal, CO$_2$H, TFA, NH$_2$)—1H at 8.40 ppm (D, J=9 Hz, CONH)—1H at 6.88 ppm (S, H thiazol)—1H at 6.0 ppm (D D, J$_1$=9 Hz, J$_2$=4 Hz, H$_7$)—1H at 5.0 ppm (D, J=4 Hz, H$_6$)—1H at 4.20 ppm (A of AB, J=13 Hz, CH$_2$SCO)—3H at 3.80 ppm (M, CH$_2$SO and CH$_2$SCO)—4H at 2.65 ppm (M, CH$_2$NH$_2$ and CH$_2$COS)—10H 1.45 ppm (S.e., (CH$_3$)$_2$C and CH$_2$(CH$_2$)$_2$CH$_2$).

NMR no. 3-(a): 8H between 6.5 et 8.7 ppm (wide signal (NH$_2$, CO$_2$H, TFA)—1H at 8.40 ppm (D, J=9 Hz, CONH)—1H at 6.87 ppm (S, H thiazol)—1H at 6.0 ppm (D of D, J$_1$=9 Hz, J$_2$=4 Hz, H$_7$)—1H at 5.0 ppm (D, J$_1$=4 Hz, H$_6$)—1H at 4.20 ppm (A of AB, J=13 Hz, CH$_2$SO)—3H at 3.70 ppm (M, CH$_2$SCO and CH$_2$SO)—4H at 2.80 ppm (M, CH$_2$NH$_2$ and CH$_2$CO) 12H at 1.45 ppm (S.e., (CH$_3$)$_2$C and CH$_2$(CH$_2$)$_3$CH$_2$).

NMR no. 4-(a): 7H between 6.5 et 9.5 ppm (Wide signal, NH$_2$, NH, CO$_2$H, TFA)—1H at 8.40 ppm (D, J=9 Hz, CONH)—1H at 6.90 ppm (S, H thiazol)—1H at 6.0 ppm (D of D, J$_1$=9 Hz, J$_2$=4 Hz, H$_7$)—1H at 5.0 ppm (D, J=4 Hz, H$_6$)—1H at 4.20 ppm (A of AB, J$_{AB}$=13 Hz, CH$_2$SCO)—3H at 3.70 ppm (M, CH$_2$SCO and CH$_2$SO)—5H at 3.0 ppm (M, CH$_2$N and CHCOS-)—4H at 1.90 ppm (M, CH$_2$CH$_2$N)—6H at 1.45 ppm (S, (CH$_3$)$_2$C).

NMR no. 5-(b): 5H between 7 and 9 ppm (wide signal, NH$_2$, TFA, NH)—1H at 8.34 ppm (2D, J=9 Hz, CONH)*—1H at 6.8 ppm (S, H thiazol)—1H at 5.97 ppm (D of D, J$_1$=9 Hz, J$_2$=4 Hz, H$_7$)—1H at 4.95 ppm (D, J=4 Hz, H$_6$)—1H at 4.16 ppm (2D, J=13 Hz, CH$_2$SCO)*—1H at 3.76 ppm (D, J=13 Hz, CH$_2$SCO)—2H at 3.66 ppm (S, CH$_2$SO)—1H at 3.4 ppm, 1H at 3.16 ppm and 2H at 2.95 ppm (M, CH$_2$N)—1H at 2.80 ppm (M, CHCOS)—4H between 1.5 and 2.1 ppm (M, CH$_2$CH$_2$CH$_2$N)—6H at 1.44 ppm (S, (CH$_3$)$_2$C).

NMR no. 6-(a): 3H at 8.50 ppm (S.e., CONH, N$^+$H$_2$)—3H at 7.80 ppm (S.e., N$^+$H$_3$)—1H at 6.85 ppm (S, H thiazol)—1H at 6.00 ppm (D of D, J$_1$=9 Hz, J$_2$=4 Hz, H$_7$)—1H at 5.00 ppm (D, J=4 Hz, H$_6$)—1H at 4.15 ppm (A of AB, J$_{AB}$=13 Hz, CH$_2$SCO)—1H at 3.80 ppm B of AB, J$_{AB}$=13 Hz, CH$_2$SCO)—2H at 3.70 ppm (S.e., CH$_2$SO)—7H at 2.50 ppm (M, CH$_3$NH, CH$_2$NH, $$\underset{\underset{O}{\parallel}}{CH_2CS}-$$

2H at 1.80 ppm (M, CH$_2$CH$_2$CH$_2$NH)—6H at 1.45 ppm (2S, (CH$_3$)$_2$C).

NMR no. 7-(a): 1H at 8.35 ppm (D, J=9 Hz, CONH)—8H between 6.5 and 10 ppm (CO$_2$H, NH$_2$, TFA-)—1H at 6.82 ppm (S, H thiazol)—1H at 6,00 ppm (D of D, J$_1$=9 Hz, J$_2$=4 Hz, H$_7$)—1H at 5.00 ppm (D, J=4 Hz, H$_6$)—1H at 4.15 ppm (A of AB, J$_{AB}$=13 Hz, CH$_2$SCO)—3H at 3.66 ppm (M, CH$_2$SO and B of AB, CH$_2$SCO)—4H at 2.65 ppm (M, CH$_2$CO and CH$_2$NH$_2$)—6H at 1.42 ppm (S, (CH$_3$)$_2$C)—10H at 1.25 ppm (S.e., (CH$_2$)$_5$CH$_2$NH$_2$).

NMR no. 8-(b): 1H at 8.34 ppm (D, J=9 Hz, CONH)—3H at 7.80 ppm (S.e., N$^+$H$_3$)—3H at 7.40 ppm (S.e., N$^+$H$_3$)—1H at 6.78 ppm (S, H thiazol)—1H at 5.94 ppm (D of D, J$_1$=9 Hz, J$_2$=4 Hz, H$_7$)—1H at 4.94 ppm (D, J=4 Hz, H$_6$)—1H at 4.14 ppm (D, J=13 Hz, CH$_2$SCO)—1H at 3.69 ppm (D, J=13 Hz, CH$_2$SO)—2H at 3.63 ppm (S, CH$_2$SO)—2H at 2.60 ppm (M, CH$_2$NH$_2$)—1H at 2.45 ppm (M, CHCOS)—4H at 1.84 ppm (M, CH$_2$CHCOS)—6H at 1.44 ppm (2S, (CH$_3$)$_2$C)—2H at 1.40 ppm and 2H at 1.0 ppm (M, CH$_2$CHCH$_2$NH$_2$). NMR no. 9-(b): 1H at 8.36 ppm (D, J=9 Hz, NHCO)—3H at 8.30 ppm (S.e., N$^+$H$_3$)—2H at 7.94 ppm (D, J=8 Hz, H ortho CO)—2H at 7.55 ppm (D, J=8 Hz, H meta CO)—3H at 7.40 ppm (S.e. N$^+$H$_3$)—1H at 6.76 ppm (S, H thiazol)—1H at 5.95 ppm (D of D, J$_1$=9 Hz, J$_2$=4 Hz, H$_7$)—1H at 4.95 ppm (D, J=4 Hz, H$_6$)—1H at 4.40 ppm (D, J=13 Hz, CH$_2$SCO)—2H at 4.10 ppm (M, CH$_2$NH$_2$)—1H at 3.90 ppm (D, J=13 Hz, CH$_2$SCO)—2H at 3.74 ppm (S, CH$_2$SO)—6H at 1.42 ppm (2S, (CH$_3$)$_2$C).

NMR no. 10-(a): 1H at 8.30 ppm (D, J=9 Hz, CONH)—8H between 6.5 and 9 ppm (S.e., N$^+$H$_3$, CO$_2$H)—1H at 6.80 ppm (S, H thiazol)—1H at 5.95 ppm (M, H$_7$)—1H at 4.90 ppm (D, J=4 Hz H$_6$)—1H at 4.25 ppm (A of AB, J$_{AB}$=13 Hz, CH$_2$SCO)—1H at 3.90 ppm (B of AB, J$_{AB}$=13 Hz, CH$_2$SCO)—2H at 3.65 ppm (S.e., CH$_2$SO)—10H between 1 and 2.3 ppm (M,

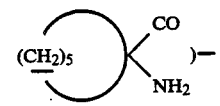

6H at 1.43 ppm (S, (CH$_3$)$_2$C).

NMR no. 11-(b): 1H at 8.79 ppm (D, J=9 Hz, CONH)—1H at 8.60 ppm and 1H at 8.40 ppm (S.e., N$^+$H$_2$)—3H at 7.30 ppm (S.e., N$^+$H$_3$)—1H at 6.84 ppm (S, H thiazol)—1H at 5.84 ppm (D of D, J₁=9 Hz, J₂=4 Hz, H7)—1H at 4.90 ppm (D, J=4 hz, H6)—2H at 4.55 ppm (S, CH₂ON)—1H at 4.15 ppm (D, J=13 Hz, CH₂SCO)—1H at 3.74 ppm (D, J=13 Hz, CH₂SCO)—2H at 3.54 ppm (S, CH₂SO)—2H at 3.20 ppm and 3H at 2.90 ppm (M, CH₂NH and CHCOS-)—2H at 1.95 ppm et 2H at 1.65 ppm (M, CH₂CH₂NH).

NMR no. 12-(b): 2H at 8.60 ppm (M, CONH, N⁺H₂)—1H at 8.40 ppm (S.e., N⁺H₂)—3H at 7.30 ppm (S.e., N⁺H₃)—1H at 6.81 ppm (2S, H thiazol)*—1H at 5.92 ppm (D of D, J₁=9 Hz, J₂=4 Hz, H7)—1H at 4.92 ppm (2D superposed, H6)*—1H at 4.60 ppm (Q, J=7 Hz, CHON)—1H at 4.16 ppm (D, J=13 Hz, CH₂SCO)—1H at 3.75 ppm (D, J=13 Hz, CH₂SCO) 2H at 3.65 ppm (S, CH₂SO)—2H at 3.25 ppm and 3H at 2.95 ppm (M, CHCOS and

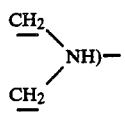

2H at 1.95 ppm et 2H at 1.70 ppm (M,

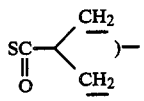

3H at 1.45 ppm (D, J=7 Hz, CH₃CH).

NMR no. 13-(b): 2H at 8.70 ppm (M, CONH and N⁺H₂)—1H at 8.40 ppm (M, N⁺H₂)—3H at 7.40 ppm (S.e., N⁺H₃)—1H at 6.79 ppm (S, H thiazol)—1H at 5.90 ppm (D of D, J₁=9 Hz, J₂=4 Hz, H7)—1H at 4.94 ppm (D, J=4 Hz, H6)—1H at 4.16 ppm (D, J=13 Hz, CH₂SCO)—1H at 3.74 ppm (D, J=13 Hz, CH₂SCO) 2H at 3.70 ppm (S, CH₂SO)—2H at 3.25 ppm (M, CH₂NH)—3H at 2.90 ppm (M, CH₂NH and CHCOS-)—4H at 2.40 ppm (M, 6H at 1.80 ppm (M,

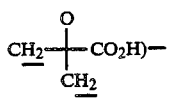

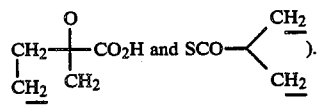

NMR no. 14-(b): 1H at 8.65 ppm (D, J=9 Hz, CONH)—3H at 8.20 ppm (S.e., N⁺H₃)—2H at 7.92 ppm (D, J=8 Hz, H ortho CO)—2H at 7.56 ppm (D, J=8 Hz, H meta CO)—3H at 7.30 ppm S.e., N⁺H₃)—1H at 6.82 ppm (S, H thiazol)—1H at 5.88 ppm (D of D, J₁=9 Hz, J₂=4 Hz, H7)—1H at 4.92 ppm (D, J=4 Hz, H6)—2H at 4.55 ppm (S, CH₂ON)—1H at 4.37 ppm (D, J=13 Hz, CH₂SCO)—2H at 4.13 ppm (M, CH₂NH₂)—1H at 4.42 ppm (D, J=13 Hz, CH₂SCO)—2H at 3.74 ppm (S, CH₂SO).

NMR no. 15-(b): 1H at 8.60 ppm (2D, J=9 Hz, CONH)*—3H at 8.20 ppm (S.e., N⁺H₃)—2H at 7.92 ppm (D, J=8 Hz, H ortho CO)—2H at 7.56 ppm (D, J=8 Hz, H meta CO)—3H at 7.30 ppm (S.e., N⁺H₃)—1H at 6.82 ppm (2S, H thiazol)*—1H 5.92 ppm (D of D, J₁=9 Hz, J₂=4 Hz, H7)—1H at 4.95 ppm (2D superposed, H6)*—1H at 4.60 ppm (Q, J=7 Hz, CHON)—1H at 4.40 ppm (D, J=13 Hz, CH₂SCO)—2H at 4.13 ppm (M, CH₂NH₂)—1H at 3.90 ppm (D, J=13 Hz, CH₂SCO)—2H at 3.75 ppm (S, CH₂SO)—3H at 1.45 ppm (D, J=7 Hz, CH₃CH).

NMR no. 16-(b): 1H at 8.61 ppm (D, J=9 Hz, CONH)—5H at 8.40 ppm (S.e., N⁺H₃, CO₂H)—2H at 7.95 ppm (D, J=8 Hz, H ortho CO)—2H at 7.61 ppm (D, j+8 Hz, H meta CO)—3H at 7.30 ppm (S.e., N⁺H₃)—1H at 6.76 ppm (S, H thiazol)—1H at 5.92 ppm (D of D, J₁=9 Hz, J₂=4 Hz, H7)—1H at 4.93 ppm (D, J=4 Hz, H6)—1H at 4.42 ppm (D, J=13 Hz, CH₂SCO)—2H at 4.10 ppm (S.e., CH₂NH₂)—1H at 3.92 ppm (D, J=13 Hz, CH₂SCO)—2H at 3.74 ppm (S, CH₂SO)—4H at 2.35 ppm (M,

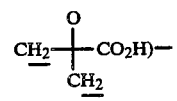

2H at 1.85 ppm (M,

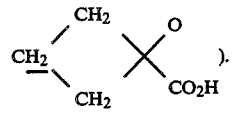

NMR no. 17-(b): 1H at 8.62 ppm (D, J=9 Hz, CONH)—3H at 8.20 ppm (S.e., CH₂N⊕H₃)—1H at 8.00 ppm (S.e., HAr 2')—1H at 7.90 ppm (D, J=8 Hz, HAr 6')—1H at 7.72 ppm (D, J=8 Hz, HAr 4')—1H at 7.55 ppm (T, J=8 Hz, HAr 5')—1H at 6.93 ppm (S, H thiazol)—1H at 5.95 ppm (D of D, J₁=9 Hz, J₂=4 Hz, H7)—1H at 4.93 ppm (D, J=4 Hz H6)—1H at 4.43 ppm (D, J=13 Hz, CH₂SCO)—2H at 4.10 ppm (Q, J=7 Hz, CH₂N⊕H₃)—1H at 3.94 ppm (D, J=13 Hz, CH₂SCO)—2H at 3.75 ppm (Se., CH₂SO)—6H at 1.45 ppm (2S, (CH₃)₂C).

NMR no. 18-(b): 1H at 8.80 ppm (D, J=9 Hz, CONH)—3H at 8.20 ppm (Se., CH₂N⊕H₃)—1H at 8.00 ppm (Se., HAr 2')—1H at 7,90 ppm (D, J=8 Hz, HAr 6')—1H at 7.72 ppm (D, J=8 Hz, HAr 4')—1H at 7.55 ppm (T, J=8 Hz, HAr 5')—1H at 6.92 ppm (S, H thiazol)—1H at 5.94 ppm (D of D, J₁=9 Hz, J₂=4 Hz, H7)—1H at 4.96 ppm (D, J=4 Hz, H6)—1H at 4.44 ppm (D, J=13 Hz, CH₂SCO)—2H at 4.10 ppm (Q, J=7 Hz, CH₂N⊕H₃)—1H at 3.94 ppm (D, J=13 Hz, CH₂SCO)—2H at 3.77 ppm (Se., CH₂SO)—4H at 2.40 ppm (M,

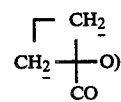

2H at 1.90 ppm (M,

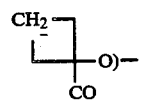

NMR no. 19-(b): 2H at 8.80 ppm (Se., N⊕H₂CH₃)—1H at 8.60 ppm (D, J=9 Hz, CONH)—2H at 7.95 ppm (D, J=8 Hz, HAr 2',6')—2H at 7.60 ppm (D, Ar 3', 5')—1H at 6.94 ppm (S, H thiazol)—1H at 5.95 ppm (D of D, J₁=9 Hz, J₂=4 Hz, H<u>7</u>)—1H at 4.95 ppm (D, J=4 Hz, H<u>6</u>)—1H at 4.42 ppm (D, J=13 Hz, CH<u>2</u>SCO)—2H at 4.16 ppm (T, J=7 Hz, CH<u>2</u>N⊕H₂CH₃)—1H at 3.92 ppm (D, J=13 Hz, CH<u>2</u>SCO)—2H at 3.75 ppm (Se., CH<u>2</u>SO)—3H at 2.55 ppm (T, J=7 Hz CH₂N⊕H₂CH<u>3</u>)—6H at 1.45 ppm (2S, (CH<u>3</u>)₂C).

NMR no. 20-(b): 1H at 8.84 ppm (D, J=9 Hz, CON<u>H</u>)—2H at 8.80 ppm (Se., N⊕<u>H₂</u>—CH₃)—2H at 7.95 ppm (D, J=8 Hz, <u>H</u>Ar, 2′, 6′)—2H at 7.60 ppm (D, J=8 Hz, <u>H</u>Ar 3′, 5′)—1H at 6.95 ppm (S, <u>H</u> thiazol)—1H at 5.94 ppm (D of D, J₁=9 Hz, J₂=4 Hz, H<u>7</u>)—1H at 4.95 ppm (D, J=4 Hz, H<u>6</u>)—1H at 4.45 ppm (D, J=13 Hz, CH<u>2</u>SCO)—2H at 4.16 ppm (T, J=7 Hz, CH<u>2</u>N⊕H₂CH₃)—1H at 3.92 ppm (D, J=13 Hz, CH<u>2</u>SCO)—2H at 3.75 ppm (Se., CH<u>2</u>SO)—3H at 2.55 ppm (T, J=7 Hz, CH₂N⊕H₂—CH<u>3</u>)—4H at 2.40 ppm (M,

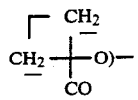

2H at 1.90 ppm (M,

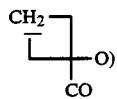

NMR no. 21-(b): 1H at 8.66 ppm (D, J=9 Hz, CON<u>H</u>)—3H at 8.10 ppm (Se., CH₂N⊕<u>H</u>₃)—2H at 7.55 ppm (M, <u>H</u>Ar 4′, 6′)—1H at 7.37 ppm (T, J=8 Hz, <u>H</u>Ar 5′)—1H at 6.95 ppm (S, <u>H</u> thiazol)—1H at 5.96 ppm (D of D, J₁=9 Hz, J₂=4 Hz, H<u>7</u>)—1H at 4.96 ppm (D, J=4 Hz, H<u>6</u>)—1H at 4.39 ppm (D, J=13 Hz, CH<u>2</u>SCO)—2H at 4.07 ppm (M, ArCH<u>2</u>N⊕H₃)—1H at 3.90 ppm (D, J=13 Hz, CH<u>2</u>SCO)—2H at 3.78 ppm (S, CH<u>2</u>SO)—3H at 2.26 ppm (S, CH<u>3</u>Ar)—6H at 1.45 ppm (2S, (CH<u>3</u>)₂C).

NMR no. 22-(b): 1H at 8.89 ppm (D, J=9 Hz, CON<u>H</u>)—3H at 8.10 ppm (Se., CH₂N⊕<u>H</u>₃)—2H at 7.55 ppm (M, <u>H</u>Ar 4′, 6′)—1H at 7.37 ppm (T, J=8 Hz, <u>H</u>Ar 5′)—1H at 6.95 ppm (S, <u>H</u> thiazol)—1H at 5.95 ppm (D of D, J₁=9 Hz, J₂=4 Hz, H<u>7</u>)—1H at 5.0 ppm (D, J=4 Hz, H<u>6</u>)—1H at 4.40 ppm (D, J=13 Hz, CH<u>2</u>SCO)—2H at 4.05 ppm (M, ArCH<u>2</u>N⊕H₃)—1H at 3.90 ppm (D, J=13 Hz, CH<u>2</u>SCO)—2H at 3.79 ppm (S, CH<u>2</u>SO)—4H at 2.40 ppm (M,

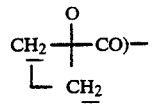

3H at 2.25 ppm (S, CH<u>3</u>Ar)—2H at 1.90 ppm (M,

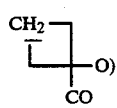

NMR no. 23-(b): 1H at 8.64 ppm (D, J=9 Hz, CON<u>H</u>)—3H at 8.14 ppm (Se., CH₂N⊕<u>H</u>₃)—1H at 7.95 ppm (S, <u>H</u>Ar 2′)—1H at 7.60 ppm (D, J=8 Hz, <u>H</u>Ar 6′)—1H at 7.39 ppm (D, J=8 Hz, <u>H</u>Ar 5′)—1H at 6.95 ppm (S, <u>H</u> thiazol)—1H at 5.95 ppm (D of D, J₁=9 Hz, H<u>7</u>)—1H at 4.96 ppm (D, J=4 Hz, H<u>6</u>)—1H at 4.37 ppm (D, J=13 Hz, CH<u>2</u>SCO)—2H at 4.08 ppm (M, CH<u>2</u>N⊕H₃)—1H at 3.94 ppm (D, J=13 Hz, CH<u>2</u>SCO)—2H at 3.74 ppm (Se., CH<u>2</u>SO)—3H at 2.37 ppm (S, ArCH<u>3</u>)—6H at 1.45 ppm (2S, (CH<u>3</u>)₂C).

NMR no. 24-(b): 1H at 8.80 ppm (2D, J=9 Hz CON<u>H</u>)—3H at 8.20 ppm (Se., CH₂N⊕<u>H</u>₃)—1H at 7.94 ppm (S, <u>H</u>Ar 2′)—1H at 7.80 ppm (D, J=8 Hz, <u>H</u>Ar 6′)—1H at 7.39 ppm (D, J=8 Hz, <u>H</u>Ar 5′)—1H at 6.95 ppm (2S, <u>H</u> thiazol)—1H at 5.94 ppm (D of D, J₁=9 Hz, J₂=4 Hz, H<u>7</u>)—1H at 4.95 ppm (2D, J=4 Hz, H<u>6</u>)—1H at 4.70 ppm (M, CH₃<u>CH</u>ON)—1H at 4.37 ppm (2D, J=13 Hz, CH<u>2</u>SCO)—2H at 4.08 ppm (M, CH<u>2</u>N⊕H₃)—1H at 3.94 ppm (D, J=13 Hz, CH<u>2</u>SCO)—2H at 3.73 ppm (Se., CH<u>2</u>SO)—3H at 2.36 ppm (S, ArCH<u>3</u>)—3H at 1.42 ppm (D, J=7 Hz, C<u>H₃</u>CHON).

NMR no. 25-(b): 1H at 8.66 ppm (D, J=9 Hz, CON<u>H</u>)—3H at 8.17 ppm (Se., CH₂N⊕<u>H</u>₃)—2H at 7.80 ppm (M, <u>H</u>Ar 2′, 6′)—1H at 7.50 ppm (D, J=8 Hz, <u>H</u>Ar 5′)—1H at 6.95 ppm (S, <u>H</u> thiazol)—1H 5.95 ppm (D of D, J₁=9 Hz, J₂=4 Hz, H<u>7</u>)—1H at 4.95 ppm (D, J=4 Hz, H<u>6</u>)—1H at 4.40 ppm (D, J=13 Hz, CH<u>2</u>SCO)—2H at 4.06 ppm (M, CH<u>2</u>N⊕H₃)—1H at 3.90 ppm (D, J=13 Hz, CH<u>2</u>SCO)—2H at 3.74 ppm (S, CH<u>2</u>SO)—3H at 2.46 ppm (S, ArCH<u>3</u>)—6H at 1.46 ppm (2S, (CH<u>3</u>)₂C).

NMR no. 26-(b): 1H at 8.80 ppm (2D, J=9 Hz, CON<u>H</u>)—3H at 8.20 ppm (Se., CH₂N⊕<u>H</u>₃)—2H at 7.80 ppm (M, <u>H</u>Ar 2′, 6′)—1H at 7.46 ppm (D, J=8 Hz, <u>H</u>Ar 5′)—1H at 6.95 ppm (2S, <u>H</u> thiazol)—1H at 5.94 ppm (D of D, J₁=9 Hz, J₂=4 Hz, H<u>7</u>)—1H at 4.95 ppm (2D, J=4 Hz, H<u>6</u>)—1H at 4.66 ppm (M, CH₃<u>CH</u>—ON)—1H at 4.40 ppm (2D, J=13 Hz, CH<u>2</u>SCO)—2H at 4.06 ppm (M, CH<u>2</u>N⊕H₃)—1H at 3.90 ppm (D, J=13 Hz, CH<u>2</u>SCO)—2H at 3.76 ppm (Se., CH<u>2</u>SO)—3H at 2.40 ppm (S, ArCH<u>3</u>)—3H at 1.44 pm (D, J=7 Hz, C<u>H₃</u>CHON).

NMR no. 27-(b): 1H at 8.66 ppm (D, J=9 Hz, CON<u>H</u>)—3H at 7.80 ppm (Se., CH₂N⊕<u>H</u>₃)—1H at 6.95 ppm (S, <u>H</u> thiazol)—1H at 5.98 ppm (D of D, J₁=9 Hz, J₂=4 Hz, <u>H</u><u>7</u>)—1H at 4.95 ppm (D, J=4 Hz, H<u>6</u>)—1H at 4.18 ppm (D, J=13 Hz, CH<u>2</u>SCO)—1H at 3.78 ppm (D, J=13 Hz, CH<u>2</u>SO)—2H at 3.69 ppm (Se., CH<u>2</u>SO)—2H at 2.95 ppm (M, CH<u>2</u>N⊕H₃)—6H at 1.45 ppm (2S, (CH₃)₂—C—O)—6H at 1.22 ppm (S, (CH<u>3</u>)₂CCOS).

NMR no. 28-(b): 1H at 10.80 ppm (S, ArN<u>H</u>CO)—1H at 8.66 ppm (D, J=9 Hz, CON<u>H</u>)—3H at 8.05 ppm (Se., CH₂N⊕<u>H</u>₃)—2H at 7.89 ppm (D, J=8 Hz <u>H</u>Ar 2′, 6′)—2H at 7.74 ppm (D, J=8 Hz <u>H</u>Ar 3′, 5′)—1H at 6.96 ppm (S, <u>H</u> thiazol)—1H at 5.95 ppm (D of D, J₁=9 Hz, J₂=4 Hz, H<u>7</u>)—1H at 4.95 ppm (D, J=4 Hz, H<u>6</u>)—1H at 4.42 ppm (D, J=13 Hz, CH<u>2</u>SCO)—1H at 3.88 ppm (D, J=13 Hz, CH<u>2</u>SCO)—4H at 3.80 ppm (M, CH<u>2</u>SO and CH<u>2</u>N⊕H₃)—6H at 1.45 ppm (2S, (C<u>H</u>₃)₂C).

NMR no. 29-(b): 1H at 10.83 ppm (S, ArN<u>H</u>CO)—1H at 8.89 ppm (D, J=9 Hz, CON<u>H</u>)—3H at 8.10 ppm (Se., CH₂N⊕<u>H</u>₃)—2H at 7.90 ppm (D, J=8 Hz, <u>H</u>Ar 2′, 6′)—2H at 7.71 ppm (D, J=8 Hz, <u>H</u>Ar 3′, 5′)—1H at 6.95 ppm (S, <u>H</u> thiazol)—1H at 5.94 ppm (D of D, J₁=9 Hz, J₂=4 Hz, H<u>7</u>)—1H at 4.95 ppm (D, J=4 Hz, H<u>6</u>)—1H at 4.45 ppm (D, J=13 Hz, CH<u>2</u>SCO)—1H at 3.87 ppm (D, J=13 Hz, CH<u>2</u>SCO)—4H at 3.80 ppm (M, CH<u>2</u>SO and CH<u>2</u>N⊕H₃)—4H at 2.40 ppm (M,

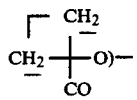

2H at 1.90 ppm (M,

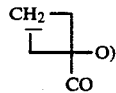

NMR no. 30(b): 1H at 8.50 ppm (Se., N⊕H$_2$ piperidine)—1H at 8.20 ppm (Se., N⊕H$_2$ piperidine)—1H at 8.36 ppm (D, J=9 Hz, CONH)—1H at 6.76 ppm (S, H thiazol)—1H at 5.95 ppm (D of D, J$_1$=9 Hz, J$_2$=4 Hz, H$_7$)—1H at 4.92 ppm (D, J=4 Hz, H$_6$)—1H at 4.16 ppm (D, J=13 Hz, CH$_2$SCO)—1H at 3.72 ppm (D, J=13 Hz, CH$_2$SCO)—2H at 3.14 ppm (S, CH$_2$SO)—2H at 3.17 ppm 2H at 2.80 ppm (M, 6H $_2$ in α N⊕H$_2$)—2H at 2.55 ppm (D, J=7 Hz CH$_2$COS)—1H at 2.00 ppm (M, CHCH$_2$COS)—2H at 1.75 ppm and 2H 1.30 ppm (M, CH$_2$ in β N⊕H$_2$)—6H at 1.45 ppm (2S, (CH$_3$)$_2$C).

NMR no. 31-(b): 1H at 8.34 ppm (D, J=9 Hz, CONH)—3H at 7.92 ppm (Se., CH$_2$N⊕H$_3$)—3H at 7.30 ppm (Se., N⊕H$_3$ thiazol)—1H at 6.76 ppm (S, H thiazol)—1H at 5.95 ppm (D of D, J$_1$=9 Hz, J$_2$=4 Hz, H$_7$)—1H at 4.92 ppm (D, J=4 Hz, H$_6$)—1H at 4.26 ppm (DE, J=12 Hz, H$_2$Eq piperidine)—1H at 4.15 ppm (D, J=13 Hz, CH$_2$SCO)—2H at 3.84 ppm (M, CH$_2$N⊕H$_3$)—1H at 3.72 ppm (D, J=13 Hz, CH$_2$SCO)—3H at 3.60 ppm (M, CH$_2$SO+H$_6$ Eq piperidine)—1H at 3.05 ppm (TE, J=12 Hz, H$_2$ Ax piperidine)—1H at 2.87 ppm (TE, CHCOS)—H at 2.74 ppm (TE, J=12 Hz, H$_6$ Ax piperidine)—2H at 1.86 ppm (M, H en 3 in 5 piperidine)—2H at 1.45 ppm (M, H en 3 and 5 piperidine)—6H at 1.45 ppm (2S, (CH$_3$)$_2$C).

NMR no. 32-(b): 1H at 8.66 ppm (D, J=9 Hz, CONH)—3H at 7.90 ppm (Se., CH$_2$N⊕H$_3$)—3H at 7.30 ppm (Se., —N⊕H$_3$ thiazol)—1H at 6.78 ppm (S, H thiazol)—1H at 5.90 ppm (D of D, J$_1$=9 Hz, J$_2$=4 Hz, H$_7$)—1H at 4.94 ppm (D, J=4 Hz, H$_6$)—1H at 4.26 ppm (De., J=12 Hz, H$_2$ Eq piperidine)—1H at 4.16 (D, J=13 Hz, CH$_2$SCO)—2 H at 3.82 ppm (M, CH$_2$ Gly)—1H at 3.74 ppm (D, J=13 Hz, CH$_2$SO)—3H at 3.63 ppm (Se., CH$_2$SOH$_6$ Eq piperidine)—1H at 3.05 ppm (Te., J=13 Hz, H$_2$ Ax piperidine)—1H at 2.87 ppm (Te., J=12 Hz,

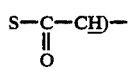

1H at 2.75 ppm (Te., J=12 Hz, H$_6$ Ax piperidine)—4H at 2.44 ppm (M,

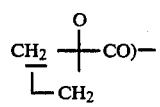

4H at 1.90 ppm (M,

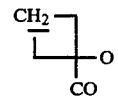

and H$_3$ Eq and H$_5$ Eq piperidine)—2H at 1.50 ppm (M, H$_3$ Ax and H$_5$ Ax piperidine).

NMR no. 33-(b): 1H at 10.70 ppm (S, ArNHCO)—1H at 8.70 ppm (D, J=9 Hz, CONH)—1H at 8.30 ppm (S, HAr 2')—3H at 8.10 ppm (Se., CH$_2$N⊕H$_3$)—1H at 7.75 ppm (D, J=8 Hz, HAr 6')—1H at 7.60 ppm (D, J=8 Hz, HAr 4')—1H at 7.50 ppm (T, J=8 Hz, HAr 5')—1H at 6.95 ppm (S, H thiazol)—1H at 5.95 ppm (D of D, J$_1$=9 Hz, J$_2$=4 H, H$_7$)—1H at 4.95 ppm (D, J=4 Hz, H$_6$)—1H at 4.45 ppm (D, J=13 Hz, CH$_2$SCO)—1 H at 3.90 ppm (D, J=13 Hz, CH$_2$SCO)—4H at 3.75 ppm (M, CH$_2$SO and CH$_2$ Gly)—6H at 1.45 ppm (2S, (CH$_3$)$_2$C).

NMR no. 34-(b): 1H at 10.65 ppm (Se., ArNH CO)—1H at 8.80 ppm (D, J=9 Hz, NHCO)—1H at 8.25 ppm (Se., HAr 2')—3H at 8.05 ppm (Se., CH$_2$N⊕H$_3$)—1H at 7.75 ppm (D, J=8 Hz, HAr 6')—1H at 7.58 ppm (D, J=8 Hz, HAr 4')—1H at 7.50 ppm (T, J=8 Hz, HAr 5')—1H at 6.95 ppm (S, H thiazol)—1H at 5.95 ppm (D of D, J$_1$=9 Hz, J$_2$=4 Hz, H$_7$)—1H at 4.95 ppm (D, J=4 Hz, H$_6$)—1H at 4.45 ppm (D, J=13 Hz, CH$_2$SCO)—1H at 3.90 ppm (D, J=13 Hz, CH$_2$SCO)—4H at 3.75 ppm (M, CH$_2$SO and CH$_2$ Gly)—4H at 2.40 ppm (M,

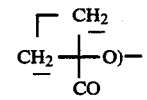

2H at 1.90 ppm (M,

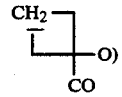

NMR no. 35-(b): 1H at 8.40 ppm (D, J=9 Hz, CONH)—6H at 7.60 ppm (Se., N⊕H$_3$)—1H at 6.80 ppm (S, H thiazol)—1H at 5.95 ppm (D de D, J$_1$=9 Hz, J$_2$=4 Hz, H$_7$)—1H at 4.95 ppm (D, J=4 Hz, H$_6$)—1H at 4.30 ppm (M, H$_{2e}$ piperidine)—1H at 4.16 ppm (D, J=13 Hz, CH$_2$SCO)—1H at 3.75 ppm (D, J=13 Hz, CH$_2$SCO)—2H at 3.60 ppm (S, CH$_2$SO)—1H at 3.55 ppm (M, H$_{6e}$ piperidine)—4H at 2.90 ppm (M, CH$_2$N⊕H$_3$ et H$_{2a}$ and H$_{6a}$ piperidine)—3H at 2.60 ppm (M, CH$_2$CH$_2$N⊕H$_3$H$_4$ piperidine)—2H at 1.80 ppm et 2H at 1.50 ppm (2M, H$_3$ at H$_5$ piperidine)—6H at 1.45 ppm (2S, (CH$_3$)$_2$C).

NMR no. 36-(b): 1H at 8.70 ppm (D, J=9 Hz, CONH)—3H at 8.20 ppm (Se., CH$_2$N⊕H$_3$)—1H at 7.75 ppm (D, J=8 Hz, HAr 6')—2H at 7.43 ppm (M, HAr 3', 5')—1H at 6.98 ppm (Se., H thiazol)—1H at 6.00 ppm (D of D, J$_1$=9 Hz, J$_2$=4 Hz, H$_7$)—1H at 4.97 ppm (D, J=4 Hz, H$_6$)—1H at 4.34 ppm (D, J=13 Hz, CH$_2$SCO)—2H at 4.00 ppm (M, CH$_2$N⊕H$_3$)—1H at 3.90 ppm (D, J=13 Hz, CH$_2$SCO) 2H at 3.77 ppm (Se., CH$_2$SO—1H at 2.34 ppm (S, CH$_3$Ar)—6H at 1.46 ppm (2S, (CH$_3$)$_2$C).

NMR no. 37-(b): 1H at 8.80 ppm (D, J=9 Hz, CONH)—3H at 8.15 ppm (Se., CH$_2$N⊕H$_3$)—1H at 7.72 ppm (D, J=8 Hz, HAr 6')—2H at 7.40 ppm (M, HAr 3', 5')—1H at 6.95 ppm (S, H thiazol)—1H at 5.95 ppm (D of D, J$_1$=9 Hz, J$_2$=4 Hz, H$_7$)—1H at 4.93 ppm (D, J=4 Hz, H$_6$)—1H at 4.34 ppm (D, J=13 Hz, CH$_2$SCO)—2H at 4.00 ppm (M, CH$_2$N$^\oplus$H$_3$)—1H at 3.90 ppm (D, J=13 Hz, CH$_2$SCO)—2H at 3.78 ppm (Se., CH$_2$SO)—2H at 2.34 ppm (S, CH$_3$ Ar)—4H at 2.30 ppm (M,

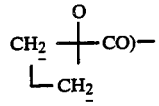

2H at 1.80 ppm (M,

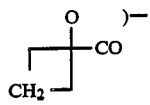

NMR no. 38-(b): 1H at 8.60 ppm (D, J=9 Hz, CONH)—7H at 7.70 ppm (M, HAr et CH$_2$N$^\oplus$H$_3$)—1H at 6.98 ppm (S, H thiazol)—1H at 5.98 ppm (D of D, J$_1$=9 Hz, J$_2$=4 Hz, H$_7$)—1H at 4.96 ppm (D, J=4 Hz, H$_6$)—1H at 4.38 ppm (D, J=13 Hz, CH$_2$SCO) 1H at 3.94 ppm (D, J=13 Hz, CH$_2$SCO)—2H at 3.75 ppm (Se., CH$_2$SO)—3H at 3.00 ppm (M, CHCH$_2$N$^\oplus$H$_3$)—6H at 1.47 ppm (2S, (CH$_3$)$_2$C)—3H at 1.19 ppm (D, J=7 Hz, CH$_3$CH).

NMR no. 39-(b): 1H at 8.80 ppm (D, J=9 Hz, CONH)—7H at 7.80 ppm (M, HAr et N$^\oplus$H$_3$CH$_2$)—1H at 6.95 ppm (S, H thiazol)—1H at 5.95 ppm (D de D, J$_1$=9 Hz, J$_2$=4 Hz, H$_7$)—1H at 4.97 ppm (D, J=4 Hz, H$_6$)—1H at 4.40 ppm (D, J=13 Hz, CH$_2$SCO)—1H at 3.93 ppm (D, J=13 Hz CH$_2$SCO)—2H at 3.75 ppm (Se., CH$_2$SO)—3H at 3.00 ppm (M, CHCH$_2$N$^\oplus$H$_3$)—4H at 2.40 ppm (M,

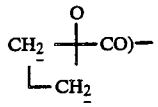

2H at 1.85 ppm (M,

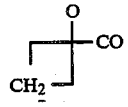

3H at 1.25 ppm (D, J=7 Hz, CH$_3$CH).

NMR no. 40-(b): 1H at 12.6 ppm (Se., ArNHCO)—1H at 8.75 ppm (D, J=9 Hz, CONH)—1H at 8.00 ppm (S, H thiazol in 3)—3H at 7.75 ppm (Se., CH$_2$N$^\oplus$H$_3$)—1H at 7.00 ppm (S, H thiazol)—1H at 5.98 ppm (D of D, J$_1$=9 Hz, J$_2$=4 Hz, H$_7$)—1H at 4.95 ppm (D, J=4 Hz, H$_6$)—1H at 4.40 ppm (D, J=13 Hz, CH$_2$SCO)—1H at 3.78 ppm (D, J=13 Hz, CH$_2$SCO)—2H at 3.75 ppm (Se., CH$_2$SO)—2H at 3.50 ppm (M, CH$_2$N$^\oplus$H$_3$)—2H at 2.80 ppm (M, CH$_2$CH$_2$N$^\oplus$H$_3$)—6H at 1.45 ppm (2S, (CH$_3$)$_2$C).

NMR no. 41-(b): 1H at 12.8 ppm (Se., NHCOCH$_2$)—1H at 8.80 ppm (D, J=9 Hz, CONH)—3H at 8.25 ppm (Se., CH$_2$N$^\oplus$H$_3$)—1H at 8.16 ppm (S, H thiazol in 3)—1H at 7.00 ppm (S, H thiazol)—1H at 5.96 ppm (D of D, J$_1$=9 Hz, J$_2$=4 Hz, H$_7$)—1H at 4.97 ppm (D, J=4 Hz, H$_6$)—1H at 4.40 ppm (D, J=13 Hz, CH$_2$SCO) 3H at 3.90 ppm (M, CH$_2$N$^\oplus$H$_3$ et CH$_2$SCO)—2H at 3.75 ppm (Se., CH$_2$SO)—6H at 1.44 ppm (2S, (CH$_3$)$_2$C).

NMR no. 42-(b): 1H at 10.6 ppm (S, ArNHCO)—1H at 8.70 ppm (D, J=9 Hz, CONH)—2H at 7.90 ppm (M, HAr 2', 6')—5H at 7.60 ppm (M, CH$_2$N$^\oplus$H$_3$ et HAr 3', 5')—1H at 7.00 ppm (S, H thiazol)—1H at 6.00 ppm (D of D, J$_1$=9 Hz, J$_2$=4 Hz, H$_7$)—1H at 4.95 ppm (D, J=4 Hz, H$_6$)—1H at 4.42 ppm (D, J=13 Hz, CH$_2$SCO) 1H at 3.90 ppm (D, J=13 Hz, CH$_2$SCO)—2H at 3.75 ppm (Se., CH$_2$SO)—2H at 3.05 ppm (M, CH$_2$N$^\oplus$H$_3$)—2H at 2.72 ppm (M, CH$_2$CH$_2$N$^+$H$_3$)—6H at 1.45 ppm (2S, (CH$_3$)$_2$C).

NMR no. 43-(b): 1H at 10.5 ppm (S, ArNHCO)—1H at 8.85 ppm (D, J=9 Hz, CONH)—2H at 7.90 ppm et 2H at 7.75 ppm (M, HAr)—3H at 7.70 ppm (Se., CH$_2$N$^\oplus$H$_3$)—1H at 6.95 ppm (S, H thiazol)—1H at 5.45 ppm (D of D, J$_1$=9 Hz, J$_2$=4 Hz, H$_7$)—1H at 4.97 ppm (D, J=4 Hz, H$_6$)—1H at 4.40 ppm (D, J=13 Hz, CH$_2$SCO) 1H at 3.86 ppm (D, J=13 Hz, CH$_2$SCO)—2H at 3.75 ppm (Se., CH$_2$SO)—2H at 3.02 ppm (M, CH$_2$N$^\oplus$H$_3$)—2H at 2.72 ppm (M, CH$_2$CH$_2$N$^\oplus$H$_3$)—4H at 2.40 ppm (M,

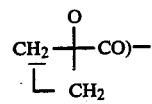

2H at 1.85 ppm (M,

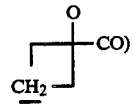

NMR no. 44-(b): 1H at 10.9 ppm (S, ArNHCO)—2H at 8.80 ppm (Se., CH$_2$N$^\oplus$H$_2$CH$_3$)—1H at 8.70 ppm (D, J=9 Hz, CONH)—2H at 7.90 ppm (D, J=8 Hz, HAr 2', 6')—2H at 7.70 ppm (D, J=8 Hz, HAr 3', 5')—1H at 6.98 ppm (S, H thiazol)—1H at 6.00 ppm (D of D, J$_1$=9 Hz, J$_2$=4 Hz, H$_7$)—1H at 4.97 ppm (D, J=4 Hz, H$_6$)—1H at 4.42 ppm (D, J=13 Hz, CH$_2$SCO)—3H at 3.90 ppm (M, CH$_2$N$^\oplus$H$_2$CH$_3$ at CH$_2$SCO)—2H at 3.75 ppm (Se., CH$_2$SO)—3H at 2.55 ppm (M, CH$_3$N$^\oplus$H$_2$—CH$_2$) 6H at 1.46 ppm (2S, (CH$_3$)$_2$C).

NMR no. 45-(b): 1H at 8.75 ppm (D, J=9 Hz, CONH)—1H at 8.55 ppm (D, H thiazol in 3)—3H at 8.50 ppm (Se., CH$_2$N$^\oplus$H$_3$)—1H at 7.00 ppm (S, H thiazol)—1H at 5.95 ppm (D of D J$_1$=9 Hz, J$_2$=4 Hz, H$_7$)—1H at 4.96 ppm (D, J=4 Hz, H$_6$)—2H at 4.46 ppm (M, CH$_2$N$^\oplus$H$_3$)—1H at 4.30 ppm (D, J=13 Hz, CH$_2$SCO)—1H at 3.90 ppm (D, J=13 Hz, CH$_2$SCO)—2H at 3.73 ppm (Se., CH$_2$SO)—6H at 1.44 ppm (2S, (CH$_3$)$_2$C).

NMR no. 46-(b): 1H at 8.87 ppm (T, J=8 Hz, NHCH$_2$Ar)—1H at 8.64 ppm (D, J=9 Hz, NHCO)—3H at 8.00 ppm (Se., H$_3$N$^\oplus$CH$_2$)—2H at 7.84 ppm (D, J=8 Hz, HAr 2', 6')—2H at 7.42 ppm (D, J=8 Hz, HAr3', 5')—1H at 6.94 ppm (S, H thiazol)—1H at 5.95 ppm (D of D, J$_1$=9 Hz, J$_2$=4 Hz, H$_7$)—1H at 4.95 ppm (D of D, J=4 Hz, H$_6$)—3H at 4.40 ppm (M, ArCH$_2$NH et CH$_2$SCO)—1H at 3.88 ppm D, J=13 Hz, CH$_2$SCO)—2H at 3.74 ppm) (Se., CH$_2$S→O)—2H at 3.58 ppm (M, OCCH$_2$N$^\oplus$H$_3$)—6H at 1.47 ppm (2S, (CH$_3$)$_2$C).

The products of the invention have been studied as regards their pharmacological properties and, more especially, bacteriostatic action. This has been determined in vitro by the dilution method, and the study was on Gram negative strains.

Results, expressed in minimum inhibiting concentrations (MIC— μg/ml), are collected in the following table (Table III).

TABLE III

| | MIC (μg/ml) ON DIFFERENT STRAINS | | | | | | |
|---|---|---|---|---|---|---|---|
| | STRAINS | | | | | | |
| PRODUCTS SR No. | Escherichia coli SOL RL 90 | Citrobacter 49 | Proteus vulgaris RL 99 bis | Serratia RL 72 | Klebsiella RO 30 | Enterobacter RO 154 | Pseudomonas RL 112 |
| 41 730 | 0.5 | 0.25 | ≦0.12 | 1 | 0.25 | 0.25 | 4 |
| 41 733 | 2 | 2 | 0.5 | 8 | 1 | 1 | 8 |
| 41 806 | 1 | 1 | 0.5 | 4 | 0.5 | 8 | 8 |
| 41 854 | 0.25 | 0.5 | ≦0.12 | 0.5 | 0.25 | 2 | 4 |
| 41 855 | 0.25 | 1 | ≦0.12 | 0.5 | 0.25 | 2 | 8 |
| 41 856 | 0.5 | 2 | ≦0.12 | 2 | 0.25 | 4 | 16 |
| 41 858 | 2 | 1 | 0.5 | 4 | 0.5 | 8 | 8 |
| 41 859 | 1 | 2 | 0.25 | 4 | 0.5 | 8 | 16 |
| 41 860 | 2 | 1 | 0.5 | 4 | 0.5 | 8 | 16 |
| 41 862 | 0.25 | 0.25 | ≦0.12 | 0.5 | 0.25 | 1 | 4 |
| 41 885 | 1 | 4 | 0.5 | 4 | 0.5 | 8 | 8 |
| 41 887 | 2 | 4 | 0.25 | 4 | 0.5 | 8 | 8 |
| 41 888 | 2 | 2 | 1 | 8 | 1 | 8 | 8 |
| 41 889 | 1 | 1 | 0.5 | 4 | 1 | 8 | 8 |
| 41 891 | 0.5 | 0.5 | 0.5 | 4 | 0.5 | 8 | 8 |
| 41 967 | 0.25 | 0.5 | ≦0.12 | 0.5 | 0.25 | 2 | 4 |
| 41 975 | 0.25 | 0.5 | 0.5 | 4 | 0.5 | 8 | 8 |
| 41 976 | 1 | 0.5 | 0.25 | 8 | 0.5 | 8 | 8 |
| 42 022 | 0.5 | 0.25 | ≦0.12 | 0.5 | 0.25 | 2 | 4 |
| 42 024 | 0.5 | 0.5 | 0.25 | 0.5 | 0.25 | 2 | 4 |
| 42 025 | 0.5 | 0.5 | 0.25 | 1 | 0.5 | 4 | 4 |
| 42 026 | 0.5 | 0.25 | ≦0.12 | 1 | 0.25 | 4 | 8 |
| 42 027 | 0.25 | 0.25 | ≦0.12 | 0.5 | 0.25 | 2 | 4 |
| 42 028 | 0.25 | 0.5 | ≦0.12 | 0.5 | 0.25 | 2 | 4 |
| 42 029 | 0.25 | 0.25 | ≦0.12 | 0.5 | 0.25 | 2 | 8 |
| 42 042 | ≦0.12 | ≦0.12 | ≦0.12 | 2 | ≦0.12 | 1 | 4 |
| 42 073 | 1 | 0.5 | 0.5 | 2 | 0.5 | 4 | 4 |
| 42 074 | 1 | 0.5 | 0.5 | 4 | 0.5 | 8 | 8 |
| 42 117 | 0.25 | 0.25 | ≦0.12 | 0.5 | ≦0.12 | 1 | 4 |
| 42 118 | 1 | 0.5 | 0.25 | 4 | 0.5 | 16 | 8 |
| 42 119 | 0.5 | 0.25 | ≦0.12 | 4 | 0.5 | 8 | 8 |
| 42 208 | 0.5 | 0.5 | ≦0.12 | 1 | 0.5 | 0.25 | 4 |
| 42 209 | 0.25 | ≦0.12 | ≦0.12 | 0.5 | 0.25 | ≦0.12 | 4 |
| 42 210 | 1 | 0.5 | 0.25 | 1 | 0.5 | 0.25 | 4 |
| 42 211 | ≦0.12 | ≦0.12 | ≦0.12 | ≦0.12 | ≦0.12 | ≦0.12 | 64 |
| 42 212 | ≦0.12 | ≦0.12 | ≦0.12 | 0.25 | ≦0.12 | ≦0.12 | 4 |
| 32 213 | 0.25 | ≦0.12 | ≦0.12 | 0.5 | 0.25 | ≦0.12 | 16 |
| 42 214 | ≦0.12 | ≦0.12 | ≦0.12 | 0.5 | ≦0.12 | ≦0.12 | 16 |
| 42 215 | ≦0.12 | ≦0.12 | ≦0.12 | 0.25 | ≦0.12 | ≦0.12 | 8 |
| 42 216 | ≦0.12 | ≦0.12 | ≦0.12 | 0.5 | ≦0.12 | ≦0.12 | 8 |
| 42 217 | ≦0.12 | ≦0.12 | ≦0.12 | 0.25 | ≦0.12 | ≦0.12 | 16 |
| 42 218 | 0.5 | 0.25 | 0.5 | 2 | 0.5 | 0.5 | 64 |
| 42 219 | 0.5 | ≦0.12 | ≦0.12 | 1 | 0.5 | 0.5 | 4 |
| 42 221 | 0.25 | ≦0.12 | ≦0.12 | 2 | ≦0.12 | 0.25 | 64 |
| 42 222 | 0.5 | ≦0.12 | ≦0.12 | 1 | 0.5 | 0.5 | 8 |
| 42 320 | ≦0.125 | ≦0.125 | ≦0.125 | 0.5 | ≦0.125 | ≦0.125 | 4 |
| 42 321 | 0.5 | 0.5 | ≦0.125 | 1 | 0.5 | 0.25 | 8 |
| 42 371 | 0.5 | 0.25 | ≦0.125 | 0.5 | 0.25 | 0.25 | 8 |
| 42 372 | 0.25 | ≦0.125 | ≦0.125 | 0.25 | 0.25 | ≦0.125 | 4 |
| 42 374 | 0.5 | 0.25 | ≦0.125 | 1 | 0.25 | 0.25 | 4 |
| 42 379 | 0.25 | ≦0.125 | ≦0.125 | 0.5 | ≦0.125 | ≦0.125 | 8 |
| 42 380 | ≦0.125 | ≦0.125 | ≦0.125 | 1 | ≦0.125 | ≦0.125 | 4 |
| 42 395 | ≦0.125 | ≦0.125 | ≦0.125 | 0.5 | ≦0.125 | ≦0.125 | 4 |
| 42 396 | ≦0.125 | ≦0.125 | ≦0.125 | 1 | ≦0.125 | ≦0.125 | 8 |
| 42 397 | ≦0.125 | ≦0.125 | ≦0.125 | 1 | ≦0.125 | ≦0.125 | 8 |
| 42 456 | 0.25 | ≦0.125 | ≦0.125 | 0.5 | ≦0.125 | ≦0.125 | 4 |
| 42 457 | 0.5 | 0.25 | ≦0.125 | 0.5 | 0.25 | 0.25 | 8 |
| 42 461 | 0.25 | ≦0.125 | ≦0.125 | 2 | ≦0.125 | ≦0.125 | 8 |
| 42 462 | 0.25 | ≦0.125 | ≦0.125 | 0.5 | ≦0.125 | ≦0.125 | 4 |
| 42 463 | ≦0.125 | ≦0.125 | ≦0.125 | 0.5 | ≦0.125 | ≦0.125 | 4 |
| 42 464 | ≦0.125 | ≦0.125 | ≦0.125 | 0.5 | ≦0.125 | ≦0.125 | 4 |
| 42 465 | ≦0.125 | ≦0.125 | ≦0.125 | 2 | 0.5 | 0.5 | 8 |
| 42 466 | 0.5 | 0.25 | ≦0.125 | 2 | 0.5 | 0.5 | 4 |
| 42 467 | 0.25 | ≦0.125 | ≦0.125 | 2 | 0.25 | 0.5 | 4 |
| 42 471 | 0.5 | 0.25 | ≦0.125 | 0.5 | 0.25 | 0.25 | 8 |
| 42 472 | 0.25 | ≦0.125 | ≦0.125 | 0.25 | ≦0.125 | ≦0.125 | 4 |
| 42 473 | 0.25 | ≦0.125 | ≦0.125 | 0.25 | ≦0.125 | ≦0.125 | 4 |
| 42 474 | 0.25 | ≦0.125 | ≦0.125 | 0.25 | 0.25 | ≦0.125 | 4 |
| 42 531 | 0.5 | 0.25 | ≦0.125 | 0.5 | 0.25 | 0.5 | 8 |
| 42 532 | 0.5 | 0.25 | ≦0.125 | 1 | 0.25 | 0.5 | 8 |
| 42 533 | 0.5 | 0.25 | ≦0.125 | 1 | 0.25 | 0.5 | 8 |
| 42 534 | 0.5 | 0.25 | ≦0.125 | 1 | 0.25 | 0.5 | 8 |
| 42 535 | 0.5 | 0.25 | ≦0.125 | 1 | 0.25 | 0.5 | 8 |

TABLE III-continued

MIC (μg/ml) ON DIFFERENT STRAINS

| PRODUCTS SR No. | Escherichia coli SOL RL 90 | Citrobacter 49 | Proteus vulgaris RL 99 bis | Serratia RL 72 | Klebsiella RO 30 | Enterobacter RO 154 | Pseudomonas RL 112 |
|---|---|---|---|---|---|---|---|
| 42 536 | 0.5 | 0.25 | ≦0.125 | 0.5 | 0.25 | 0.5 | 8 |
| 42 537 | 0.25 | 0.25 | ≦0.125 | 0.5 | 0.25 | 0.25 | 8 |
| 42 538 | 0.5 | 0.25 | ≦0.125 | 0.5 | 0.25 | 0.25 | 8 |
| 42 540 | 0.25 | 0.125 | ≦0.125 | 0.25 | ≦0.125 | ≦0.125 | 4 |
| 42 541 | 0.5 | 0.25 | ≦0.125 | 0.5 | ≦0.125 | 0.25 | 4 |
| 42 542 | 0.5 | 0.5 | ≦0.125 | 0.5 | ≦0.25 | 0.5 | 8 |
| 42 546 | 0.25 | 0.25 | ≦0.125 | 1 | 0.25 | 0.25 | 4 |
| 42 547 | 0.5 | 0.25 | ≦0.125 | 0.5 | 0.25 | 0.5 | 4 |
| 42 548 | 0.25 | ≦0.125 | ≦0.125 | 0.5 | 0.125 | 0.25 | 2 |
| 42 549 | 0.25 | ≦0.125 | ≦0.125 | 0.5 | 0.25 | 0.25 | 4 |
| 42 581 | 0.125 | | | | 0.125 | 2 | 4 |
| 42 582 | 0.25 | | | | 0.25 | 2 | 8 |
| 42 583 | 1 | | | | 0.5 | 4 | 8 |
| 42 584 | 0.25 | | | | 0.25 | 2 | 4 |
| 42 585 | 0.25 | | | | 0.25 | 8 | 4 |
| 42 586 | 0.25 | | | | 0.25 | 16 | 4 |
| 42 587 | 0.25 | | | | 0.25 | 8 | 4 |
| 42 657 | 0.25 | | | | 0.25 | 4 | 8 |
| 42 658 | 0.125 | | | | 0.125 | 8 | 4 |
| 42 661 | 0.5 | | | | 0.25 | 1 | 8 |
| 42 663 | 4 | | | | 1 | 4 | 8 |
| 42 664 | 1 | | | 4 | 0.5 | 4 | 8 |
| 42 665 | 0.5 | | | | 0.5 | 2 | 8 |
| 42 674 | 1 | | | | 0.5 | 2 | 8 |
| 42 675 | 0.125 | | | | 0.125 | 1 | 4 |
| 42 676 | 0.25 | | | | 0.25 | 2 | 8 |
| 42 685 | 2 | | | | 1 | 2 | 8 |
| 42 686 | 2 | | | | 1 | 2 | 8 |
| 42 687 | 2 | | | | 1 | 4 | 8 |
| 42 688 | 0.125 | | | | 0.25 | 4 | 4 |
| 42 689 | 0.125 | | | | 0.25 | 4 | 4 |
| 42 690 | 0.5 | | | | 0.5 | 8 | 4 |
| 42 781 | 0.25 | | | | 0.125 | 2 | 4 |
| 42 782 | 0.25 | | | | 0.125 | 2 | 4 |
| 42 783 | 0.25 | | | | 0.125 | 2 | 8 |
| 42 811 | 0.125 | | | | 0.125 | 2 | 4 |
| 42 814 | 0.5 | | | | 0.25 | 8 | 8 |
| 42 815 | 0.125 | | | | 0.25 | 8 | 8 |
| 42 817 | 0.125 | | | | 0.25 | 4 | 4 |
| 42 818 | 0.125 | | | | 0.125 | 4 | 4 |
| 42 848 | 0.125 | | | | 0.125 | 2 | 4 |
| 42 849 | 0.125 | | | | 0.125 | 2 | 4 |
| 42 850 | 0.5 | | | | 0.25 | 2 | 8 |
| 42 851 | 0.5 | | | | 0.25 | 1 | 8 |
| 42 852 | 0.25 | | | | 0.125 | 1 | 8 |
| 42 857 | 0.5 | | | | 1 | 8 | 8 |

The results presented in Table III show good activity on Gram negative bacteria of the products according to the invention.

To evaluate the stability of these products towards beta-lactamases, their MIC was determined on isogenic strains producing and not producing beta-lactamases. The results are expressed in μg/ml in Table IV.

TABLE IV

MIC (μg/ml) ON STRAINS PRODUCING BETA-LACTAMASES AND NOT PRODUCING (indicated by*)

| | Strains | | | | | |
|---|---|---|---|---|---|---|
| | Escherichia coli | | Serrtia liquefaciens | | Proteus vulgaris | |
| PRODUCTS SR no. | 255 | 255/L.7 * | SL/326 A | SL 1326 S * | GN 76/C.1 | GN 76/C.1/3 * |
| 41 730 | 0.25 | ≦0.12 | 0.5 | ≦0.12 | 0.25 | 0.25 |
| 41 854 | ≦0.12 | ≦0.12 | 0.25 | ≦0.12 | 0.25 | 0.25 |
| 41 855 | ≦0.12 | ≦0.12 | 0.25 | ≦0.12 | ≦0.12 | ≦0.12 |
| 41 862 | ≦0.12 | 0.12 | ≦0.25 | ≦0.12 | ≦0.12 | ≦0.12 |
| 41 967 | ≦0.12 | ≦0.12 | 0.25 | ≦0.12 | ≦0.12 | ≦0.12 |
| 41 973 | 0.25 | 0.25 | 0.25 | ≦0.12 | 0.5 | 0.5 |
| 41 975 | 0.5 | 0.5 | 0.25 | ≦0.12 | 0.5 | 0.5 |
| 42 022 | 0.25 | 0.25 | ≦0.12 | ≦0.12 | ≦0.12 | ≦0.12 |
| 42 024 | 0.25 | ≦0.12 | 0.25 | 0.06 | 0.25 | 0.25 |
| 42 027 | 0.12 | 0.06 | 0.25 | ≦0.06 | 0.12 | 0.12 |
| 42 028 | 0.12 | 0.12 | 0.12 | ≦0.06 | 0.25 | 0.25 |
| 42 042 | ≦0.12 | ≦0.12 | 0.25 | ≦0.12 | ≦0.12 | ≦0.12 |
| 42 073 | 0.5 | 0.25 | 0.25 | ≦0.12 | 0.5 | 0.5 |
| 42 074 | 0.5 | 0.25 | 0.25 | 0.12 | 0.5 | 0.5 |

TABLE IV-continued

MIC (μg/ml) ON STRAINS PRODUCING BETA-LACTAMASES AND NOT PRODUCING (indicated by*)

| PRODUCTS SR no. | Escherichia coli 255 | 255/L.7 * | Serrtia liquefaciens SL/326 A | SL 1326 S * | Proteus vulgaris GN 76/C.1 | GN 76/C.1/3 * |
|---|---|---|---|---|---|---|
| 42 117 | 0.125 | 0.06 | 0.12 | ≦0.06 | ≦0.06 | ≦0.06 |
| 42 118 | 0.5 | 0.25 | 0.25 | 0.12 | 0.5 | 0.5 |
| 42 119 | 0.25 | 0.12 | 0.25 | ≦0.06 | 0.12 | 0.12 |
| 42 320 | 0.0625 | 0.0625 | 0.125 | ≦0.0312 | ≦0.0312 | 0.125 |
| 42 395 | 0.0625 | 0.0625 | 0.125 | ≦0.0312 | ≦0.0312 | ≦0.0312 |
| 42 456 | 0.0625 | ≦0.0312 | 0.25 | 0.0625 | ≦0.0312 | 0.125 |
| 42 457 | 0.125 | ≦0.0312 | 0.0625 | 0.0625 | ≦0.0312 | 0.0625 |
| 42 466 | 0.125 | 0.125 | 1 | ≦0.0312 | ≦0.0312 | 0.0625 |
| 42 467 | 0.0625 | ≦0.0312 | 0.125 | 0.125 | ≦0.0312 | 0.0625 |
| 42 474 | 0.0625 | 0.0625 | 0.125 | ≦0.0312 | 0.0625 | 0.0625 |
| 42 531 | 0.125 | 0.0625 | 0.125 | 0.0625 | 0.0625 | |
| 42 533 | 0.125 | 0.0625 | 0.125 | ≦0.0312 | 0.0625 | 0.125 |
| 42 535 | 0.125 | ≦0.0312 | 0.0625 | 0.125 | 0.0625 | 0.125 |
| 42 546 | 0.0625 | ≦0.0312 | 0.25 | ≦0.0312 | ≦0.0312 | 0.125 |
| 42 547 | 0.125 | ≦0.0312 | 2 | 0.125 | 0.0625 | 0.25 |
| 42 548 | 0.625 | ≦0.0312 | 0.125 | ≦0.0312 | 0.0625 | 0.0625 |
| 42 549 | 0.125 | 0.0625 | 0.125 | ≦0.0312 | ≦0.0312 | 0.0625 |
| 42 664 | 0.25 | 0.0625 | 0.25 | 0.0625 | 0.125 | 0.25 |
| 42 673 | 0.25 | 0.25 | 0.25 | 0.0625 | 0.25 | 0.25 |

According to the results of table IV, the products according to the invention have an equal or comparable activity on strains producing or not producing beta-lactamases, which shows the good stability towards beta-lactamases.

The therapeutic effectiveness of the products was determined on the septicemic model of the mouse. the septicemia was initiated by the intraperitoneal innoculation of 0.5 ml of a suitable dilution of a suspension of the Escherichia coli SOL 90 strain. The products were administered in solution in a phosphate buffer pH 7.0 in a volume of 0.2 ml sub-cutaneously to batches of 10 mice, 1 to 5 hours after innoculation of the microorganism. After 4 days of observation in the course of which the mortality was noted, the 50% effective doses (DE 50) were calculated by the Muench and Reed method.

The results obtained are shown in Table V.

TABLE V $DE_{50}$ (mg/kg) IN THE SEPTICEMIC MODEL IN THE MOUSE

| PRODUCTS SR no. | STRAINS Escherichia coli SOL 90 | Klebsiella RO 30 |
|---|---|---|
| 41 730 | 1.4 | 0.79 |
| 41 854 | 0.23 | 0.19 |
| 41 855 | 0.16 | 0.17 |
| 41 862 | 0.13 | 0.10 |
| 41 973 | 0.22 | 0.4 |
| 42 042 | 0.05 | ND |
| 42 073 | 0.33 | ND |
| 42 117 | 0.11 | ND |
| 42 119 | 0.16 | ND |

ND = not determined

According to the results of table V, the products, according to the invention, show good IN VIVO therapeutic activity.

In addition, according to tests carried out up till now on animals, the toxicity of the products according to the invention has appeared to be sufficiently low to enable their use in therapeutics.

The products of the invention can hence be employed as antibiotics in human or veterinarian medicine. They have a wide spectrum on Gram negative organisms and can be used in all germ sensitive bacterial infections.

The products can be administered by the general route (parenteral, oral or topically).

The pharmaceutical compositions are produced from the compounds (I) in soluble forms obtained by salification of one of the acid functions of the molecule or of one of the amine functions of the B chain.

The pharmaceutical compositions can be solid or liquid and be presented, for example, in the form of injectable preparations, tablets, gelules, granules, pommades, creams, gels or suppositories. The posology can vary within wide proportions, in particular according to the type and seriousness of the infection to be treated and according to the mode of administration. Mostly, in the adult, by the injectable route, it is comprised between 0.250 g and 4 g per day.

By way of example of pharmaceutical composition, there may be prepared injectable solutions of the sodium salt of SR 41 973:

To a solution of 3 g of dihydrochloride of SR 41 973 in 25 ml of water, is added drop by drop a saturated solution of sodium bicarbonate. When the pH is 3, the solution is filtered. The pH is then adjusted to 3.6 by the addition of some drops of saturated solution of sodium bicarbonate. The solution is cooled to +4° C. and the SR 41 973 starts to crystallize. 75 ml of acetone are added slowly drop by drop. After ½ hour of stirring at +4° C., the crystals are filtered and washed twice with a mixture (1-1) of water and acetone and finally washed twice with 20 ml of acetone. The product is dried in the dessicator over $P_2O_5$. 1.9 g of the compound SR 41 973 is obtained.

1.25 g of the SR 41 973 so obtained is suspended in 15 ml of water at +4° C. A solution of 0.168 g of sodium bicarbonate in 3 ml of water is added drop by drop. The clear solution thus obtained is frozen and freeze-dried, after sterile filtration, to obtain the sodium salt of 41 973 ready for injection.

We claim:

1. Cephalosporin compounds of the formula:

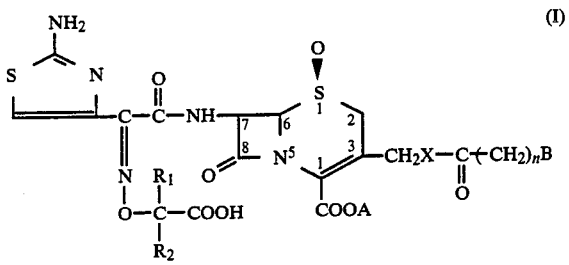 (I)

in which:
the COOA group at the 4 position is an acid radical, or an alkali or alkaline-earth metal salt or an amino acid or amine salt, or an ester radical easily hydrolyzable or metabolically labile and pharmaceutically acceptable, X denotes an oxygen atom or a sulfur atom, n is zero or 1, $R_1$ and $R_2$ each denote, independently, hydrogen or a lower alkyl group, or $R_1$ and $R_2$ taken together with the carbon atom to which they are linked form a cyclobutyl or cyclopentyl nucleus, B is the residue of a primary or secondary amine selected from the group consisting of Z—NH—R where Z is a straight or branched chain alkylene group having from 2 to 7 carbon atoms, optionally interrupted by a sulfur atom and optionally substituted by a hydroxyl, thiol, methylthio, amino acetamido, carbamoyl, phenyl, hydroxyphenyl or imidazoyl group, a cyclopentylidene or cyclohexylidene group, R represents a hydrogen atom or an alkyl group having from 1 to 3 carbon atoms, Z'—Alk—NH—R where Z' represents a 1,2-phenylene or 1,3-phenylene or 1,4-phenylene group optionally substituted by a halogen atom or by 1 or 2 methoxy groups or by 1, 2 or 3 methyl groups or Z' represents a 1,2-cyclohexylene, 1,3-cyclohexylene or 1,4-cyclohexylene group, Alk represents a straight or branched alkyl group having from 1 to 3 carbon atoms,

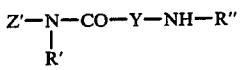

where Z' is as defined above,

Y denotes an alkyl $(CH_2)_m$ group in which m=0, 1, 2, 3 or 4, or a branched alkyl group having 2 or 3 carbon atoms or Y with NH—R'' constitutes a ring

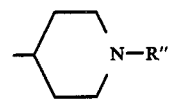

R' and R'', identical or different, having the same meaning as that given for R above, Z''—NH—R where Z'' is a 1,3-cyclohexylene or 1,4-cyclohexylene group and R is as previously defined,

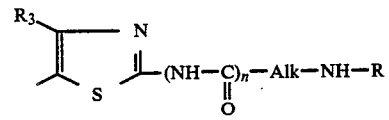

where $R_3$ represents a hydrogen atom or a methyl group, n=0 or 1 and Alk and R are as previously defined, a 2-piperidyl, 3-piperidyl or 4-piperidyl group optionally substituted on the nitrogen atom by a —CO—Alk—$NH_2$ or a

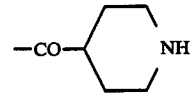

group where Alk is as previously defined,
and the salts of said compounds with pharmaceutically acceptable acids.

2. Compounds according to claim 1, which are in one of the syn and anti forms.

3. Pharmaceutical composition with bacteria-static action containing, as active ingredient, a compound according to claim 1 in combination with a pharmaceutically acceptable vehicle.

4. Pharmaceutical composition according to claim 3, packaged in the form of ampoules and containing 0.25 to 4 g of the compound according to claim 1.

* * * * *